(12) United States Patent
Weaver et al.

(10) Patent No.: US 7,582,451 B2
(45) Date of Patent: Sep. 1, 2009

(54) CAROTENE SYNTHASE GENE AND USES THEREFOR

(75) Inventors: Craig A. Weaver, Boulder, CO (US);
James G. Metz, Longmont, CO (US);
Jerry M. Kuner, Longmont, CO (US);
Frank H. Overton, Jr., Boulder, CO (US)

(73) Assignee: Martek Biosciences Corporation, Columbia, MD (US)

( * ) Notice: Subject to any disclaimer, the term of this patent is extended or adjusted under 35 U.S.C. 154(b) by 0 days.

(21) Appl. No.: 11/557,761

(22) Filed: Nov. 8, 2006

(65) Prior Publication Data

US 2007/0269869 A1    Nov. 22, 2007

Related U.S. Application Data

(62) Division of application No. 10/438,784, filed on May 14, 2003, now Pat. No. 7,202,067.

(60) Provisional application No. 60/380,721, filed on May 14, 2002.

(51) Int. Cl.
*C12P 19/00* (2006.01)
*C12P 7/64* (2006.01)
*A01H 5/00* (2006.01)

(52) U.S. Cl. .................. 435/72; 435/41; 435/134; 435/175; 435/298

(58) Field of Classification Search ................. None
See application file for complete search history.

(56) References Cited

U.S. PATENT DOCUMENTS

| | | | |
|---|---|---|---|
| 5,130,242 | A | 7/1992 | Barclay |
| 6,551,795 | B1 | 4/2003 | Rubenfield et al. |
| 6,582,941 | B1 | 6/2003 | Yokochi et al. |
| 6,783,951 | B2 | 8/2004 | Long, II |
| 7,202,067 | B2 | 4/2007 | Weaver et al. |
| 2007/0253933 | A1 | 11/2007 | Weaver et al. |
| 2007/0269881 | A1 | 11/2007 | Weaver et al. |

FOREIGN PATENT DOCUMENTS

WO    WO 02/41833    5/2002

OTHER PUBLICATIONS

Arrach, N., et al, "A single gene for lycopene cyclase, phytoene synthase, and regulation of carotene biosynthesis in Phycomyces", PNAS, 98(4):1687-1692 (2001).
Bentley, S.D., et al, Nature, 417:141-147 (2002).
Chin, A., "On the Preparation and Utilization of Isolated and Purified Oligonucleotides," published Mar. 14, 2002, 2-page description, first 100 pages of Readme.txt and Short.txt, and CD-ROM containing Chin publication and Disclose.txt, Readme.txt and Short.txt documents.
Database EMBL 'Online!, Sequence 13 from Patent WO 0185201, XP002363296, retrieved from EBI Accession No. EM.sub—PRO:AX301252 (Nov. 30, 2001).
Database GenCore on EST, Accession No. ABQ18802 "Oligonucleotide for detecting cytosine methylation Seq ID No. 5393" gene sequence, Jul. 12, 2002.
Franklin et al., J. Nutr., 129:2048-2052 (1999) Dietary Marine Algae (*Schizochytrium* sp.) Increases Concentrations of Conjugated Linoleic, Docosahexaenoic and Transvaccenic Acids in Milk of Dairy Cows.
Mahairas G.G. et al., "Sequence-tagged connectors: A sequence approach to mapping and scanning the human genome", Proceedings of the National Academy of Sciences of the USA, vol. 96, No. 17 (Aug. 17, 1999), pp. 9739-9744, XP002363294.
Ng W.V. et al, "Genome sequence of *Halobacterium* species NRC-1" Proceedings of the National Academy of Sciences of USA, National Academy of Science, Washington, DC, vol. 97, No. 22 (Oct. 24, 2000) pp. 12176-12181, XP002352666.
Schmidhauser, T. J., et al, J. Biol. Chem., 269(16):12060-12066 (1994).
Smith, D., et al, J. Bacteriol., 179(22):7135-1755 (1997).
Teramoto, M., et al, Marine Biotechnology Institute, 545:120-126 (2003).
Victor, W., et al, PNAS, 97(22):12176-12181 (2000).
Viveiros, M., et al, FEMS Microbiology Letters, 187:95-101 (2000).
International Search Report for International (PCT) Patent Application No. PCT/US03/15229, mailed May 27, 2004.
International Preliminary Examination Report for International (PCT) Patent Application No. PCT/US03/15229, mailed Aug. 10, 2004.
Translation of First Office Action for Chinese Patent Application No. 038168057, issued Jul. 7, 2006.
Supplementary European Search Report for European Patent Application No. 03731185.9-2401, mailed Feb. 8, 2006.
Official Action for European Patent Application No. 03731185.9-2401, mailed Apr. 26, 2006.
Official Action for European Patent Application No. 03731185.9-2401, mailed May 4, 2007.
Examination Report for European Patent Application No. 03731185.9-2401, mailed Nov. 26, 2007.

*Primary Examiner*—Jon P Weber
*Assistant Examiner*—Kagnew H Gebreyesus
(74) *Attorney, Agent, or Firm*—Sheridan Ross P.C.

(57) ABSTRACT

Described herein is a novel three domain gene from *Schizochytrium*, denoted carotene synthase, that encodes a protein with three different enzymatic activities: phytoene dehydrogenase (PD), phytoene synthase (PS), and lycopene cyclase (LC). Also described is the isolated gene encoding the carotene synthase, homologues thereof, the enzyme encoded by such gene, biologically active portions and homologues thereof, recombinant nucleic acid molecules, microorganisms and plants that have been genetically modified to increase or decrease the action of such gene, and methods of producing carotenoids and derivatives thereof or methods of producing microorganisms and lipid products lacking pigmentation using the knowledge of the carotene synthase described herein.

2 Claims, 2 Drawing Sheets

SEQUENCE LISTING

<160> NUMBER OF SEQ ID NOS: 9

<210> SEQ ID NO 1
<211> LENGTH: 5898
<212> TYPE: DNA
<213> ORGANISM: Schizochytrium

<400> SEQUENCE: 1

```
acgcgtggtc gacgcccgga ctggtatctc gacatgactt acacggtcct ggacaatgac      60
gctgtgcacg tgcaagttag ctaccctatg accggcggat ggattggcgt gggcctttcc     120
gacaatggcg acatggttgg ctcgcatgcc gtcattgccg gccaaggcgt atccggtatt     180
cctgcaccaa tcggcgagta caagctcact gcgtacgatg cgccaagact ttcttcctcg     240
agagccatca ccgacacctc catcgaggtc aacaatggcg tcatgaccat ggagtttacg     300
gcaaaaacca ttgccggccg gagcattgac gtttcgggtg atggggatcg catcatttac     360
gccgtctacg agggaagctc cttcggcacg cagcatgccc gagcgggcga ttccaccgtc     420
aactggtctt cgcctgtgcc ttccagcgca gtgcgccttg ccccgctcgg tcttattatt     480
cttggcgctc tcgtcaatgt gatcatgatc tagtcgaacg tgcaatctag ccaatgaaaa     540
aagagtccag ttctatctga atttttcact ttctaaatct cgcatcgaca atctactttt     600
caaatctcgc aacaaagctg atcttgtttc tccctcaccc agttctatct gaattttttcc    660 ttttctgaag ctcgcgttaa caatctactt ttcgaatctg tcaacaaagc tgatcttgtt     720
tctcccccct atcccttcc ctccccctt ctttgggatc ttgttgtgcg tgtcgccct       780 tcaacttctt tgttcgacga tgacctccac ctagcctgtg aagctcatcg tctccgagta     840
tttctggcct gctccaattc ctctcttcca ttctccatcg catacatgca tgttctttgg     900
tctcactccg agccatgctt cttcggtcac tacttcatct atttgactag gcctctgttc     960
gagcgacgaa ccctccgtgt tcgcgggtgt tcattctctg caaagtggtc cgtaaccgtg    1020
actaccggac acctcgcgta cactacattc gggacggacg cggccgagcg cgacgtctct    1080
gggcccggcc tgccgccccc ggggccgcgg cttcctcgcg ccgccagccg cgtccaagtc    1140
gccagcgcga ggtcgcgcga gtcgaaggag acgttgtcga tctcgaccct cgccatgcgc    1200
gtgacgggtg accgcctcac cggatcccgc cctccgcgcg ctgccttcat tccttcattc    1260
cttcattcct tcactcaatc ctgcatcatc catcgcccgc ccgcccgctc gcacgcacca    1320
gaggcgcgca ttgcgggcca gggcgccgcc tgcagaccgc catcgcgccc gccttctgcc    1380
gcgcctcgct cgctcggaga ccgagatggc gcgcagggcg tcgcgcctcg gcgccgccgt    1440
cgtcgtcgtc ctcgtcgtcg tcgcctccgc ctgctgctgg caagccgctg cggacgtcgt    1500
ggacgcgcag ggcgcaagag gcccgggca agagagcgac ggcggccgcg cgaagaagcg     1560
```

```
catcgccgtg ctcggggccg ggtacgcagg cctgtccgca gcctgcgaac tgagcagact    1620
gggacacgag gtcgtggttc tcgagaagaa cgcctacgtg ggaggccgtg cccaccagtt    1680
cgaggtcgag gccgacaatg ggcagacctt caagttcgac gccgggccca gctggtactg    1740
gatgcccgag gtctttgacc gcttctttgc gcggtatggg cgaaccgtcc aggagttcta    1800
ccagctcgag cgcctcgacc cggcatatcg catcattcgc aatgaccaca acggcgaggg    1860
taccgtcgat gtgcccggcg cttcgagcga ggccttcatg tcttgggcac gccaattgaa    1920
cggcgatgcc cgactcgtcg accgtctcat ggacgaggcc aaggcaaagt acgaggaggg    1980
cgtcttcaag tggatttggc atcccatggt ctcgtggtgg gaaatgatcg atctcaatct    2040
cgcgcgcgct gccttgcagt atgacatgtt caacagcttt gtcgctcacc tgcaaaagta    2100
catttcaagc gataccctgc tcatgattct caagtggccc gtcatctttc tcggggcctc    2160
gcctaatggc gcccctgcgt tgtattccat gatgacctat ggcggtcacg cgctcggcac    2220
cttttatcca actggaggcc tcgcgcggcc cgtcgttgcc atcgccgagc ttgccagaga    2280
cctcggcgtc gacattcagc tcgatgccga ggtcacctcg tttcgctttg acgagagcgg    2340
ccgtggtgtt caagctgttt gcactcgcaa cgatcgctgt gaggctgtcg atggggtcgt    2400
ggctgccgcc gattaccacc acgttgagca gacccttctg cccccggaac ttcgtcgcta    2460
cgagcagggt ttttgggatg cccaagtcat gtcgccgtcc tgcgtcctct tctacctcgg    2520
cttcgatcac cgcatccaag ggctcaccca tcatacgttc ttctttgacc gagaccctcga   2580 cgctcatctt cacgcggcct ttgacacgca cacttgggcc gaggaacccg tcttttacgt    2640
gtcagccacc tcgaaaacgg acccaagcgt agtttctggt cagggcgagg cgctctttgt    2700
gctcgttccc atctcctacc agctcaacgg cacagacaac gctgcgcgtc gggagcaaat    2760
cctacacacc gtgctcacac gcatggaaga gaacttgaag cagcccctcc gcgagtggct    2820
cgtctaccaa aagtcctacg ggacaacgga ttttgagcgc gactttcact cctttcgtgg    2880
caatgctttt ggccacgcca acacgctttc gcagtcgctc gtgctcaaac cctccatgga    2940
ctctttactc aataatctcg tctttgctgg ccatttgacg aatcccggcc caggcgtgcc    3000
gccgtccatc gtctcgggca ctgtttcggc caacctgttg catgacaaaa tccaagtgac    3060
agcaaatcac catgcactgg ggttcacgct cctcggagct ttccttggag ccttgttact    3120
cggtattctg gctctctcgg tattctcaac tcgcttcgtg tcgtatgtgg agtgcatcag    3180
actcttgtat gtgcacgggc ggacttactt tgccgccgcc acgctcatga agcccatggc    3240 cttctctcgac acggcggcca tgtacgggct ttttcgcgtt gccgacgact acgtcgacaa    3300
tgttggcgac gccggcgagc ggcagcgaa cctcgacgcc ttcatggcgg acttttggcg    3360
atgctgggaa tccggccgag cgactacgc gcgccatccg acgctccctg ccatcatcga    3420 gtcgcgcac cgtcgtgcat acccgcggga actctttgag cgtttcttcc gctccatgcg    3480
gatggacgcc aaacgaaagg tcgtctgcct caccatggat gatacgatgg agtacatgga    3540
aggcagcgcg gctgtcattg gcgagttcat gctacctatt ctcatgcccg acagagactc    3600
tttggctttc aagcaagccg taccgcacgc gcgcaatctt ggactcgctt tccaaatcac    3660
caacatgctt cgggatattg gcgaggataa tcgcttgggt cgccagtaca ttcctgtcga    3720
cgcctgcaag cgccatggtc taaacggcaa gctcacgtca catgaacagc ctggctttcg    3780
cgagctcatg gaggaaatgt tcgctttcac cgacaatctc tatgctagtg ctgaccttgg    3840
catcgacatg ttgcctgagc aggtgcgcga cgtcattcgt gtggcgcgtc ttgcgtatca    3900
```

```
ccgcatccac gacaagatcc gcgcagcgaa ttacgacatt ttcaccgctc gacgtcgagt   3960
tccccttgga gaaaagttaa cgattctcgt cgataccgta ccgcgactca agctcgcccg   4020
cattgcgctc accgagctca tttgtgctac actctatggt cttcgcgcc cgcatattgc    4080
tttcgtttgg attggcgccg tatgggcgag ctggctcgag tggccgggat gctcgtacct   4140
gcgctttcac gggctcttca tactaccgcc gctcctcatg ctcgcccgtt tggcgcacca   4200
acgcgctgtt gccgacaagc aggtcccctt cttgcgccgc gctggtttct ggactgtggc   4260
actttgcgtc gttgcaacac tttacaccac accatgggac aattttctcg tgtatcgccg   4320
cgtctgggga tacccgccgg agcgcattct ctttgtcatt gggtatgtgc ccattgaaga   4380
gtacatgttc ttcacgctcg aaaccatgtt ggtcgcggcg gtctggctac aggttttca    4440
gcccacgacg ttgcaggccg aggtaggccc acgtggaaag gggggcatgc tcgttctcgc   4500
gagtcttgga ctcgtctggg ttgccggcct ttcgtgtttg gcctcggagc aaagcttata   4560
cattggtctc attctcagct ggtctatgcc cgtcctcatt ctgcaatgga gtctcggtgc   4620
acatgtgctc actacgcatg caaagccggt cctgacgacg atcgtgtcgg ccacagcgta   4680
cctttgcgtg gccgacgaat gggcgattcg tcacggcatc tggcgcatca atcctgcaaa   4740
tcttgtgttg cccatgggca aacatgcact tcccctcgag gaagccctct tcttcttggt   4800
gacctcgatc atgtgtacgt ggggactcac gctggccatg gttctctggg gcaagcccat   4860
cggcttggca gttggtatgg gcacttgggc gagaccgcct cgtccgggcc ggacgcaact   4920
cattacctgt ggagccgtgc ttgtgttgag catttctcat ccggcgctgt ttacgatggt   4980
tcctgcactt gtggtcacaa tcatgcgctt tgggttttgg gcgtgcacac tcatggccgg   5040
cgtgcatttg cctgctcgtg ggcgtattct ctttgttgct gcagtcgtgg caatttcttg   5100
tgcgcctact gctctggcgc acttttggc gggggctgtt cttgtggttt cgctcggcgg   5160
ctggcatacg cgaggtcgcg acgacacgct cccgctgtac aagaatgctt gaacggagtc   5220
agagatgctt tttgtccgtg gcgcacgacg agaaaaggcc atagcgttga ttccttttt    5280
agaaatgcat tgaccctgtg tgccagggac catcgttgtc ttctgaccaa cgtccaatt    5340
cctggcctcc ttttttacacg agctgagttg ctgcacatta ttagatcaca ttttgtaatc   5400
acacttgcta catttccttc ttaccctgaa aataatcctc tccagagatg tattgctcgc   5460
tgtcgtcccc ttgtcgtgcg aattcattca tcttctgaac ctaccgtcat ttttccaccg   5520
aggtcttcca ttctcgaaaa gggagcagca tatttaattg cataacctgc actgcaaggc   5580
actgcaacgg aagcgccatg aacgcatgca tgtgcttgat tgaaggaaca tatgcaatac   5640
aataggcaac aaaagattgg ggtggtacag cagatcgttt gagaaatttt gaggtagtat   5700
atatatatat atatatatat atatatatat atatatatac ttttttatcgt cgtaaggacg   5760
cagcgcgaaa ctcgagcagc tgctgccgcc tcgagtcaga ttttttaaagc gcgatatttt   5820
agcacagagt tgcacagact atttggacat acgaaaatcg gggataggga aaaggcatgc   5880
ggggactcca aggcccca                                                 5898
```

<210> SEQ ID NO 2
<211> LENGTH: 3807
<212> TYPE: DNA
<213> ORGANISM: Schizochytrium
<220> FEATURE:
<221> NAME/KEY: CDS
<222> LOCATION: (1)..(3807)

<400> SEQUENCE: 2

```
atg gcg cgc agg gcg tcg cgc ctc ggc gcc gcc gtc gtc gtc ctc         48
Met Ala Arg Arg Ala Ser Arg Leu Gly Ala Ala Val Val Val Leu
1               5                  10                  15 gtc gtc gtc gcc tcc gcc tgc tgc tgg caa gcc gct gcg gac gtc gtg     96
Val Val Val Ala Ser Ala Cys Cys Trp Gln Ala Ala Ala Asp Val Val
            20                  25                  30 gac gcg cag ggc gca aga ggc ccg ggg caa gag agc gac ggc ggc cgc    144
Asp Ala Gln Gly Ala Arg Gly Pro Gly Gln Glu Ser Asp Gly Gly Arg
        35                  40                  45 gcg aag aag cgc atc gcc gtg ctc ggg gcc ggg tac gca ggc ctg tcc    192
Ala Lys Lys Arg Ile Ala Val Leu Gly Ala Gly Tyr Ala Gly Leu Ser
    50                  55                  60 gca gcc tgc gaa ctg agc aga ctg gga cac gag gtc gtg gtt ctc gag    240
Ala Ala Cys Glu Leu Ser Arg Leu Gly His Glu Val Val Val Leu Glu
65                  70                  75                  80 aag aac gcc tac gtg gga ggc cgt gcc cac cag ttc gag gtc gag gcc    288
Lys Asn Ala Tyr Val Gly Gly Arg Ala His Gln Phe Glu Val Glu Ala
                85                  90                  95 gac aat ggg cag acc ttc aag ttc gac gcc ggg ccc agc tgg tac tgg    336
Asp Asn Gly Gln Thr Phe Lys Phe Asp Ala Gly Pro Ser Trp Tyr Trp
            100                 105                 110 atg ccc gag gtc ttt gac cgc ttc ttt gcg cgg tat ggg cga acc gtc    384
Met Pro Glu Val Phe Asp Arg Phe Phe Ala Arg Tyr Gly Arg Thr Val
        115                 120                 125 cag gag ttc tac cag ctc gag cgc ctc gac ccg gca tat cgc atc att    432
Gln Glu Phe Tyr Gln Leu Glu Arg Leu Asp Pro Ala Tyr Arg Ile Ile
    130                 135                 140 cgc aat gac cac aac ggc gag ggt acc gtc gat gtg ccc ggc gct tcg    480
Arg Asn Asp His Asn Gly Glu Gly Thr Val Asp Val Pro Gly Ala Ser
145                 150                 155                 160 agc gag gcc ttc atg tct tgg gca cgc caa ttg aac ggc gat gcc cga    528
Ser Glu Ala Phe Met Ser Trp Ala Arg Gln Leu Asn Gly Asp Ala Arg
                165                 170                 175 ctc gtc gac cgt ctc atg gac gag gcc aag gca aag tac gag gag ggc    576
Leu Val Asp Arg Leu Met Asp Glu Ala Lys Ala Lys Tyr Glu Glu Gly
            180                 185                 190 gtc ttc aag tgg att tgg cat ccc atg gtc tcg tgg tgg gaa atg atc    624
Val Phe Lys Trp Ile Trp His Pro Met Val Ser Trp Trp Glu Met Ile
        195                 200                 205 gat ctc aat ctc gcg cgc gct gcc ttg cag tat gac atg ttc aac agc    672
Asp Leu Asn Leu Ala Arg Ala Ala Leu Gln Tyr Asp Met Phe Asn Ser
    210                 215                 220 ttt gtc gct cac ctg caa aag tac att tca agc gat acc ctg ctc atg    720
Phe Val Ala His Leu Gln Lys Tyr Ile Ser Ser Asp Thr Leu Leu Met
225                 230                 235                 240 att ctc aag tgg ccc gtc atc ttt ctc ggg gcc tcg cct aat ggc gcc    768
Ile Leu Lys Trp Pro Val Ile Phe Leu Gly Ala Ser Pro Asn Gly Ala
                245                 250                 255 cct gcg ttg tat tcc atg atg acc tat ggc ggt cac gcg ctc ggc acc    816
Pro Ala Leu Tyr Ser Met Met Thr Tyr Gly Gly His Ala Leu Gly Thr
            260                 265                 270 ttt tat cca act gga ggc ctc gcg cgg ccc gtc gtt gcc atc gcc gag    864
Phe Tyr Pro Thr Gly Gly Leu Ala Arg Pro Val Val Ala Ile Ala Glu
        275                 280                 285 ctt gcc aga gac ctc ggc gtc gac att cag ctc gat gcc gag gtc acc    912
Leu Ala Arg Asp Leu Gly Val Asp Ile Gln Leu Asp Ala Glu Val Thr
    290                 295                 300 tcg ttt cgc ttt gac gag agc ggc cgt ggt gtt caa gct gtt tgc act    960
Ser Phe Arg Phe Asp Glu Ser Gly Arg Gly Val Gln Ala Val Cys Thr
305                 310                 315                 320
```

```
cgc aac gat cgc tgt gag gct gtc gat ggg gtc gtg gct gcc gcc gat    1008
Arg Asn Asp Arg Cys Glu Ala Val Asp Gly Val Val Ala Ala Ala Asp
            325                 330                 335 tac cac cac gtt gag cag acc ctt ctg ccc ccg gaa ctt cgt cgc tac    1056
Tyr His His Val Glu Gln Thr Leu Leu Pro Pro Glu Leu Arg Arg Tyr
        340                 345                 350 gag cag ggt ttt tgg gat gcc caa gtc atg tcg ccg tcc tgc gtc ctc    1104
Glu Gln Gly Phe Trp Asp Ala Gln Val Met Ser Pro Ser Cys Val Leu
            355                 360                 365 ttc tac ctc ggc ttc gat cac cgc atc caa ggg ctc acc cat cat acg    1152
Phe Tyr Leu Gly Phe Asp His Arg Ile Gln Gly Leu Thr His His Thr
370                 375                 380 ttc ttc ttt gac cga gac ctc gac gct cat ctt cac gcg gcc ttt gac    1200
Phe Phe Phe Asp Arg Asp Leu Asp Ala His Leu His Ala Ala Phe Asp
385                 390                 395                 400 acg cac act tgg gcc gag gaa ccc gtc ttt tac gtg tca gcc acc tcg    1248
Thr His Thr Trp Ala Glu Glu Pro Val Phe Tyr Val Ser Ala Thr Ser
        405                 410                 415 aaa acg gac cca agc gta gtt tct ggt cag ggc gag gcg ctc ttt gtg    1296
Lys Thr Asp Pro Ser Val Val Ser Gly Gln Gly Glu Ala Leu Phe Val
            420                 425                 430 ctc gtt ccc atc tcc tac cag ctc aac ggc aca gac aac gct gcg cgt    1344
Leu Val Pro Ile Ser Tyr Gln Leu Asn Gly Thr Asp Asn Ala Ala Arg
            435                 440                 445 cgg gag caa atc cta cac acc gtg ctc aca cgc atg gaa gag aac ttg    1392
Arg Glu Gln Ile Leu His Thr Val Leu Thr Arg Met Glu Glu Asn Leu
450                 455                 460 aag cag ccc ctc cgc gag tgg ctc gtc tac caa aag tcc tac ggg aca    1440
Lys Gln Pro Leu Arg Glu Trp Leu Val Tyr Gln Lys Ser Tyr Gly Thr
465                 470                 475                 480 acg gat ttt gag cgc gac ttt cac tcc ttt cgt ggc aat gct ttt ggc    1488
Thr Asp Phe Glu Arg Asp Phe His Ser Phe Arg Gly Asn Ala Phe Gly
            485                 490                 495 cac gcc aac acg ctt tcg cag tcg ctc gtg ctc aaa ccc tcc atg gac    1536
His Ala Asn Thr Leu Ser Gln Ser Leu Val Leu Lys Pro Ser Met Asp
            500                 505                 510 tct tta ctc aat aat ctc gtc ttt gct ggc cat ttg acg aat ccc ggc    1584
Ser Leu Leu Asn Asn Leu Val Phe Ala Gly His Leu Thr Asn Pro Gly
            515                 520                 525 cca ggc gtg ccg ccg tcc atc gtc tcg ggc act gtt tcg gcc aac ctg    1632
Pro Gly Val Pro Pro Ser Ile Val Ser Gly Thr Val Ser Ala Asn Leu
530                 535                 540 ttg cat gac aaa atc caa gtg aca gca aat cac cat gca ctg ggg ttc    1680
Leu His Asp Lys Ile Gln Val Thr Ala Asn His His Ala Leu Gly Phe
545                 550                 555                 560 acg ctc ctc gga gct ttc ctt gga gcc ttg tta ctc ggt att ctg gct    1728
Thr Leu Leu Gly Ala Phe Leu Gly Ala Leu Leu Leu Gly Ile Leu Ala
            565                 570                 575 ctc tcg gta ttc tca act cgc ttc gtg tcg tat gtg gag tgc atc aga    1776
Leu Ser Val Phe Ser Thr Arg Phe Val Ser Tyr Val Glu Cys Ile Arg
            580                 585                 590 ctc ttg tat gtg cac ggg cgg act tac ttt gcc gcc gcc acg ctc atg    1824
Leu Leu Tyr Val His Gly Arg Thr Tyr Phe Ala Ala Ala Thr Leu Met
            595                 600                 605 aag ccc atg gcc ttt ctc gac acg gcg gcc atg tac ggg ctt ttt cgc    1872
Lys Pro Met Ala Phe Leu Asp Thr Ala Ala Met Tyr Gly Leu Phe Arg
610                 615                 620 gtt gcc gac gac tac gtc gac aat gtt ggc gac gcc ggc gag cgg cag    1920
Val Ala Asp Asp Tyr Val Asp Asn Val Gly Asp Ala Gly Glu Arg Gln
```

```
                   625                 630                 635                 640
cgg aac ctc gac gcc ttc atg gcg gac ttt tgg cga tgc tgg gaa tcc       1968
Arg Asn Leu Asp Ala Phe Met Ala Asp Phe Trp Arg Cys Trp Glu Ser
                    645                 650                 655 ggc cga ggc gac tac gcg cgc cat ccg acg ctc cct gcc atc atc gag       2016
Gly Arg Gly Asp Tyr Ala Arg His Pro Thr Leu Pro Ala Ile Ile Glu
        660                 665                 670 tcg gcg cac cgt cgt gca tac ccg cgg gaa ctc ttt gag cgt ttc ttc       2064
Ser Ala His Arg Arg Ala Tyr Pro Arg Glu Leu Phe Glu Arg Phe Phe
                675                 680                 685 cgc tcc atg cgg atg gac gcc aaa cga aag gtc gtc tgc ctc acc atg       2112
Arg Ser Met Arg Met Asp Ala Lys Arg Lys Val Val Cys Leu Thr Met
    690                 695                 700 gat gat acg atg gag tac atg gaa ggc agc gcg gct gtc att ggc gag       2160
Asp Asp Thr Met Glu Tyr Met Glu Gly Ser Ala Ala Val Ile Gly Glu
705                 710                 715                 720 ttc atg cta cct att ctc atg ccc gac aga gac tct ttg gct ttc aag       2208
Phe Met Leu Pro Ile Leu Met Pro Asp Arg Asp Ser Leu Ala Phe Lys
                    725                 730                 735 caa gcc gta ccg cac gcg cgc aat ctt gga ctc gct ttc caa atc acc       2256
Gln Ala Val Pro His Ala Arg Asn Leu Gly Leu Ala Phe Gln Ile Thr
        740                 745                 750 aac atg ctt cgg gat att ggc gag gat aat cgc ttg ggt cgc cag tac       2304
Asn Met Leu Arg Asp Ile Gly Glu Asp Asn Arg Leu Gly Arg Gln Tyr
                755                 760                 765 att cct gtc gac gcc tgc aag cgc cat ggt cta aac ggc aag ctc acg       2352
Ile Pro Val Asp Ala Cys Lys Arg His Gly Leu Asn Gly Lys Leu Thr
    770                 775                 780 tct cat gaa cag cct ggc ttt cgc gag ctc atg gag gaa atg ttc gct       2400
Ser His Glu Gln Pro Gly Phe Arg Glu Leu Met Glu Glu Met Phe Ala
785                 790                 795                 800 ttc acc gac aat ctc tat gct agt gct gac ctt ggc atc gac atg ttg       2448
Phe Thr Asp Asn Leu Tyr Ala Ser Ala Asp Leu Gly Ile Asp Met Leu
                    805                 810                 815 cct gag cag gtg cgc gac gtc att cgt gtg gcg cgt ctt gcg tat cac       2496
Pro Glu Gln Val Arg Asp Val Ile Arg Val Ala Arg Leu Ala Tyr His
        820                 825                 830 cgc atc cac gac aag atc cgc gca gcg aat tac gac att ttc acc gct       2544
Arg Ile His Asp Lys Ile Arg Ala Ala Asn Tyr Asp Ile Phe Thr Ala
                835                 840                 845 cga cgt cga gtt ccc ctt gga gaa aag tta acg att ctc gtc gat acc       2592
Arg Arg Arg Val Pro Leu Gly Glu Lys Leu Thr Ile Leu Val Asp Thr
    850                 855                 860 gta ccg cga ctc aag ctc gcc cgc att gcg ctc acc gag ctc att tgt       2640
Val Pro Arg Leu Lys Leu Ala Arg Ile Ala Leu Thr Glu Leu Ile Cys
865                 870                 875                 880 gct aca ctc tat ggt ctt tcg cgc ccg cat att gct ttc gtt tgg att       2688
Ala Thr Leu Tyr Gly Leu Ser Arg Pro His Ile Ala Phe Val Trp Ile
                    885                 890                 895 ggc gcc gta tgg gcg agc tgg ctc gag tgg ccg gga tgc tcg tac ctg       2736
Gly Ala Val Trp Ala Ser Trp Leu Glu Trp Pro Gly Cys Ser Tyr Leu
        900                 905                 910 cgc ttt cac ggg ctc ttc ata cta ccg ccg ctc ctc atg ctc gcc cgt       2784
Arg Phe His Gly Leu Phe Ile Leu Pro Pro Leu Leu Met Leu Ala Arg
                915                 920                 925 ttg gcg cac caa cgc gct gtt gcc gac aag cag gtc ccc ttc ttg cgc       2832
Leu Ala His Gln Arg Ala Val Ala Asp Lys Gln Val Pro Phe Leu Arg
    930                 935                 940 cgc gct ggt ttc tgg act gtg gca ctt gcg tcg gtt gca aca ctt tac       2880
Arg Ala Gly Phe Trp Thr Val Ala Leu Ala Ser Val Ala Thr Leu Tyr
```

```
Arg Ala Gly Phe Trp Thr Val Ala Leu Cys Val Val Ala Thr Leu Tyr
945                 950                 955                 960 acc aca cca tgg gac aat ttt ctc gtg tat cgc cgc gtc tgg gga tac       2928
Thr Thr Pro Trp Asp Asn Phe Leu Val Tyr Arg Arg Val Trp Gly Tyr
                    965                 970                 975 ccg ccg gag cgc att ctc ttt gtc att ggg tat gtg ccc att gaa gag       2976
Pro Pro Glu Arg Ile Leu Phe Val Ile Gly Tyr Val Pro Ile Glu Glu
                980                 985                 990 tac atg ttc ttc acg ctc gaa acc atg ttg gtc gcg gcg gtc tgg cta       3024
Tyr Met Phe Phe Thr Leu Glu Thr Met Leu Val Ala Ala Val Trp Leu
            995                 1000                1005 cag gtt ttt cag ccc acg acg ttg cag gcc gag gta ggc cca cgt           3069
Gln Val Phe Gln Pro Thr Thr Leu Gln Ala Glu Val Gly Pro Arg
    1010                1015                1020 gga aag ggg ggc atg ctc gtt ctc gcg agt ctt gga ctc gtc tgg           3114
Gly Lys Gly Gly Met Leu Val Leu Ala Ser Leu Gly Leu Val Trp
1025                1030                1035 gtt gcc ggc ctt tcg tgt ttg gcc tcg gag caa agc tta tac att           3159
Val Ala Gly Leu Ser Cys Leu Ala Ser Glu Gln Ser Leu Tyr Ile
    1040                1045                1050 ggt ctc att ctc agc tgg tct atg ccc gtc ctc att ctg caa tgg           3204
Gly Leu Ile Leu Ser Trp Ser Met Pro Val Leu Ile Leu Gln Trp
1055                1060                1065 agt ctc ggt gca cat gtg ctc act acg cat gca aag ccg gtc ctg           3249
Ser Leu Gly Ala His Val Leu Thr Thr His Ala Lys Pro Val Leu
    1070                1075                1080 acg acg atc gtg tcg gcc aca gcg tac ctt tgc gtg gcc gac gaa           3294
Thr Thr Ile Val Ser Ala Thr Ala Tyr Leu Cys Val Ala Asp Glu
1085                1090                1095 tgg gcg att cgt cac ggc atc tgg cgc atc aat cct gca aat ctt           3339
Trp Ala Ile Arg His Gly Ile Trp Arg Ile Asn Pro Ala Asn Leu
    1100                1105                1110 gtg ttg ccc atg ggc aaa cat gca ctt ccc ctc gag gaa gcc ctc           3384
Val Leu Pro Met Gly Lys His Ala Leu Pro Leu Glu Glu Ala Leu
1115                1120                1125 ttc ttc ttg gtg acc tcg atc atg tgt acg tgg gga ctc acg ctg           3429
Phe Phe Leu Val Thr Ser Ile Met Cys Thr Trp Gly Leu Thr Leu
    1130                1135                1140 gcc atg gtt ctc tgg ggc aag ccc atc ggc ttg gca gtt ggt atg           3474
Ala Met Val Leu Trp Gly Lys Pro Ile Gly Leu Ala Val Gly Met
1145                1150                1155 ggc act tgg gcg aga ccg cct cgt ccg ggc cgg acg caa ctc att           3519
Gly Thr Trp Ala Arg Pro Pro Arg Pro Gly Arg Thr Gln Leu Ile
    1160                1165                1170 acc tgt gga gcc gtg ctt gtg ttg agc att tct cat ccg gcg ctg           3564
Thr Cys Gly Ala Val Leu Val Leu Ser Ile Ser His Pro Ala Leu
1175                1180                1185 ttt acg atg gtt cct gca ctt gtg gtc aca atc atg cgc ttt ggg           3609
Phe Thr Met Val Pro Ala Leu Val Val Thr Ile Met Arg Phe Gly
    1190                1195                1200 ttt tgg gcg tgc aca ctc atg gcc ggc gtg cat ttg cct gct cgt           3654
Phe Trp Ala Cys Thr Leu Met Ala Gly Val His Leu Pro Ala Arg
1205                1210                1215 ggg cgt att ctc ttt gtt gct gca gtc gtg gca att tct tgt gcg           3699
Gly Arg Ile Leu Phe Val Ala Ala Val Val Ala Ile Ser Cys Ala
    1220                1225                1230 cct act gct ctg gcg cca ctt ttg gcg ggg gct gtt ctt gtg gtt           3744
Pro Thr Ala Leu Ala Pro Leu Leu Ala Gly Ala Val Leu Val Val
1235                1240                1245
```

```
tcg ctc ggc ggc tgg cat acg cga ggt cgc gac gac acg ctc ccg    3789
Ser Leu Gly Gly Trp His Thr Arg Gly Arg Asp Asp Thr Leu Pro
    1250                1255                1260 ctg tac aag aat gct tga                                         3807
Leu Tyr Lys Asn Ala
    1265
```

<210> SEQ ID NO 3
<211> LENGTH: 1268
<212> TYPE: PRT
<213> ORGANISM: Schizochytrium

<400> SEQUENCE: 3

```
Met Ala Arg Arg Ala Ser Arg Leu Gly Ala Val Val Val Leu
1               5                   10                  15

Val Val Val Ala Ser Ala Cys Cys Trp Gln Ala Ala Asp Val Val
            20                  25                  30

Asp Ala Gln Gly Ala Arg Gly Pro Gly Gln Glu Ser Asp Gly Gly Arg
        35                  40                  45

Ala Lys Lys Arg Ile Ala Val Leu Gly Ala Gly Tyr Ala Gly Leu Ser
    50                  55                  60

Ala Ala Cys Glu Leu Ser Arg Leu Gly His Glu Val Val Leu Glu
65                  70                  75                  80

Lys Asn Ala Tyr Val Gly Gly Arg Ala His Gln Phe Glu Val Glu Ala
                85                  90                  95

Asp Asn Gly Gln Thr Phe Lys Phe Asp Ala Gly Pro Ser Trp Tyr Trp
            100                 105                 110

Met Pro Glu Val Phe Asp Arg Phe Phe Ala Arg Tyr Gly Arg Thr Val
        115                 120                 125

Gln Glu Phe Tyr Gln Leu Glu Arg Leu Asp Pro Ala Tyr Arg Ile Ile
    130                 135                 140

Arg Asn Asp His Asn Gly Glu Gly Thr Val Asp Val Pro Gly Ala Ser
145                 150                 155                 160

Ser Glu Ala Phe Met Ser Trp Ala Arg Gln Leu Asn Gly Asp Ala Arg
                165                 170                 175

Leu Val Asp Arg Leu Met Asp Glu Ala Lys Ala Lys Tyr Glu Glu Gly
            180                 185                 190

Val Phe Lys Trp Ile Trp His Pro Met Val Ser Trp Trp Glu Met Ile
        195                 200                 205

Asp Leu Asn Leu Ala Arg Ala Ala Leu Gln Tyr Asp Met Phe Asn Ser
    210                 215                 220

Phe Val Ala His Leu Gln Lys Tyr Ile Ser Ser Asp Thr Leu Leu Met
225                 230                 235                 240

Ile Leu Lys Trp Pro Val Ile Phe Leu Gly Ala Ser Pro Asn Gly Ala
                245                 250                 255

Pro Ala Leu Tyr Ser Met Met Thr Tyr Gly Gly His Ala Leu Gly Thr
            260                 265                 270

Phe Tyr Pro Thr Gly Gly Leu Ala Arg Pro Val Val Ala Ile Ala Glu
        275                 280                 285

Leu Ala Arg Asp Leu Gly Val Asp Ile Gln Leu Asp Ala Glu Val Thr
    290                 295                 300

Ser Phe Arg Phe Asp Glu Ser Gly Arg Val Gln Ala Val Cys Thr
305                 310                 315                 320

Arg Asn Asp Arg Cys Glu Ala Val Asp Gly Val Val Ala Ala Ala Asp
                325                 330                 335
```

```
Tyr His His Val Glu Gln Thr Leu Leu Pro Pro Glu Leu Arg Arg Tyr
            340                 345                 350

Glu Gln Gly Phe Trp Asp Ala Gln Val Met Ser Pro Ser Cys Val Leu
        355                 360                 365

Phe Tyr Leu Gly Phe Asp His Arg Ile Gln Gly Leu Thr His His Thr
    370                 375                 380

Phe Phe Phe Asp Arg Asp Leu Asp Ala His Leu His Ala Ala Phe Asp
385                 390                 395                 400

Thr His Thr Trp Ala Glu Pro Val Phe Tyr Val Ser Ala Thr Ser
                405                 410                 415

Lys Thr Asp Pro Ser Val Val Ser Gly Gln Gly Glu Ala Leu Phe Val
                420                 425                 430

Leu Val Pro Ile Ser Tyr Gln Leu Asn Gly Thr Asp Asn Ala Ala Arg
                435                 440                 445

Arg Glu Gln Ile Leu His Thr Val Leu Thr Arg Met Glu Glu Asn Leu
        450                 455                 460

Lys Gln Pro Leu Arg Glu Trp Leu Val Tyr Gln Lys Ser Tyr Gly Thr
465                 470                 475                 480

Thr Asp Phe Glu Arg Asp Phe His Ser Phe Arg Gly Asn Ala Phe Gly
                485                 490                 495

His Ala Asn Thr Leu Ser Gln Ser Leu Val Leu Lys Pro Ser Met Asp
            500                 505                 510

Ser Leu Leu Asn Asn Leu Val Phe Ala Gly His Leu Thr Asn Pro Gly
        515                 520                 525

Pro Gly Val Pro Pro Ser Ile Val Ser Gly Thr Val Ser Ala Asn Leu
        530                 535                 540

Leu His Asp Lys Ile Gln Val Thr Ala Asn His His Ala Leu Gly Phe
545                 550                 555                 560

Thr Leu Leu Gly Ala Phe Leu Gly Ala Leu Leu Leu Gly Ile Leu Ala
                565                 570                 575

Leu Ser Val Phe Ser Thr Arg Phe Val Ser Tyr Val Glu Cys Ile Arg
            580                 585                 590

Leu Leu Tyr Val His Gly Arg Thr Tyr Phe Ala Ala Thr Leu Met
        595                 600                 605

Lys Pro Met Ala Phe Leu Asp Thr Ala Ala Met Tyr Gly Leu Phe Arg
        610                 615                 620

Val Ala Asp Asp Tyr Val Asp Asn Val Gly Asp Ala Gly Glu Arg Gln
625                 630                 635                 640

Arg Asn Leu Asp Ala Phe Met Ala Asp Phe Trp Arg Cys Trp Glu Ser
                645                 650                 655

Gly Arg Gly Asp Tyr Ala Arg His Pro Thr Leu Pro Ala Ile Ile Glu
            660                 665                 670

Ser Ala His Arg Arg Ala Tyr Pro Arg Glu Leu Phe Glu Arg Phe
            675                 680                 685

Arg Ser Met Arg Met Asp Ala Lys Arg Lys Val Val Cys Leu Thr Met
        690                 695                 700

Asp Asp Thr Met Glu Tyr Met Glu Gly Ser Ala Val Ile Gly Glu
705                 710                 715                 720

Phe Met Leu Pro Ile Leu Met Pro Asp Arg Asp Ser Leu Ala Phe Lys
                725                 730                 735

Gln Ala Val Pro His Ala Arg Asn Leu Gly Leu Ala Phe Gln Ile Thr
                740                 745                 750

Asn Met Leu Arg Asp Ile Gly Glu Asp Asn Arg Leu Gly Arg Gln Tyr
```

-continued

```
            755                 760                 765
Ile Pro Val Asp Ala Cys Lys Arg His Gly Leu Asn Gly Lys Leu Thr
770                 775                 780

Ser His Glu Gln Pro Gly Phe Arg Glu Leu Met Glu Glu Met Phe Ala
785                 790                 795                 800

Phe Thr Asp Asn Leu Tyr Ala Ser Ala Asp Leu Gly Ile Asp Met Leu
                805                 810                 815

Pro Glu Gln Val Arg Asp Val Ile Arg Val Ala Arg Leu Ala Tyr His
                820                 825                 830

Arg Ile His Asp Lys Ile Arg Ala Ala Asn Tyr Asp Ile Phe Thr Ala
                835                 840                 845

Arg Arg Arg Val Pro Leu Gly Glu Lys Leu Thr Ile Leu Val Asp Thr
850                 855                 860

Val Pro Arg Leu Lys Leu Ala Arg Ile Ala Leu Thr Glu Leu Ile Cys
865                 870                 875                 880

Ala Thr Leu Tyr Gly Leu Ser Arg Pro His Ile Ala Phe Val Trp Ile
                885                 890                 895

Gly Ala Val Trp Ala Ser Trp Leu Glu Trp Pro Gly Cys Ser Tyr Leu
                900                 905                 910

Arg Phe His Gly Leu Phe Ile Leu Pro Pro Leu Leu Met Leu Ala Arg
                915                 920                 925

Leu Ala His Gln Arg Ala Val Ala Asp Lys Gln Val Pro Phe Leu Arg
                930                 935                 940

Arg Ala Gly Phe Trp Thr Val Ala Leu Cys Val Val Ala Thr Leu Tyr
945                 950                 955                 960

Thr Thr Pro Trp Asp Asn Phe Leu Val Tyr Arg Arg Val Trp Gly Tyr
                965                 970                 975

Pro Pro Glu Arg Ile Leu Phe Val Ile Gly Tyr Val Pro Ile Glu Glu
                980                 985                 990

Tyr Met Phe Phe Thr Leu Glu Thr  Met Leu Val Ala Ala  Val Trp Leu
                995                1000                1005

Gln Val  Phe Gln Pro Thr Thr  Leu Gln Ala Glu Val  Gly Pro Arg
1010                1015                1020

Gly Lys  Gly Gly Met Leu Val  Leu Ala Ser Leu Gly  Leu Val Trp
1025                1030                1035

Val Ala  Gly Leu Ser Cys Leu  Ala Ser Glu Gln Ser  Leu Tyr Ile
1040                1045                1050

Gly Leu  Ile Leu Ser Trp Ser  Met Pro Val Leu Ile  Leu Gln Trp
1055                1060                1065

Ser Leu  Gly Ala His Val Leu  Thr Thr His Ala Lys  Pro Val Leu
1070                1075                1080

Thr Thr  Ile Val Ser Ala Thr  Ala Tyr Leu Cys Val  Ala Asp Glu
1085                1090                1095

Trp Ala  Ile Arg His Gly Ile  Trp Arg Ile Asn Pro  Ala Asn Leu
1100                1105                1110

Val Leu  Pro Met Gly Lys His  Ala Leu Pro Leu Glu  Glu Ala Leu
1115                1120                1125

Phe Phe  Leu Val Thr Ser Ile  Met Cys Thr Trp Gly  Leu Thr Leu
1130                1135                1140

Ala Met  Val Leu Trp Gly Lys  Pro Ile Gly Leu Ala  Val Gly Met
1145                1150                1155

Gly Thr  Trp Ala Arg Pro Pro  Arg Pro Gly Arg Thr  Gln Leu Ile
1160                1165                1170
```

```
Thr Cys Gly Ala Val Leu Val  Leu Ser Ile Ser His  Pro Ala Leu
    1175             1180              1185

Phe Thr Met Val Pro Ala Leu  Val Val Thr Ile Met  Arg Phe Gly
    1190             1195              1200

Phe Trp Ala Cys Thr Leu Met  Ala Gly Val His Leu  Pro Ala Arg
    1205             1210              1215

Gly Arg Ile Leu Phe Val Ala  Ala Val Val Ala Ile  Ser Cys Ala
    1220             1225              1230

Pro Thr Ala Leu Ala Pro Leu  Leu Ala Gly Ala Val  Leu Val Val
    1235             1240              1245

Ser Leu Gly Gly Trp His Thr  Arg Gly Arg Asp Asp  Thr Leu Pro
    1250             1255              1260

Leu Tyr Lys Asn Ala
    1265

<210> SEQ ID NO 4
<211> LENGTH: 1407
<212> TYPE: DNA
<213> ORGANISM: Schizochytrium
<220> FEATURE:
<221> NAME/KEY: CDS
<222> LOCATION: (1)..(1407)

<400> SEQUENCE: 4
```

| | | |
|---|---|---|
| atc gcc gtg ctc ggg gcc ggg tac gca ggc ctg tcc gca gcc tgc gaa<br>Ile Ala Val Leu Gly Ala Gly Tyr Ala Gly Leu Ser Ala Ala Cys Glu<br>1               5                   10                  15 | | 48 |
| ctg agc aga ctg gga cac gag gtc gtg gtt ctc gag aag aac gcc tac<br>Leu Ser Arg Leu Gly His Glu Val Val Val Leu Glu Lys Asn Ala Tyr<br>            20                  25                  30 | | 96 |
| gtg gga ggc cgt gcc cac cag ttc gag gtc gag gcc gac aat ggg cag<br>Val Gly Gly Arg Ala His Gln Phe Glu Val Glu Ala Asp Asn Gly Gln<br>        35                  40                  45 | | 144 |
| acc ttc aag ttc gac gcc ggg ccc agc tgg tac tgg atg ccc gag gtc<br>Thr Phe Lys Phe Asp Ala Gly Pro Ser Trp Tyr Trp Met Pro Glu Val<br>    50                  55                  60 | | 192 |
| ttt gac cgc ttc ttt gcg cgg tat ggg cga acc gtc cag gag ttc tac<br>Phe Asp Arg Phe Phe Ala Arg Tyr Gly Arg Thr Val Gln Glu Phe Tyr<br>65                  70                  75                  80 | | 240 |
| cag ctc gag cgc ctc gac ccg gca tat cgc atc att cgc aat gac cac<br>Gln Leu Glu Arg Leu Asp Pro Ala Tyr Arg Ile Ile Arg Asn Asp His<br>                85                  90                  95 | | 288 |
| aac ggc gag ggt acc gtc gat gtg ccc ggc gct tcg agc gag gcc ttc<br>Asn Gly Glu Gly Thr Val Asp Val Pro Gly Ala Ser Ser Glu Ala Phe<br>            100                 105                 110 | | 336 |
| atg tct tgg gca cgc caa ttg aac ggc gat gcc cga ctc gtc gac cgt<br>Met Ser Trp Ala Arg Gln Leu Asn Gly Asp Ala Arg Leu Val Asp Arg<br>        115                 120                 125 | | 384 |
| ctc atg gac gag gcc aag gca aag tac gag gag ggc gtc ttc aag tgg<br>Leu Met Asp Glu Ala Lys Ala Lys Tyr Glu Glu Gly Val Phe Lys Trp<br>    130                 135                 140 | | 432 |
| att tgg cat ccc atg gtc tcg tgg tgg gaa atg atc gat ctc aat ctc<br>Ile Trp His Pro Met Val Ser Trp Trp Glu Met Ile Asp Leu Asn Leu<br>145                 150                 155                 160 | | 480 |
| gcg cgc gct gcc ttg cag tat gac atg ttc aac agc ttt gtc gct cac<br>Ala Arg Ala Ala Leu Gln Tyr Asp Met Phe Asn Ser Phe Val Ala His<br>                165                 170                 175 | | 528 |
| ctg caa aag tac att tca agc gat acc ctg ctc atg att ctc aag tgg<br>Leu Gln Lys Tyr Ile Ser Ser Asp Thr Leu Leu Met Ile Leu Lys Trp | | 576 |

```
                180                185                190
ccc gtc atc ttt ctc ggg gcc tcg cct aat ggc gcc cct gcg ttg tat        624
Pro Val Ile Phe Leu Gly Ala Ser Pro Asn Gly Ala Pro Ala Leu Tyr
        195                200                205 tcc atg atg acc tat ggc ggt cac gcg ctc ggc acc ttt tat cca act        672
Ser Met Met Thr Tyr Gly Gly His Ala Leu Gly Thr Phe Tyr Pro Thr
210                215                220 gga ggc ctc gcg cgg ccc gtc gtt gcc atc gcc gag ctt gcc aga gac        720
Gly Gly Leu Ala Arg Pro Val Val Ala Ile Ala Glu Leu Ala Arg Asp
225                230                235                240 ctc ggc gtc gac att cag ctc gat gcc gag gtc acc tcg ttt cgc ttt        768
Leu Gly Val Asp Ile Gln Leu Asp Ala Glu Val Thr Ser Phe Arg Phe
            245                250                255 gac gag agc ggc cgt ggt gtt caa gct gtt tgc act cgc aac gat cgc        816
Asp Glu Ser Gly Arg Gly Val Gln Ala Val Cys Thr Arg Asn Asp Arg
        260                265                270 tgt gag gct gtc gat ggg gtc gtg gct gcc gcc gat tac cac cac gtt        864
Cys Glu Ala Val Asp Gly Val Val Ala Ala Ala Asp Tyr His His Val
    275                280                285 gag cag acc ctt ctg ccc ccg gaa ctt cgt cgc tac gag cag ggt ttt        912
Glu Gln Thr Leu Leu Pro Pro Glu Leu Arg Arg Tyr Glu Gln Gly Phe
290                295                300 tgg gat gcc caa gtc atg tcg ccg tcc tgc gtc ctc ttc tac ctc ggc        960
Trp Asp Ala Gln Val Met Ser Pro Ser Cys Val Leu Phe Tyr Leu Gly
305                310                315                320 ttc gat cac cgc atc caa ggg ctc acc cat cat acg ttc ttc ttt gac       1008
Phe Asp His Arg Ile Gln Gly Leu Thr His His Thr Phe Phe Phe Asp
            325                330                335 cga gac ctc gac gct cat ctt cac gcg gcc ttt gac acg cac act tgg       1056
Arg Asp Leu Asp Ala His Leu His Ala Ala Phe Asp Thr His Thr Trp
        340                345                350 gcc gag gaa ccc gtc ttt tac gtg tca gcc acc tcg aaa acg gac cca       1104
Ala Glu Glu Pro Val Phe Tyr Val Ser Ala Thr Ser Lys Thr Asp Pro
    355                360                365 agc gta gtt tct ggt cag ggc gag gcg ctc ttt gtg ctc gtt ccc atc       1152
Ser Val Val Ser Gly Gln Gly Glu Ala Leu Phe Val Leu Val Pro Ile
370                375                380 tcc tac cag ctc aac ggc aca gac aac gct gcg cgt cgg gag caa atc       1200
Ser Tyr Gln Leu Asn Gly Thr Asp Asn Ala Ala Arg Arg Glu Gln Ile
385                390                395                400 cta cac acc gtg ctc aca cgc atg gaa gag aac ttg aag cag ccc ctc       1248
Leu His Thr Val Leu Thr Arg Met Glu Glu Asn Leu Lys Gln Pro Leu
            405                410                415 cgc gag tgg ctc gtc tac caa aag tcc tac ggg aca acg gat ttt gag       1296
Arg Glu Trp Leu Val Tyr Gln Lys Ser Tyr Gly Thr Thr Asp Phe Glu
        420                425                430 cgc gac ttt cac tcc ttt cgt ggc aat gct ttt ggc cac gcc aac acg       1344
Arg Asp Phe His Ser Phe Arg Gly Asn Ala Phe Gly His Ala Asn Thr
    435                440                445 ctt tcg cag tcg ctc gtg ctc aaa ccc tcc atg gac tct tta ctc aat       1392
Leu Ser Gln Ser Leu Val Leu Lys Pro Ser Met Asp Ser Leu Leu Asn
450                455                460 aat ctc gtc ttt gct                                                    1407
Asn Leu Val Phe Ala
465

<210> SEQ ID NO 5
<211> LENGTH: 469
<212> TYPE: PRT
<213> ORGANISM: Schizochytrium
```

```
<400> SEQUENCE: 5

Ile Ala Val Leu Gly Ala Gly Tyr Ala Gly Leu Ser Ala Ala Cys Glu
1               5                   10                  15

Leu Ser Arg Leu Gly His Glu Val Val Leu Glu Lys Asn Ala Tyr
            20                  25                  30

Val Gly Gly Arg Ala His Gln Phe Glu Val Glu Ala Asp Asn Gly Gln
        35                  40                  45

Thr Phe Lys Phe Asp Ala Gly Pro Ser Trp Tyr Trp Met Pro Glu Val
    50                  55                  60

Phe Asp Arg Phe Phe Ala Arg Tyr Gly Arg Thr Val Gln Glu Phe Tyr
65                  70                  75                  80

Gln Leu Glu Arg Leu Asp Pro Ala Tyr Arg Ile Ile Arg Asn Asp His
                85                  90                  95

Asn Gly Glu Gly Thr Val Asp Val Pro Gly Ala Ser Ser Glu Ala Phe
            100                 105                 110

Met Ser Trp Ala Arg Gln Leu Asn Gly Asp Ala Arg Leu Val Asp Arg
        115                 120                 125

Leu Met Asp Glu Ala Lys Ala Lys Tyr Glu Glu Gly Val Phe Lys Trp
130                 135                 140

Ile Trp His Pro Met Val Ser Trp Trp Glu Met Ile Asp Leu Asn Leu
145                 150                 155                 160

Ala Arg Ala Ala Leu Gln Tyr Asp Met Phe Asn Ser Phe Val Ala His
                165                 170                 175

Leu Gln Lys Tyr Ile Ser Ser Asp Thr Leu Leu Met Ile Leu Lys Trp
            180                 185                 190

Pro Val Ile Phe Leu Gly Ala Ser Pro Asn Gly Ala Pro Ala Leu Tyr
        195                 200                 205

Ser Met Met Thr Tyr Gly Gly His Ala Leu Gly Thr Phe Tyr Pro Thr
    210                 215                 220

Gly Gly Leu Ala Arg Pro Val Val Ala Ile Ala Glu Leu Ala Arg Asp
225                 230                 235                 240

Leu Gly Val Asp Ile Gln Leu Asp Ala Glu Val Thr Ser Phe Arg Phe
                245                 250                 255

Asp Glu Ser Gly Arg Gly Val Gln Ala Val Cys Thr Arg Asn Asp Arg
            260                 265                 270

Cys Glu Ala Val Asp Gly Val Val Ala Ala Asp Tyr His His Val
        275                 280                 285

Glu Gln Thr Leu Leu Pro Pro Glu Leu Arg Arg Tyr Glu Gln Gly Phe
    290                 295                 300

Trp Asp Ala Gln Val Met Ser Pro Ser Cys Val Leu Phe Tyr Leu Gly
305                 310                 315                 320

Phe Asp His Arg Ile Gln Gly Leu Thr His His Thr Phe Phe Asp
                325                 330                 335

Arg Asp Leu Asp Ala His Leu His Ala Ala Phe Asp Thr His Thr Trp
            340                 345                 350

Ala Glu Glu Pro Val Phe Tyr Val Ser Ala Thr Ser Lys Thr Asp Pro
        355                 360                 365

Ser Val Val Ser Gly Gln Gly Glu Ala Leu Phe Val Leu Val Pro Ile
    370                 375                 380

Ser Tyr Gln Leu Asn Gly Thr Asp Asn Ala Ala Arg Arg Glu Gln Ile
385                 390                 395                 400

Leu His Thr Val Leu Thr Arg Met Glu Glu Asn Leu Lys Gln Pro Leu
```

-continued

```
                       405                 410                 415
Arg Glu Trp Leu Val Tyr Gln Lys Ser Tyr Gly Thr Thr Asp Phe Glu
            420                 425                 430

Arg Asp Phe His Ser Phe Arg Gly Asn Ala Phe Gly His Ala Asn Thr
            435                 440                 445

Leu Ser Gln Ser Leu Val Leu Lys Pro Ser Met Asp Ser Leu Leu Asn
            450                 455                 460

Asn Leu Val Phe Ala
465

<210> SEQ ID NO 6
<211> LENGTH: 825
<212> TYPE: DNA
<213> ORGANISM: Schizochytrium
<220> FEATURE:
<221> NAME/KEY: CDS
<222> LOCATION: (1)..(825)

<400> SEQUENCE: 6 tcg tat gtg gag tgc atc aga ctc ttg tat gtg cac ggg cgg act tac      48
Ser Tyr Val Glu Cys Ile Arg Leu Leu Tyr Val His Gly Arg Thr Tyr
 1               5                  10                  15 ttt gcc gcc gcc acg ctc atg aag ccc atg gcc ttt ctc gac acg gcg      96
Phe Ala Ala Ala Thr Leu Met Lys Pro Met Ala Phe Leu Asp Thr Ala
                20                  25                  30 gcc atg tac ggg ctt ttt cgc gtt gcc gac gac tac gtc gac aat gtt     144
Ala Met Tyr Gly Leu Phe Arg Val Ala Asp Asp Tyr Val Asp Asn Val
            35                  40                  45 ggc gac gcc ggc gag cgg cag cgg aac ctc gac gcc ttc atg gcg gac     192
Gly Asp Ala Gly Glu Arg Gln Arg Asn Leu Asp Ala Phe Met Ala Asp
        50                  55                  60 ttt tgg cga tgc tgg gaa tcc ggc cga ggc gac tac gcg cgc cat ccg     240
Phe Trp Arg Cys Trp Glu Ser Gly Arg Gly Asp Tyr Ala Arg His Pro
65                  70                  75                  80 acg ctc cct gcc atc atc gag tcg gcg cac cgt cgt gca tac ccg cgg     288
Thr Leu Pro Ala Ile Ile Glu Ser Ala His Arg Arg Ala Tyr Pro Arg
                85                  90                  95 gaa ctc ttt gag cgt ttc ttc cgc tcc atg cgg atg gac gcc aaa cga     336
Glu Leu Phe Glu Arg Phe Phe Arg Ser Met Arg Met Asp Ala Lys Arg
                100                 105                 110 aag gtc gtc tgc ctc acc atg gat gat acg atg gag tac atg gaa ggc     384
Lys Val Val Cys Leu Thr Met Asp Asp Thr Met Glu Tyr Met Glu Gly
            115                 120                 125 agc gcg gct gtc att ggc gag ttc atg cta cct att ctc atg ccc gac     432
Ser Ala Ala Val Ile Gly Glu Phe Met Leu Pro Ile Leu Met Pro Asp
        130                 135                 140 aga gac tct ttg gct ttc aag caa gcc gta ccg cac gcg cgc aat ctt     480
Arg Asp Ser Leu Ala Phe Lys Gln Ala Val Pro His Ala Arg Asn Leu
145                 150                 155                 160 gga ctc gct ttc caa atc acc aac atg ctt cgg gat att ggc gag gat     528
Gly Leu Ala Phe Gln Ile Thr Asn Met Leu Arg Asp Ile Gly Glu Asp
                165                 170                 175 aat cgc ttg ggt cgc cag tac att cct gtc gac gcc tgc aag cgc cat     576
Asn Arg Leu Gly Arg Gln Tyr Ile Pro Val Asp Ala Cys Lys Arg His
            180                 185                 190 ggt cta aac ggc aag ctc acg tct cat gaa cag cct ggc ttt cgc gag     624
Gly Leu Asn Gly Lys Leu Thr Ser His Glu Gln Pro Gly Phe Arg Glu
        195                 200                 205 ctc atg gag gaa atg ttc gct ttc acc gac aat ctc tat gct agt gct     672
Leu Met Glu Glu Met Phe Ala Phe Thr Asp Asn Leu Tyr Ala Ser Ala
```

```
                210                 215                 220
gac ctt ggc atc gac atg ttg cct gag cag gtg cgc gac gtc att cgt       720
Asp Leu Gly Ile Asp Met Leu Pro Glu Gln Val Arg Asp Val Ile Arg
225                 230                 235                 240 gtg gcg cgt ctt gcg tat cac cgc atc cac gac aag atc cgc gca gcg       768
Val Ala Arg Leu Ala Tyr His Arg Ile His Asp Lys Ile Arg Ala Ala
                245                 250                 255 aat tac gac att ttc acc gct cga cgt cga gtt ccc ctt gga gaa aag       816
Asn Tyr Asp Ile Phe Thr Ala Arg Arg Arg Val Pro Leu Gly Glu Lys
            260                 265                 270 tta acg att                                                           825
Leu Thr Ile
        275

<210> SEQ ID NO 7
<211> LENGTH: 275
<212> TYPE: PRT
<213> ORGANISM: Schizochytrium

<400> SEQUENCE: 7

Ser Tyr Val Glu Cys Ile Arg Leu Leu Tyr Val His Gly Arg Thr Tyr
1               5                   10                  15

Phe Ala Ala Thr Leu Met Lys Pro Met Ala Phe Leu Asp Thr Ala
            20                  25                  30

Ala Met Tyr Gly Leu Phe Arg Val Ala Asp Asp Tyr Val Asp Asn Val
        35                  40                  45

Gly Asp Ala Gly Glu Arg Gln Arg Asn Leu Asp Ala Phe Met Ala Asp
    50                  55                  60

Phe Trp Arg Cys Trp Glu Ser Gly Arg Gly Asp Tyr Ala Arg His Pro
65                  70                  75                  80

Thr Leu Pro Ala Ile Ile Glu Ser Ala His Arg Arg Ala Tyr Pro Arg
                85                  90                  95

Glu Leu Phe Glu Arg Phe Arg Ser Met Arg Met Asp Ala Lys Arg
            100                 105                 110

Lys Val Val Cys Leu Thr Met Asp Asp Thr Met Glu Tyr Met Glu Gly
        115                 120                 125

Ser Ala Ala Val Ile Gly Glu Phe Met Leu Pro Ile Leu Met Pro Asp
    130                 135                 140

Arg Asp Ser Leu Ala Phe Lys Gln Ala Val Pro His Ala Arg Asn Leu
145                 150                 155                 160

Gly Leu Ala Phe Gln Ile Thr Asn Met Leu Arg Asp Ile Gly Glu Asp
                165                 170                 175

Asn Arg Leu Gly Arg Gln Tyr Ile Pro Val Asp Ala Cys Lys Arg His
            180                 185                 190

Gly Leu Asn Gly Lys Leu Thr Ser His Glu Gln Pro Gly Phe Arg Glu
        195                 200                 205

Leu Met Glu Glu Met Phe Ala Phe Thr Asp Asn Leu Tyr Ala Ser Ala
    210                 215                 220

Asp Leu Gly Ile Asp Met Leu Pro Glu Gln Val Arg Asp Val Ile Arg
225                 230                 235                 240

Val Ala Arg Leu Ala Tyr His Arg Ile His Asp Lys Ile Arg Ala Ala
                245                 250                 255

Asn Tyr Asp Ile Phe Thr Ala Arg Arg Arg Val Pro Leu Gly Glu Lys
            260                 265                 270

Leu Thr Ile
        275
```

```
<210> SEQ ID NO 8
<211> LENGTH: 666
<212> TYPE: DNA
<213> ORGANISM: Schizochytrium
<220> FEATURE:
<221> NAME/KEY: CDS
<222> LOCATION: (1)..(666)

<400> SEQUENCE: 8 tac ctg cgc ttt cac ggg ctc ttc ata cta ccg ccg ctc ctc atg ctc      48
Tyr Leu Arg Phe His Gly Leu Phe Ile Leu Pro Pro Leu Leu Met Leu
1               5                   10                  15 gcc cgt ttg gcg cac caa cgc gct gtt gcc gac aag cag gtc ccc ttc      96
Ala Arg Leu Ala His Gln Arg Ala Val Ala Asp Lys Gln Val Pro Phe
            20                  25                  30 ttg cgc cgc gct ggt ttc tgg act gtg gca ctt tgc gtc gtt gca aca     144
Leu Arg Arg Ala Gly Phe Trp Thr Val Ala Leu Cys Val Val Ala Thr
        35                  40                  45 ctt tac acc aca cca tgg gac aat ttt ctc gtg tat cgc cgc gtc tgg     192
Leu Tyr Thr Thr Pro Trp Asp Asn Phe Leu Val Tyr Arg Arg Val Trp
    50                  55                  60 gga tac ccg ccg gag cgc att ctc ttt gtc att ggg tat gtg ccc att     240
Gly Tyr Pro Pro Glu Arg Ile Leu Phe Val Ile Gly Tyr Val Pro Ile
65                  70                  75                  80 gaa gag tac atg ttc ttc acg ctc gaa acc atg ttg gtc gcg gcg gtc     288
Glu Glu Tyr Met Phe Phe Thr Leu Glu Thr Met Leu Val Ala Ala Val
                85                  90                  95 tgg cta cag gtt ttt cag ccc acg acg ttg cag gcc gag gta ggc cca     336
Trp Leu Gln Val Phe Gln Pro Thr Thr Leu Gln Ala Glu Val Gly Pro
            100                 105                 110 cgt gga aag ggg ggc atg ctc gtt ctc gcg agt ctt gga ctc gtc tgg     384
Arg Gly Lys Gly Gly Met Leu Val Leu Ala Ser Leu Gly Leu Val Trp
        115                 120                 125 gtt gcc ggc ctt tcg tgt ttg gcc tcg gag caa agc tta tac att ggt     432
Val Ala Gly Leu Ser Cys Leu Ala Ser Glu Gln Ser Leu Tyr Ile Gly
    130                 135                 140 ctc att ctc agc tgg tct atg ccc gtc ctc att ctg caa tgg agt ctc     480
Leu Ile Leu Ser Trp Ser Met Pro Val Leu Ile Leu Gln Trp Ser Leu
145                 150                 155                 160 ggt gca cat gtg ctc act acg cat gca aag ccg gtc ctg acg acg atc     528
Gly Ala His Val Leu Thr Thr His Ala Lys Pro Val Leu Thr Thr Ile
                165                 170                 175 gtg tcg gcc aca gcg tac ctt tgc gtg gcc gac gaa tgg gcg att cgt     576
Val Ser Ala Thr Ala Tyr Leu Cys Val Ala Asp Glu Trp Ala Ile Arg
            180                 185                 190 cac ggc atc tgg cgc atc aat cct gca aat ctt gtg ttg ccc atg ggc     624
His Gly Ile Trp Arg Ile Asn Pro Ala Asn Leu Val Leu Pro Met Gly
        195                 200                 205 aaa cat gca ctt ccc ctc gag gaa gcc ctc ttc ttc ttg gtg             666
Lys His Ala Leu Pro Leu Glu Glu Ala Leu Phe Phe Leu Val
    210                 215                 220

<210> SEQ ID NO 9
<211> LENGTH: 222
<212> TYPE: PRT
<213> ORGANISM: Schizochytrium

<400> SEQUENCE: 9

Tyr Leu Arg Phe His Gly Leu Phe Ile Leu Pro Pro Leu Leu Met Leu
1               5                   10                  15
```

-continued

```
Ala Arg Leu Ala His Gln Arg Ala Val Ala Asp Lys Gln Val Pro Phe
        20              25              30

Leu Arg Arg Ala Gly Phe Trp Thr Val Ala Leu Cys Val Val Ala Thr
        35              40              45

Leu Tyr Thr Thr Pro Trp Asp Asn Phe Leu Val Tyr Arg Arg Val Trp
    50              55              60

Gly Tyr Pro Pro Glu Arg Ile Leu Phe Val Ile Gly Tyr Val Pro Ile
65              70              75              80

Glu Glu Tyr Met Phe Phe Thr Leu Glu Thr Met Leu Val Ala Ala Val
            85              90              95

Trp Leu Gln Val Phe Gln Pro Thr Thr Leu Gln Ala Glu Val Gly Pro
        100             105             110

Arg Gly Lys Gly Gly Met Leu Val Leu Ala Ser Leu Gly Leu Val Trp
        115             120             125

Val Ala Gly Leu Ser Cys Leu Ala Ser Glu Gln Ser Leu Tyr Ile Gly
    130             135             140

Leu Ile Leu Ser Trp Ser Met Pro Val Leu Ile Leu Gln Trp Ser Leu
145             150             155             160

Gly Ala His Val Leu Thr Thr His Ala Lys Pro Val Leu Thr Thr Ile
            165             170             175

Val Ser Ala Thr Ala Tyr Leu Cys Val Ala Asp Glu Trp Ala Ile Arg
            180             185             190

His Gly Ile Trp Arg Ile Asn Pro Ala Asn Leu Val Leu Pro Met Gly
        195             200             205

Lys His Ala Leu Pro Leu Glu Glu Ala Leu Phe Phe Leu Val
    210             215             220
```

US 7,582,451 B2

CAROTENE SYNTHASE GENE AND USES THEREFOR

CROSS-REFERENCE TO RELATED APPLICATIONS

This application is a divisional of U.S. patent application Ser. No. 10/438,784, filed May 14, 2003, now U.S. Pat. No. 7,202,067, and entitled "Carotene Synthase Gene and Uses Thereof", which claims priority under 35 U.S.C. § 119(e) from U.S. Provisional Application Ser. No. 60/380,721, filed May 14, 2002, and entitled "Carotene Synthase Gene and Uses Thereof". The entire disclosure of U.S. patent application Ser. No. 10/438,784 and U.S. Provisional Application Ser. No. 60/380,721 is incorporated herein by reference.

FIELD OF THE INVENTION

This invention generally relates to a novel carotene synthase gene comprising the biological activities of phytoene dehydrogenase (PD), phytoene synthase (PS), and lycopene cyclase (LC), and to the protein encoded by the gene, and to methods of making and using the carotene synthase encoded thereby.

BACKGROUND OF THE INVENTION

Most carotenogenic bacteria synthesize β-carotene from the precursor geranylgeranyl pyrophosphate (GGPP) in three enzymatic steps (PS, PD, and LC; see FIG. 1), and these enzymes are encoded by three separate and distinct genes. There are reports in the literature of single genes in certain filamentous fungi encoding bi-functional enzymes for PS and LC activities (Verdoes, J. C., et al. *Mol. Gen. Genet.* 262, 453-461 (1999); Velayos, A. et al. *Eur. J. Biochem.* 267, 5509-5519 (2000); Arrach, N. et al. *Proc. Natl. Acad. Sci. USA* 98, 1687-1692 (2001); Arrach, N. et al. *Mol. Genet. Genomics* 266, 914-921 (2002)). In plants and some bacteria, the biochemical conversion of phytoene to lycopene is carried out by two separate enzymes encoded by two separate genes: a phytoene dehydrogenase that converts phytoene only to ζ-carotene and a ζ-carotene dehydrogenase that converts ζ-carotene to lycopene. Additionally, plants require a carotenoid isomerase for this conversion.

Globally, many people suffer from eye dysfunction caused by low vitamin A levels in their diets. In recent years, several research groups have engineered crop plants for the production of carotenoids, and principally β-carotene for its provitamin A activity in an attempt to ultimately provide this vitamin in staple foods. For example, published work (e.g., Shewmaker et al., *Plant J.*, 20, 401, (1999)) demonstrated that expression of a bacterial phytoene synthase (PS) in developing canola seed resulted in a significant increase in carotenoid production in those seeds. As another example, rice endosperm required the expression of phytoene dehydrogenase (PD) and phytoene synthase (PS) activity for β-carotene accumulation (Beyer et al., *J. Nutri.* 132, 506S, (2002)). The genes for these enzymes were from different biological sources. However, anecdotal information has suggested that subsequent breeding of these rice strains has lead to segregation of the PD and PS genes. These developmental problems are a block to the effective use of transformed plants to produce carotenoids.

The discovery of new enzymes in the carotenoid synthase pathway, and particularly, of enzymes that contain multiple enzyme functions, is therefore desirable for use in genetic engineering of microorganisms and plants for the production of carotenoids by a biosynthetic method.

SUMMARY OF THE INVENTION

One embodiment of the present invention relates to an isolated carotene synthase protein. The protein comprises an amino acid sequence selected from: (a) an amino acid sequence selected from the group consisting of SEQ ID NO:3, SEQ ID NO:5, SEQ ID NO:7, SEQ ID NO:9, an amino acid sequence consisting of positions 30 to 1268 of SEQ ID NO:3, and biologically active fragments thereof; (b) an amino acid sequence that is at least about 40% identical to SEQ ID NO:3 or to an amino acid sequence consisting of positions 30 to 1268 of SEQ ID NO:3, wherein the amino acid sequence has the following biological activities: phytoene dehydrogenase (PD) activity, phytoene synthase (PS) activity, and lycopene cyclase (LC) activity; (c) an amino acid sequence that is at least about 40% identical to SEQ ID NO:5, wherein the amino acid sequence has phytoene dehydrogenase (PD) activity; (d) an amino acid sequence that is at least about 40% identical to SEQ ID NO:7, wherein the amino acid sequence has phytoene synthase (PS) activity; and (e) an amino acid sequence that is at least about 40% identical to SEQ ID NO:9, wherein the amino acid sequence has lycopene cyclase (LC) activity. In one aspect, the isolated protein comprises an amino acid sequence that is at least about 60% identical one of the above-identified amino acid sequences, and in another aspect, is at least about 80% identical to one of the above-identified amino acid sequences, and in another aspect, is at least about 95% identical to one of the above-identified amino acid sequences. Preferably, the protein has a biological activity selected from: phytoene dehydrogenase (PD) activity, phytoene synthase (PS) activity, and/or lycopene cyclase (LC) activity. In one aspect, the protein comprises an amino acid sequence selected from: SEQ ID NO:3, SEQ ID NO:5, SEQ ID NO:7, SEQ ID NO:9, an amino acid sequence consisting of positions 30 to 1268 of SEQ ID NO:3, and biologically active fragments thereof. In another aspect, the protein comprises SEQ ID NO:5, SEQ ID NO:7 and SEQ ID NO:9.

A carotene synthase protein can be isolated from any suitable organism including, but not limited to, a Thraustochytriales microorganism (e.g., a *Schizochytrium* microorganism).

In one embodiment of the invention, an isolated protein is provided which includes an amino acid sequence selected from: (a) an amino acid sequence comprising SEQ ID NO:5 and SEQ ID NO:7; and (b) an amino acid sequence that is at least about 40% identical to the amino acid sequence of (a), wherein the amino acid sequence has the following biological activities: phytoene dehydrogenase (PD) activity and phytoene synthase (PS) activity.

Another embodiment of the present invention relates to an isolated antibody that selectively binds to an amino acid sequence selected from: SEQ ID NO:3, SEQ ID NO:5, SEQ ID NO:7, and SEQ ID NO:9.

Yet another embodiment of the present invention relates to an isolated nucleic acid molecule comprising a nucleic acid sequence selected from: (a) a nucleic acid sequence encoding an amino acid sequence selected from the group consisting of SEQ ID NO:3, SEQ ID NO:5, SEQ ID NO:7, SEQ ID NO:9, an amino acid sequence consisting of positions 30 to 1268 of SEQ ID NO:3, and biologically active fragments of any of the amino acid sequences; (b) a nucleic acid sequence encoding an amino acid sequence that is at least about 40% identical to SEQ ID NO:3 or to an amino acid sequence consisting of positions 30 to 1268 of SEQ ID NO:3, wherein the amino acid sequence has the following biological activities: phytoene dehydrogenase (PD) activity, phytoene synthase (PS) activity, and lycopene cyclase (LC) activity; (c) a nucleic acid sequence encoding an amino acid sequence that is at least about 40% identical to SEQ ID NO:5, wherein the amino acid sequence has phytoene dehydrogenase (PD) activity; (d) a nucleic acid sequence encoding an amino acid sequence that is at least about 40% identical to SEQ ID NO:7, wherein the amino acid sequence has phytoene synthase (PS) activity; (e) a nucleic acid sequence encoding an amino acid sequence that is at least about 40% identical to SEQ ID NO:9, wherein the amino acid sequence has lycopene cyclase (LC) activity; and (f) a nucleic acid sequence that is fully complementary to any one of the nucleic acid sequences of (a)-(e).

In one aspect, the isolated nucleic acid molecule comprises a nucleic acid sequence encoding an amino acid sequence that is at least about 60% identical to any of the above-described amino acid sequences, and in another aspect, is at least about 80% identical to any of the above-identified amino acid sequences, and in another aspect, is at least about 95% identical to any of the above-identified amino acid sequences. Preferably, the amino acid sequence has a biological activity chosen from: phytoene dehydrogenase (PD) activity, phytoene synthase (PS) activity, and/or lycopene cyclase (LC) activity. In one aspect of the invention, the nucleic acid molecule comprises a nucleic acid sequence encoding an amino acid sequence selected from: SEQ ID NO:3, SEQ ID NO:5, SEQ ID NO:7, SEQ ID NO:9, and an amino acid sequence consisting of positions 30 to 1268 of SEQ ID NO:3. In another aspect, the nucleic acid sequence is selected from: SEQ ID NO:1, SEQ ID NO:2, SEQ ID NO:4, SEQ ID NO:6 and SEQ ID NO:8. In yet another aspect, the nucleic acid sequence encodes any two amino acid sequences selected from the group consisting of SEQ ID NO:5, SEQ ID NO:7 and SEQ ID NO:9, and in another aspect, the nucleic acid sequence encodes SEQ ID NO:5, SEQ ID NO:7 and SEQ ID NO:9.

Also included in the present invention is a recombinant nucleic acid molecule comprising any one of the above-identified nucleic acid molecules operatively linked to a transcription control sequence. The transcription control sequence includes, but is not limited to, a tissue-specific transcription control sequence. The recombinant nucleic acid molecule can in some aspects further include a targeting sequence.

Another embodiment of the invention relates to a recombinant cell that has been transformed with any of the recombinant nucleic acid molecules of the invention.

Yet another embodiment of the invention relates to a genetically modified microorganism or a genetically modified plant for producing a carotenoid by a biosynthetic process, the microorganism or plant being transformed with any of the recombinant nucleic acid molecules of the present invention.

Another embodiment of the invention relates to a genetically modified microorganism for producing a carotenoid by a biosynthetic process. The microorganism comprises a nucleic acid molecule encoding a carotene synthase, such nucleic acid molecule having been modified to increase the expression or biological activity of the carotene synthase. The carotene synthase can include any of the above-described amino acid sequences. In one aspect of the invention, the nucleic acid molecule encoding a carotene synthase is an endogenous gene in the microorganism. In another aspect, the microorganism has been transformed with a nucleic acid molecule encoding the carotene synthase. In this embodiment, the microorganism can be a Thraustochytriales microorganism (e.g., a *Schizochytrium*). In another aspect, the microorganism comprises an endogenous gene encoding the carotene synthase and has been transformed with a recombinant nucleic acid molecule encoding the carotene synthase. In this aspect, one or both of the gene and the recombinant nucleic acid molecule has been modified to increase the expression or biological activity of the carotene synthase. The microorganism can include a Thraustochytriales microorganism (e.g., a *Schizochytrium* microorganism).

Another embodiment of the present invention relates to a biomass comprising any of the genetically modified microorganisms described above. Also included in the invention are food products and pharmaceutical products comprising such a biomass.

Yet another embodiment of the present invention relates to a method to produce a carotenoid by a biosynthetic process. The method includes the step of culturing in a fermentation medium a genetically modified microorganism that has increased expression or biological activity of a carotene synthase as described above.

Another embodiment of the invention is a method to produce a carotenoid by a biosynthetic process, comprising growing a genetically modified plant that has been transformed with a recombinant nucleic acid molecule encoding a protein comprising any of the carotene synthase proteins as described above. In one embodiment, the recombinant nucleic acid molecule encodes a protein having phytoene dehydrogenase (PD) activity and phytoene synthase (PS) activity, but not having lycopene cyclase (LC) activity.

Yet another embodiment of the present invention relates to an oligonucleotide, comprising at least 12 contiguous nucleotides of a nucleic acid sequence selected from the group consisting of: SEQ ID NO:1, SEQ ID NO:2, SEQ ID NO:4, SEQ ID NO:6, SEQ ID NO:8, and a nucleic acid sequence fully complementary thereto.

Another embodiment of the present invention relates to a genetically modified microorganism lacking pigmentation, wherein the microorganism (e.g., a microorganism of the order Thraustochytriales) has been genetically modified to selectively delete or inactivate a carotene synthase gene or portion thereof encoding a functional domain. The carotene synthase gene is chosen from: (a) a nucleic acid sequence encoding SEQ ID NO:3; and (b) a nucleic acid sequence encoding an amino acid sequence that is at least about 40% identical to SEQ ID NO:3, wherein a protein having the amino acid sequence has a biological activity selected from the group consisting of phytoene dehydrogenase (PD) activity, phytoene synthase (PS) activity, and lycopene cyclase (LC) activity. In one aspect, the carotene synthase gene comprises a nucleic acid sequence represented by SEQ ID NO:3. The microorganism can be chosen from, but is not limited to, a Thraustochytriales microorganism, such as a *Schizochytrium*. In one aspect, the carotene synthase gene has been modified in a regulatory region to inhibit expression of the gene. In another aspect, the carotene synthase gene has been partially or completely deleted so that the microorganism does not produce a functional carotene synthase. In another aspect, the carotene synthase gene has been mutated or inactivated by targeted homologous recombination with a nucleic acid sequence that hybridizes to the carotene synthase gene and includes a heterologous nucleic acid sequence that disrupts the coding region of the carotene synthase gene.

Also included in the invention is a biomass comprising genetically modified microorganisms (e.g., microorganisms of the order Thraustochytriales) that have reduced pigmentation as compared to a wild-type microorganism of the same species, wherein the microorganisms have been genetically modified to selectively delete or inactivate a carotene synthase gene as described above. Another aspect of the invention relates to a food product comprising such a biomass.

Another embodiment of the present invention relates to a method for producing lipids lacking pigmentation from a biosynthetic process. This method includes the step of culturing under conditions effective to produce the lipids genetically modified microorganisms (e.g., microorganisms of the order Thraustochytriales), wherein the microorganisms have been genetically modified to selectively delete or inactivate a carotene synthase gene as described above.

Yet another embodiment of the present invention relates to a method to recover lipids lacking pigmentation from a biosynthetic process, comprising recovering lipids from a culture of genetically modified microorganism (e.g., a microorganism of the order Thraustochytriales), wherein the microorganisms have been genetically modified to selectively delete or inactivate a carotene synthase gene as described above. Accordingly, another aspect of the invention relates to the lipids lacking pigmentation that are recovered from a culture of genetically modified microorganisms as described above, wherein the microorganisms have been genetically modified to selectively delete or inactivate a carotene synthase gene as described above, as well as products comprising the lipids (e.g., food products or pharmaceutical products).

Another embodiment of the present invention relates to a method for producing a carotenoid comprising contacting a substrate with an isolated carotene synthase under conditions sufficient to produce a carotenoid, wherein the isolated carotene synthase comprises any of the amino acid sequences described above.

BRIEF DESCRIPTION OF THE DRAWINGS OF THE INVENTION

DETAILED DESCRIPTION OF THE INVENTION

The present invention describes a novel three domain gene within *Schizochytrium* sp. that encodes a protein with three different enzymatic activities: phytoene dehydrogenase (PD), phytoene synthase (PS), and lycopene cyclase (LC). This discovery of a multi-functional protein provides a novel approach for the economic production of carotenoids. For example, it is now possible to clone and express one gene with three key sequential enzymatic functions rather than cloning two, three, or four genes from the carotenoid biosynthesis pathways of other organisms, which will greatly facilitate the genetic modification of production organisms. In addition, it is possible to use the enzymatic domains of the *Schizochytrium* CS gene individually or in various combinations to construct various recombinant/synthetic genes expressing, one, two, or all three domains.

More specifically, the present invention generally relates to an isolated gene, referred to here as a carotene synthase gene, and to homologues thereof, to the enzyme encoded by such gene and to biologically active portions and homologues thereof, to recombinant nucleic acid molecules comprising such genes, to microorganisms and plants that have been transformed with such genes and progeny thereof, to *Schizochytrium* and other Thraustochytrid organisms that have been genetically modified to increase or decrease the action of such a gene, and to methods of producing carotenoids and derivatives thereof by culturing a microorganism or plant as described above under conditions effective to produce the carotenoids.

Figure 1:
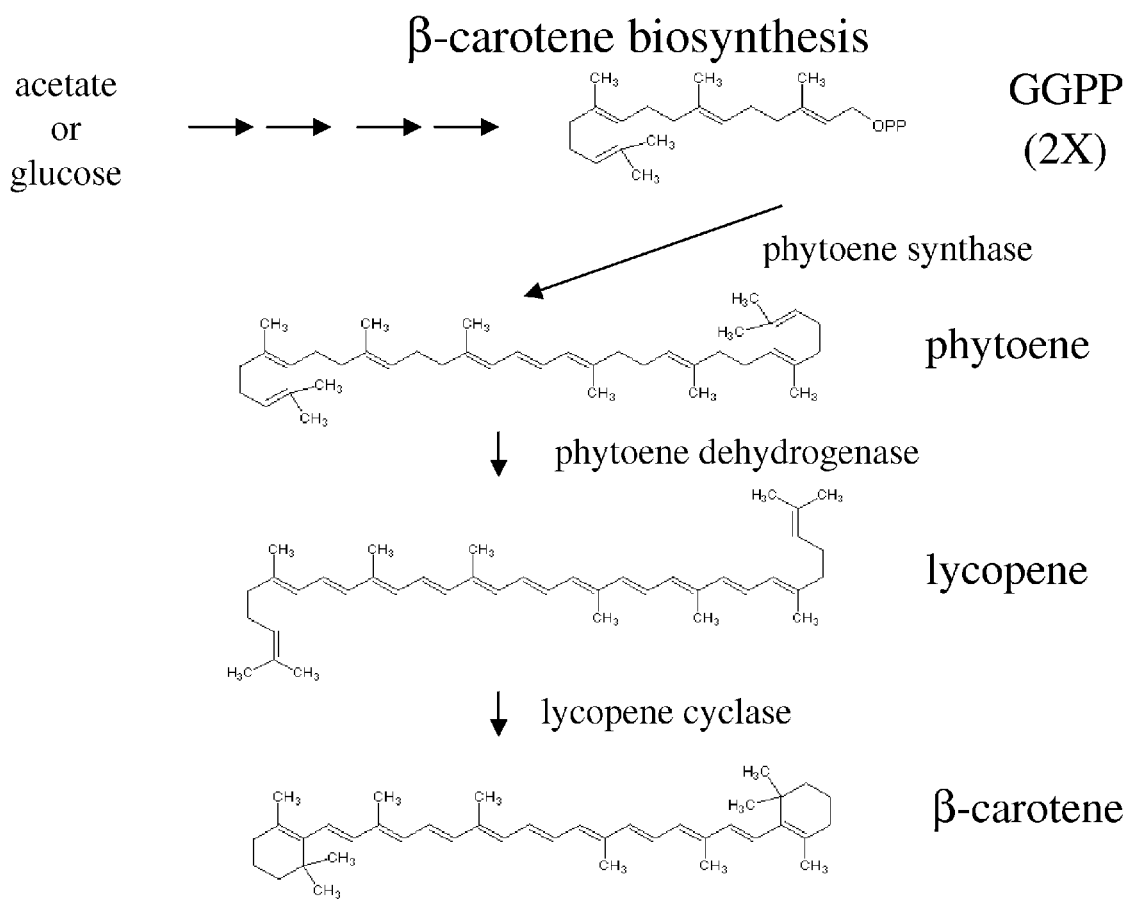
FIG. 1 is a diagram showing β-carotene biosynthesis from GGPP.

The present inventors have identified a gene in *Schizochytrium* sp. associated with a carotenoid biosynthetic pathway. This gene encodes a single polypeptide that contains three distinct regions (domains). Comparison of the deduced amino acid sequences of these three domains with publicly available databases indicate these domains have the following enzymatic activities (listed, in order, from the deduced N-terminus toward the C-terminus): phytoene dehydrogenase (PD), phytoene synthase (PS) and lycopene cyclase (LC). By reference to established metabolic pathway schemes for carotenoid biosynthesis, these three enzymatic activities could accomplish the conversion of geranylgeranyl-pyrophosphate to β-carotene (e.g., see FIG. 1). Here the present inventors define the carotene synthase (CS) gene of the present invention as a nucleic acid sequence that encodes an enzyme with PD, PS and LC domains. It is understood that the enzyme (activity) names "phytoene dehydrogenase" and "phytoene desaturase" are interchangeable and that any reference herein to "phytoene dehydrogenase" or "PD" includes reference to enzymes and activities designated "phytoene desaturase".

Although many genes encoding enzymes of the carotenoid pathway have been identified, cloned and sequenced, to the present inventors' knowledge, this is the first instance in which a gene associated with that pathway has been cloned and characterized from *Schizochytrium*—or any member of the Order Thraustochytriales. Additionally, to the present inventors' knowledge, this is the first instance in which three enzymatic functions of the carotenoid pathway have been found in a single polypeptide. Examples do exist in which two enzymatic functions of the carotenoid synthesis pathway (specifically, PS and LC) have been found in one polypeptide—but not three enzymatic functions.

Figure 2:
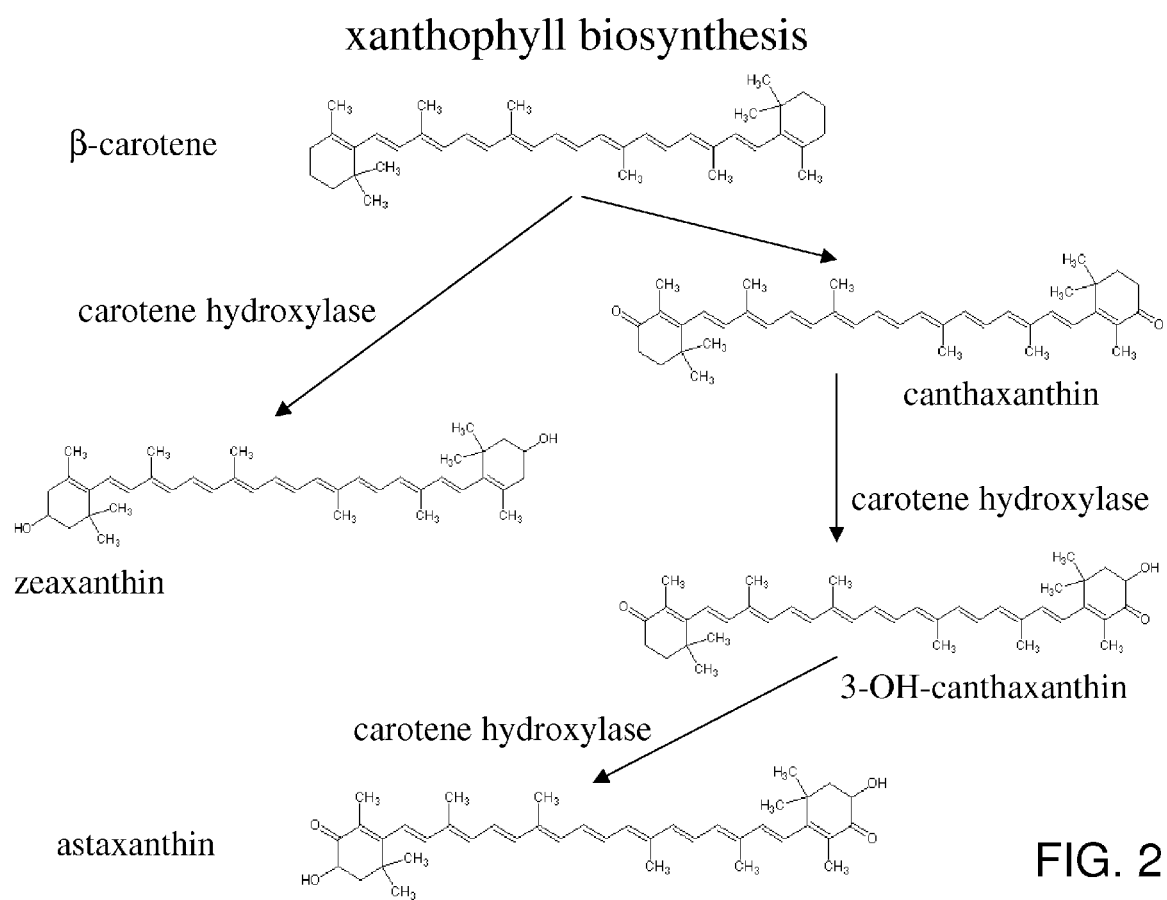
FIG. 2 is a diagram showing the production of carotenoids derived from β-carotene.

PS, PD and LC are sequential enzymes in the carotenoid biosynthetic pathway. The occurrence of these three enzymatic functions in a single polypeptide suggests metabolic channeling of the intermediates in this series of reactions. There are examples (e.g., see Shewmaker, et al., "Seed-specific overexpression of phytoene synthase: increase in carotenoids and other metabolic effects." *The Plant Journal* 20, 401-412 (1999)) in which increasing the amount of PS resulted in a dramatic increase in flux through the carotenoid synthesis pathway. Introduction (or increased expression) of the *Schizochytrium* carotene synthase gene encoding the PD, PS and LC enzymatic domains in either a heterologous host, or in *Schizochytrium* itself, would permit the simultaneous elevation of these three enzymatic activities. This could have significant advantages over the introduction of two or three discrete genes encoding these three functions. It is anticipated that increased levels of these enzymatic activities will result in an increased production of β-carotene in either *Schizochytrium* or a heterologous host, and indeed, the present inventors have shown that *Schizochytrium* transformed with the carotene synthase gene of the invention produce increased amounts of β-carotene as compared to controls. This increased amount of β-carotene could be useful in itself, or the increased level of β-carotene could serve as substrate for the production of carotenoids derived from β-carotene (such as, but not limited to, canthaxanthin, zeaxanthin or astaxanthin; see FIG. 2). The present inventors have also shown that *Schizochytrium* transformed with the carotene synthase gene of the invention produce increased amounts of astaxanthin as compared controls (see Examples). In addition, modification of the carotene synthase gene could result in the production of lycopene that in turn could serve as substrate for the production of α-carotene and lutein.

Accordingly, one embodiment of the present invention relates to an isolated carotene synthase. As used herein, reference to an isolated protein, including an isolated carotene synthase, is to a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated carotene synthase of the present invention is produced recombinantly. In addition, and by way of example, a "*Schizochytrium* carotene synthase" refers to a carotene synthase (generally including a homologue of a naturally occurring carotene synthase) from a *Schizochytrium* or to a carotene synthase protein that has been otherwise produced from the knowledge of the structure (e.g., sequence) and perhaps the function of a naturally occurring carotene synthase from *Schizochytrium*. In other words, a *Schizochytrium* carotene synthase includes any carotene synthase that has substantially similar structure and function of a naturally occurring carotene synthase from *Schizochytrium* or that is a biologically active (i.e., has biological activity) homologue of a naturally occurring carotene synthase from *Schizochytrium* as described in detail herein. As such, a *Schizochytrium* carotene synthase protein can include purified, partially purified, recombinant, mutated/modified and synthetic proteins. According to the present invention, the terms "modification" and "mutation" can be used interchangeably, particularly with regard to the modifications/mutations to the amino acid sequences of carotene synthase (or nucleic acid sequences) described herein.

According to the present invention, a homologue of a carotene synthase (i.e., a carotene synthase homologue) includes carotene synthases in which at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, farnasylation, amidation and/or addition of glycosylphosphatidyl inositol). In a preferred embodiment, a carotene synthase homologue has measurable or detectable carotene synthase enzymatic activity (i.e., has biological activity). Measurable or detectable carotene synthase enzymatic activity can include the enzymatic activity of just one, or two or all three of the enzymatic domains in the carotene synthase of the present invention (discussed in detail below). In another embodiment, a carotene synthase homologue may or may not have measurable carotene synthase enzymatic activity, but is used for the preparation of antibodies or the development of oligonucleotides useful for identifying other carotene synthases. For example, the production of an antibody against carotene synthase and production of probes and primers useful in the cloning of a carotene synthase are described in the Examples.

Carotene synthase homologues can be the result of natural allelic variation or natural mutation. Carotene synthase homologues of the present invention can also be produced using techniques known in the art including, but not limited to, direct modifications to the protein or modifications to the gene encoding the protein using, for example, classic or recombinant DNA techniques to effect random or targeted mutagenesis. A naturally occurring allelic variant of a nucleic acid encoding a carotene synthase is a gene that occurs at essentially the same locus (or loci) in the genome as the gene which encodes an amino acid sequence represented by SEQ ID NO:3, but which, due to natural variations caused by, for example, mutation or recombination, has a similar but not identical sequence. Natural allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art. Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modifications in carotene synthase homologues, as compared to the wild-type protein, either increase, decrease, or do not substantially change, the basic biological activity of the carotene synthase homologue as compared to the naturally occurring protein, carotene synthase. In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications of a protein, such as in a homologue or mimetic (discussed below), may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action of a protein. Similarly, modifications which result in an increase in protein expression or an increase in the activity of the protein, can be referred to as amplification, overproduction, activation, enhancement, up-regulation or increased action of a protein.

According to one embodiment of the present invention, a biologically active carotene synthase, including a biologically active homologue or fragment thereof, has at least one characteristic of biological activity of activity a wild-type, or naturally occurring carotene synthase described herein. A carotene synthase biological activity includes the ability to convert geranylgeranyl-pyrophosphate to β-carotene and as described above, can include any one or more of the enzymatic activities of the three domains of carotene synthase described herein. According to the present invention, a carotene synthase of the present invention has at least one, and preferably two, and most preferably three, enzymatic activities. These enzymatic activities are: (1) phytoene dehydrogenase (PD) enzymatic activity, (2) phytoene synthase (PS) enzymatic activity, and (3) lycopene cyclase (LC) enzymatic activity. General reference to carotene synthase biological activity or enzymatic activity typically refers to all three enzymatic activities, but does not exclude reference to only one or two of the enzymatic activities. Methods for measuring these enzymatic activities are known in the art (e.g., see Fraser and Bramley, *Meth. Enzymol.* 214, 365 (1993); Camara, *Meth. Enzymol.* 214, 352, (1993); Hornero-Mendez and Britton, *FEBS Lett.* 515, 133, (2002)). An isolated carotene synthase of the present invention can also be characterized by its specific activity. A "specific activity" refers to the rate of conversion of geranylgeranyl-pyrophosphate to β-carotene by the enzyme. More specifically, it refers to the number of molecules of geranylgeranyl-pyrophosphate converted to β-carotene per mg of the enzyme per time unit.

Methods to measure protein expression levels according to this invention, include, but are not limited to: western blotting, immunocytochemistry, flow cytometry or other immunologic-based assays; assays based on a property of the protein including but not limited to substrate binding. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al. Anal. Biochem. 212:457-468 (1993); Schuster et al., Nature 365:343-347 (1993)). Other suitable assays for measuring the binding of one protein to another include, for example, immunoassays such as enzyme linked immunoabsorbent assays (ELISA) and radioimmunoassays (RIA), or determination of binding by monitoring the change in the spectroscopic or optical properties of the proteins through fluorescence, UV absorption, circular dichrosim, or nuclear magnetic resonance (NMR).

In one embodiment, a carotene synthase (e.g., including homologues of the carotene synthase isolated from Schizochytrium and described in detail herein) includes proteins that have at least one of: (1) phytoene dehydrogenase (PD) enzymatic activity, (2) phytoene synthase (PS) enzymatic activity, and (3) lycopene cyclase (LC) enzymatic activity. In one embodiment of the invention, an isolated carotene synthase comprises an amino acid sequence selected from: (a) an amino acid sequence selected from: SEQ ID NO:3, SEQ ID NO:5, SEQ ID NO:7, SEQ ID NO:9, an amino acid sequence consisting of positions 30 to 1268 of SEQ ID NO:3, and biologically active fragments thereof; (b) an amino acid sequence that is at least about 40% identical to SEQ ID NO:3 or to an amino acid sequence consisting of positions 30 to 1268 of SEQ ID NO:3, wherein the amino acid sequence has the following biological activities: phytoene dehydrogenase (PD) activity, phytoene synthase (PS) activity, and lycopene cyclase (LC) activity; (c) an amino acid sequence that is at least about 40% identical to SEQ ID NO:5, wherein the amino acid sequence has phytoene dehydrogenase (PD) activity; (d) an amino acid sequence that is at least about 40% identical to SEQ ID NO:7, wherein the amino acid sequence has phytoene synthase (PS) activity; or (e) an amino acid sequence that is at least about 40% identical to SEQ ID NO:9, wherein the amino acid sequence has lycopene cyclase (LC) activity.

The complete amino acid sequence for a Schizochytrium carotene synthase of the present invention which includes all three enzymatic domains and the signal sequence is represented herein by SEQ ID NO:3 (encoded by SEQ ID NO:2 or by positions 1406-5212 of SEQ ID NO:1). Without being bound by theory, the present inventors believe that amino acids 1-29 of SEQ ID NO:3 are a signal sequence, which may be cleaved in some circumstances to produce a carotene synthase having an amino acid sequence spanning positions 30 to 1268 of SEQ ID NO:3. Referring now to SEQ ID NO:3, the first domain in the CS protein, the phytoene dehydrogenase (PD) domain, spans from amino acid 53 to 521 of SEQ ID NO:3 and is represented herein by SEQ ID NO:5. SEQ ID NO:5 is encoded by the nucleic acid sequence represented herein by SEQ ID NO:4 (positions 157 to 1563 of SEQ ID NO:2). The second domain in the CS protein, the phytoene synthase (PS) domain, spans from amino acid 586 to 860 of SEQ ID NO:3 and is represented herein by SEQ ID NO:7. SEQ ID NO:7 is encoded by the nucleic acid sequence represented herein by SEQ ID NO:6 (positions 1756 to 2580 of SEQ ID NO:2). The third domain in the CS protein, the lycopene cyclase (LC) domain, spans from amino acid 911 to 1132 of SEQ ID NO:3 and is represented herein by SEQ ID NO:9. SEQ ID NO:5 is encoded by the nucleic acid sequence represented herein by SEQ ID NO:8 (positions 2731 to 3396 of SEQ ID NO:2).

In one aspect of the invention, a carotene synthase comprises an amino acid sequence that is at least about 40% identical to the amino acid sequence represented by SEQ ID NO:3 over at least about 325 amino acids of SEQ ID NO:3. In another aspect, a carotene synthase of the invention comprises an amino acid sequence that is at least 45% identical to SEQ ID NO:3 over at least about 325 amino acids, and in another aspect at least about 50%, and in another aspect at least about 55%, and in another aspect at least about 60%, and in another aspect at least about 65%, and in another aspect at least about 70%, and in another aspect at least about 75%, and in another aspect at least about 80%, and in another aspect at least about 85%, and in another aspect at least about 90%, and in another aspect at least about 95% identical to the amino acid sequence represented by SEQ ID NO:3 over at least about 325 amino acids of SEQ ID NO:3, and more preferably over at least about 350 amino acids, and more preferably over at least about 375 amino acids, and more preferably over at least about 400 amino acids, and more preferably over at least about 500 amino acids, and more preferably over at least about 600 amino acids, and more preferably over at least about 700 amino acids, and more preferably over at least about 800 amino acids, and more preferably over at least about 900 amino acids, and more preferably over at least about 1000 amino acids, and more preferably over 1050 amino acids, and more preferably over the full length of the amino acid sequence represented by SEQ ID NO:3. Such a protein preferably comprises at least one, two or all three enzymatic activities of a carotene synthase of the invention selected from: phytoene dehydrogenase (PD) activity, phytoene synthase (PS) activity, and lycopene cyclase (LC) activity.

In one aspect of the invention, a carotene synthase comprises an amino acid sequence that is at least about 40% identical to the amino acid sequence represented by SEQ ID NO:5. In another aspect, a carotene synthase of the invention comprises an amino acid sequence that is at least 45% identical to SEQ ID NO:5, and in another aspect at least about 50%, and in another aspect at least about 55%, and in another aspect at least about 60%, and in another aspect at least about 65%, and in another aspect at least about 70%, and in another aspect at least about 75%, and in another aspect at least about 80%, and in another aspect at least about 85%, and in another aspect at least about 90%, and in another aspect at least about 95% identical to the amino acid sequence represented by SEQ ID NO:5 over the full length of the amino acid sequence represented by SEQ ID NO:5. Such a protein comprises at least phytoene dehydrogenase (PD) activity.

In one aspect of the invention, a carotene synthase comprises an amino acid sequence that is at least about 40% identical to the amino acid sequence represented by SEQ ID NO:7. In another aspect, a carotene synthase of the invention comprises an amino acid sequence that is at least 45% identical to SEQ ID NO:7, and in another aspect at least about 50%, and in another aspect at least about 55%, and in another aspect at least about 60%, and in another aspect at least about 65%, and in another aspect at least about 70%, and in another aspect at least about 75%, and in another aspect at least about 80%, and in another aspect at least about 85%, and in another aspect at least about 90%, and in another aspect at least about 95% identical to the amino acid sequence represented by SEQ ID NO:7 over the full length of the amino acid sequence represented by SEQ ID NO:7. Such a protein comprises at least phytoene synthase (PS) activity.

In one aspect of the invention, a carotene synthase comprises an amino acid sequence that is at least about 40% identical to the amino acid sequence represented by SEQ ID NO:9. In another aspect, a carotene synthase of the invention comprises an amino acid sequence that is at least 45% identical to SEQ ID NO:9, and in another aspect at least about 50%, and in another aspect at least about 55%, and in another aspect at least about 60%, and in another aspect at least about 65%, and in another aspect at least about 70%, and in another aspect at least about 75%, and in another aspect at least about 80%, and in another aspect at least about 85%, and in another aspect at least about 90%, and in another aspect at least about 95% identical to the amino acid sequence represented by SEQ ID NO:9 over the full length of the amino acid sequence represented by SEQ ID NO:9. Such a protein comprises at least lycopene cyclase (LC) activity.

In one embodiment of the present invention, a carotene synthase homologue according to the present invention has an amino acid sequence that is less than about 100% identical to any of SEQ ID NO:3, SEQ ID NO:5, SEQ ID NO:7 or SEQ ID NO:9. In another aspect of the invention, a carotene synthase homologue according to the present invention has an amino acid sequence that is less than about 99% identical to any of the above-identified amino acid sequences, and in another embodiment, is less than is less than 98% identical to any of the above-identified amino acid sequences, and in another embodiment, is less than 97% identical to any of the above-identified amino acid sequences, and in another embodiment, is less than 96% identical to any of the above-identified amino acid sequences, and in another embodiment, is less than 95% identical to any of the above-identified amino acid sequences, and in another embodiment, is less than 94% identical to any of the above-identified amino acid sequences, and in another embodiment, is less than 93% identical to any of the above-identified amino acid sequences, and in another embodiment, is less than 92% identical to any of the above-identified amino acid sequences, and in another embodiment, is less than 91% identical to any of the above-identified amino acid sequences, and in another embodiment, is less than 90% identical to any of the above-identified amino acid sequences, and so on, in increments of whole integers.

In one embodiment of the invention, a carotene synthase comprises any two of the amino acid sequences selected from SEQ ID NO:5 (PD), SEQ ID NO:7 (PS), or SEQ ID NO:9 (LC) (or the homologues thereof), but does not necessarily comprise the third sequence. For example, a carotene synthase of the invention can be produced (i.e., a homologue of the naturally occurring *Schizochytrium* CS) that includes only the phytoene dehydrogenase (PD) and phytoene synthase (PS) domains of the wild-type CS (i.e., the lycopene cyclase (LC) domain is deleted or omitted from a synthesized construct). An example of a construct that deletes the LC domain is described in the Examples. This protein would be useful, for example to produce the carotenoid lycopene. Knowing the domain structure of the complete carotene synthase of the invention allows one of skill in the art to select one or two of the domains to produce novel proteins having only one or two of the enzyme functions, instead of all three enzyme functions.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
    Reward for match=1
    Penalty for mismatch=−2
    Open gap (5) and extension gap (2) penalties
    gap x_dropoff (50) expect (10) word size (11) filter (on)

For blastp, using 0 BLOSUM62 matrix:
    Open gap (11) and extension gap (1) penalties gap x_dropoff (50) expect (10) word size (3) filter (on).

A carotene synthase can also include proteins having an amino acid sequence comprising at least 10 contiguous amino acid residues of SEQ ID NO:3 (i.e., 10 contiguous amino acid residues having 100% identity with 10 contiguous amino acids of the amino acid sequence represented by SEQ ID NO:3). In another aspect, a homologue of a carotene synthase amino acid sequence includes amino acid sequences comprising at least 20, or at least about 30, or at least about 40, or at least about 50, or at least about 75, or at least about 100, or at least about 115, or at least about 130, or at least about 150, or at least about 200, or at least about 250, or at least about 300, or at least about 350, or at least about 400, or at least about 500, or at least about 600, or at least about 700, or at least about 800, or at least about 900, or at least about 1000, or at least about 1100, or at least about 1200, contiguous amino acid residues of the amino acid sequence represented by SEQ ID NO:3. A carotene synthase homologue can include proteins encoded by a nucleic acid sequence comprising at least about 30, or at least about 60, or at least about 90, or at least about 150, or at least about 225, or at least about 300, or at least about 750, or at least about 900, or at least about 1050, or at least about 1200, or at least about 1500, or at least about 1800, or at least about 2100, or at least about 2400, or at least about 2700, or at least about 3000, contiguous nucleotides of the nucleic acid sequence represented by SEQ ID NO:1 or SEQ ID NO:2. In a preferred embodiment, a carotene synthase homologue has measurable carotene synthase biological activity (i.e., has biological activity), as described above, including one, two or all three of the enzymatic activities described for a carotene synthase of the present invention.

According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

In another embodiment, a carotene synthase, including a carotene synthase homologue, includes a protein having an amino acid sequence that is sufficiently similar to a natural carotene synthase amino acid sequence that a nucleic acid sequence encoding the homologue is capable of hybridizing under moderate, high or very high stringency conditions (described below) to (i.e., with) a nucleic acid molecule encoding the natural carotene synthase (i.e., to the complement of the nucleic acid strand encoding the natural carotene synthase amino acid sequence). Preferably, a homologue of a carotene synthase is encoded by a nucleic acid molecule comprising a nucleic acid sequence that hybridizes under moderate, high or very high stringency conditions to the complement of a nucleic acid sequence that encodes a protein comprising SEQ ID NO:3, SEQ ID NO:5, SEQ ID NO:7 or SEQ ID NO:9. Even more preferably, a homologue of a carotene synthase is encoded by a nucleic acid molecule comprising a nucleic acid sequence that hybridizes under moderate, high or very high stringency conditions to the complement of the nucleic acid sequence represented by SEQ ID NO:1, SEQ ID NO:2, SEQ ID NO:4, SEQ ID NO:6 or SEQ ID NO:8.

A nucleic acid sequence complement of nucleic acid sequence encoding a carotene synthase of the present invention refers to the nucleic acid sequence of the nucleic acid strand that is complementary to the strand which encodes carotene synthase. It will be appreciated that a double stranded DNA which encodes a given amino acid sequence comprises a single strand DNA and its complementary strand having a sequence that is a complement to the single strand DNA. As such, nucleic acid molecules of the present invention can be either double-stranded or single-stranded, and include those nucleic acid molecules that form stable hybrids under stringent hybridization conditions with a nucleic acid sequence that encodes the amino acid sequence of SEQ ID NO:3, and/or with the complement of the nucleic acid sequence that encodes an amino acid sequence of SEQ ID NO:3. Methods to deduce a complementary sequence are known to those skilled in the art. It should be noted that since nucleic acid sequencing technologies are not entirely error-free, the sequences presented herein, at best, represent apparent sequences of a carotene synthase of the present invention.

As used herein, reference to hybridization conditions refers to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

Carotene synthases also include expression products of gene fusions (for example, used to overexpress soluble, active forms of the recombinant protein), of mutagenized genes (such as genes having codon modifications to enhance gene transcription and translation), and of truncated genes (such as genes having membrane binding domains removed to generate soluble forms of a membrane protein, or genes having signal sequences removed which are poorly tolerated in a particular recombinant host). It is noted that carotene synthases and protein homologues of the present invention include proteins which do not have carotene synthase activity. Such proteins are useful, for example, for the production of antibodies or for production of genetically modified organisms that lack the ability to produce one or more carotenoids.

The minimum size of a protein and/or homologue of the present invention is a size sufficient to have carotene synthase biological activity or, when the protein is not required to have such enzyme activity, sufficient to be useful for another purpose associated with a carotene synthase of the present invention, such as for the production of antibodies that bind to a naturally occurring carotene synthase. As such, the minimum size of a carotene synthase or homologue of the present invention is a size suitable to form at least one epitope that can be recognized by an antibody, and is typically at least 8 amino acids in length, and preferably 10, and more preferably 15, and more preferably 20, and more preferably 25, and even more preferably 30 amino acids in length, and up to 1268 amino acids in length, in increments of any whole integer from 1 to 1268, with preferred sizes depending on whether full-length, multivalent (i.e., fusion protein having more than one domain, each of which has a function), or functional portions of such proteins are desired. There is no limit, other than a practical limit, on the maximum size of such a protein in that the protein can include a portion of a carotene synthase (including carotene synthase homologues) or a full-length carotene synthase.

Similarly, the minimum size of a nucleic acid molecule of the present invention is a size sufficient to encode a protein having carotene synthase activity, sufficient to encode a protein comprising at least one epitope which binds to an antibody, or sufficient to form a probe or oligonucleotide primer that is capable of forming a stable hybrid with the complementary sequence of a nucleic acid molecule encoding a natural carotene synthase (e.g., under low, moderate or high stringency conditions). As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a portion of a carotene synthase encoding sequence, a nucleic acid sequence encoding a full-length carotene synthase (including a carotene synthase gene), or multiple genes, or portions thereof.

The present invention also includes a fusion protein that includes a carotene synthase-containing domain (including a homologue or functional domain of a carotene synthase) attached to one or more fusion segments. Suitable fusion segments for use with the present invention include, but are not limited to, segments that can: enhance a protein's stability; provide other desirable biological activity (e.g., a cytokine or another activity associated with carotenoid biosynthesis); and/or assist with the purification of a carotene synthase (e.g., by affinity chromatography). A suitable fusion segment can be a domain of any size that has the desired function (e.g., imparts increased stability, solubility, action or biological activity; and/or simplifies purification of a protein). Fusion segments can be joined to amino and/or carboxyl termini of the carotene synthase-containing domain of the protein and can be susceptible to cleavage in order to enable straightforward recovery of a carotene synthase. Fusion proteins are preferably produced by culturing a recombinant cell transformed with a fusion nucleic acid molecule that encodes a protein including the fusion segment attached to either the carboxyl and/or amino terminal end of a carotene synthase-containing domain.

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

Carotene synthases can be isolated from a various microorganisms including members of the order, Thraustochytriales. For example, preferred microorganisms from which a carotene synthase of the present invention may be derived include microorganisms from a genus including, but not limited to: *Thraustochytrium*, *Labyrinthuloides*, *Japonochytrium*, and *Schizochytrium*. Preferred species within these genera include, but are not limited to: any *Schizochytrium* species, including *Schizochytrium aggregatum, Schizochytrium limacinum, Schizochytrium minutum*; any *Thraustochytrium* species (including former *Ulkenia* species such as *U. visurgensis, U. amoeboida, U. sarkariana, U. profunda, U. radiata, U. minuta* and *Ulkenia* sp. BP-5601), and including *Thraustochytrium striatum, Thraustochytrium aureum, Thraustochytrium roseum*; and any *Japonochytrium* species. Particularly preferred strains of Thraustochytriales include, but are not limited to: *Schizochytrium* sp. (S31) (ATCC 20888); *Schizochytrium* sp. (S8) (ATCC 20889);

*Schizochytrium* sp. (LC-RM) (ATCC 18915); *Schizochytrium* sp. (SR21); *Schizochytrium aggregatum* (Goldstein et Belsky) (ATCC 28209); *Schizochytrium limacinum* (Honda et Yokochi) (IFO 32693); *Thraustochytrium* sp. (23B) (ATCC 20891); *Thraustochytrium striatum* (Schneider) (ATCC 24473); *Thraustochytrium aureum* (Goldstein) (ATCC 34304); *Thraustochytrium roseum* (Goldstein)(ATCC 28210); and *Japonochytrium* sp. (L1)(ATCC 28207).

Developments have resulted in revision of the taxonomy of the Thraustochytrids. Taxonomic theorists place Thraustochytrids with the algae or algae-like protists. However, because of taxonomic uncertainty, it would be best for the purposes of the present invention to consider the strains described in the present invention as Thraustochytrids (Order: Thraustochytriales; Family: Thraustochytriaceae; Genus:*Thraustochytrium, Schizochytrium, Labyrinthuloides*, or *Japonochytrium*). For the present invention, members of the labrinthulids are considered to be included in the Thraustochytrids. Taxonomic changes are summarized below. Strains of certain unicellular microorganisms disclosed herein are members of the order Thraustochytriales (also referred to as Thraustochytrids). Thraustochytrids are marine eukaryotes with a evolving taxonomic history. Problems with the taxonomic placement of the Thraustochytrids have been reviewed by Moss (1986), Bahnweb and Jackle (1986) and Chamberlain and Moss (1988). According to the present invention, the phrases "Thraustochytrid", "Thraustochytriales microorganism" and "microorganism of the order Thraustochytriales" can be used interchangeably.

For convenience purposes, the Thraustochytrids were first placed by taxonomists with other colorless zoosporic eukaryotes in the Phycomycetes (algae-like fungi). The name Phycomycetes, however, was eventually dropped from taxonomic status, and the Thraustochytrids were retained in the Oomycetes (the biflagellate zoosporic fungi). It was initially assumed that the Oomycetes were related to the heterokont algae, and eventually a wide range of ultrastructural and biochemical studies, summarized by Barr (Barr, 1981, *Biosystems* 14:359-370) supported this assumption. The Oomycetes were in fact accepted by Leedale (Leedale, 1974, *Taxon* 23:261-270) and other phycologists as part of the heterokont algae. However, as a matter of convenience resulting from their heterotrophic nature, the Oomycetes and Thraustochytrids have been largely studied by mycologists (scientists who study fungi) rather than phycologists (scientists who study algae).

From another taxonomic perspective, evolutionary biologists have developed two general schools of thought as to how eukaryotes evolved. One theory proposes an exogenous origin of membrane-bound organelles through a series of endosymbioses (Margulis, 1970, *Origin of Eukaryotic Cells*. Yale University Press, New Haven); e.g., mitochondria were derived from bacterial endosymbionts, chloroplasts from cyanophytes, and flagella from spirochaetes. The other theory suggests a gradual evolution of the membrane-bound organelles from the non-membrane-bounded systems of the prokaryote ancestor via an autogenous process (Cavalier-Smith, 1975, *Nature* (Lond.) 256:462-468). Both groups of evolutionary biologists however, have removed the Oomycetes and Thraustochytrids from the fungi and place them either with the chromophyte algae in the kingdom Chromophyta (Cavalier-Smith, 1981, *BioSystems* 14:461-481) (this kingdom has been more recently expanded to include other protists and members of this kingdom are now called Stramenopiles) or with all algae in the kingdom Protoctista (Margulis and Sagen, 1985, Biosystems 18:141-147).

With the development of electron microscopy, studies on the ultrastructure of the zoospores of two genera of Thraustochytrids, *Thraustochytrium* and *Schizochytrium*, (Perkins, 1976, pp. 279-312 in "Recent Advances in Aquatic Mycology" (ed. E. B. G. Jones), John Wiley & Sons, New York; Kazama, 1980, *Can. J. Bot.* 58:2434-2446; Barr, 1981, *Biosystems* 14:359-370) have provided good evidence that the Thraustochytriaceae are only distantly related to the Oomycetes. Additionally, genetic data representing a correspondence analysis (a form of multivariate statistics) of 5 S ribosomal RNA sequences indicate that Thraustochytriales are clearly a unique group of eukaryotes, completely separate from the fungi, and most closely related to the red and brown algae, and to members of the Oomycetes (Mannella, et al., 1987, *Mol. Evol.* 24:228-235). Most taxonomists have agreed to remove the Thraustochytrids from the Oomycetes (Bartnicki-Garcia, 1987, pp. 389-403 in "Evolutionary Biology of the Fungi" (eds. Rayner, A. D. M., Brasier, C. M. & Moore, D.), Cambridge University Press, Cambridge).

In summary, employing the taxonomic system of Cavalier-Smith (Cavalier-Smith, 1981, *BioSystems* 14:461-481, 1983; Cavalier-Smith, 1993, *MicrobiolRev.* 57:953-994), the Thraustochytrids are classified with the chromophyte algae in the kingdom Chromophyta (Stramenopiles). This taxonomic placement has been more recently reaffirmed by Cavalier-Smith et al. using the 18s rRNA signatures of the Heterokonta to demonstrate that Thraustochytrids are chromists not Fungi (Cavalier-Smith et al., 1994, *Phil. Tran. Roy. Soc. London Series BioSciences* 346:387-397). This places them in a completely different kingdom from the fungi, which are all placed in the kingdom Eufungi. The taxonomic placement of the Thraustochytrids is therefore summarized below:

Kingdom: Chromophyta (Stramenopiles)

Phylum: Heterokonta

Order: Thraustochytriales

Family: Thraustochytriaceae

Genus: *Thraustochytrium, Schizochytrium, Labyrinthuloides*, or *Japonochytrium*

Some early taxonomists separated a few original members of the genus *Thraustochytrium* (those with an amoeboid life stage) into a separate genus called *Ulkenia*. However it is now known that most, if not all, Thraustochytrids (including *Thraustochytrium* and *Schizochytrium*), exhibit amoeboid stages and as such, *Ulkenia* is not considered by some to be a valid genus. As used herein, the genus *Thraustochytrium* will include *Ulkenia*.

Despite the uncertainty of taxonomic placement within higher classifications of Phylum and Kingdom, the Thraustochytrids remain a distinctive and characteristic grouping whose members remain classifiable within the order Thraustochytriales.

Further embodiments of the present invention include nucleic acid molecules that encode a carotene synthase. An isolated nucleic acid molecule of the present invention includes a nucleic acid molecule comprising a nucleic acid sequence encoding any of the isolated carotene synthases, including a carotene synthase homologue or fragment, described above.

In one embodiment, such nucleic acid molecules include isolated nucleic acid molecules that hybridize under moderate stringency conditions, and even more preferably under high stringency conditions, and even more preferably under very high stringency conditions with the complement of a nucleic acid sequence encoding a naturally occurring carotene synthase (i.e., including naturally occurring allelic variants encoding a carotene synthase). Preferably, an isolated nucleic acid molecule encoding a carotene synthase of the present invention comprises a nucleic acid sequence that hybridizes under moderate, high, or very high stringency conditions to the complement of a nucleic acid sequence that encodes a protein comprising an amino acid sequence represented by SEQ ID NO:3, SEQ ID NO:5, SEQ ID NO:7 or SEQ ID NO:9. In one embodiment, an isolated nucleic acid molecule comprises a nucleic acid sequence that hybridizes under moderate, high or very high stringency conditions to the complement of a nucleic acid sequence represented by SEQ ID NO:1, SEQ ID NO:2, SEQ ID NO:4, SEQ ID NO:6 or SEQ ID NO:8. Such conditions have been described in detail above.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA, including cDNA. As such, "isolated" does not reflect the extent to which the nucleic acid molecule has been purified. An isolated carotene synthase nucleic acid molecule of the present invention can be isolated from its natural source or produced using recombinant DNA technology (e.g., polymerase chain reaction (PCR) amplification, cloning) or chemical synthesis. Isolated carotene synthase nucleic acid molecules can include, for example, carotene synthase genes, natural allelic variants of carotene synthase genes, carotene synthase coding regions or portions thereof, and carotene synthase coding and/or regulatory regions modified by nucleotide insertions, deletions, substitutions, and/or inversions in a manner such that the modifications do not substantially interfere with the nucleic acid molecule's ability to encode a carotene synthase protein of the present invention or to form stable hybrids under stringent conditions with natural gene isolates. An isolated carotene synthase nucleic acid molecule can include degeneracies. As used herein, nucleotide degeneracies refers to the phenomenon that one amino acid can be encoded by different nucleotide codons. Thus, the nucleic acid sequence of a nucleic acid molecule that encodes a carotene synthase protein of the present invention can vary due to degeneracies. It is noted that an isolated carotene synthase nucleic acid molecule of the present invention is not required to encode a protein having carotene synthase activity. A carotene synthase nucleic acid molecule can encode a truncated, mutated or inactive protein, for example. Such nucleic acid molecules and the proteins encoded by such nucleic acid molecules are useful in as probes and primers for the identification of other carotene synthases.

According to the present invention, reference to a carotene synthase gene includes all nucleic acid sequences related to a natural (i.e. wild-type) carotene synthase gene, such as regulatory regions that control production of the carotene synthase encoded by that gene (such as, but not limited to, transcription, translation or post-translation control regions) as well as the coding region itself. In another embodiment, a carotene synthase gene can be a naturally occurring allelic variant that includes a similar but not identical sequence to the nucleic acid sequence encoding a given carotene synthase. Allelic variants have been previously described above. The phrases "nucleic acid molecule" and "gene" can be used interchangeably when the nucleic acid molecule comprises a gene as described above.

A carotene synthase nucleic acid molecule homologue (i.e., encoding a carotene synthase homologue) can be produced using a number of methods known to those skilled in the art (see, for example, Sambrook et al.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Another method for modifying a recombinant nucleic acid molecule encoding a carotene synthase is gene shuffling (i.e., molecular breeding) (See, for example, U.S. Pat. No. 5,605,793 to Stemmer; Minshull and Stemmer; 1999, Curr. Opin. Chem. Biol. 3:284-290; Stemmer, 1994, P.N.A.S. USA 91:10747-10751, all of which are incorporated herein by reference in their entirety). This technique can be used to efficiently introduce multiple simultaneous changes in the carotene synthase action. Nucleic acid molecule homologues can be selected by hybridization with a carotene synthase gene or by screening the function of a protein encoded by a nucleic acid molecule (i.e., enzymatic activity).

One embodiment of the present invention relates to an oligonucleotide, comprising at least 12 contiguous nucleotides of a nucleic acid sequence selected from: SEQ ID NO:1, SEQ ID NO:2, SEQ ID NO:4, SEQ ID NO:6, SEQ ID NO:8, and a nucleic acid sequence fully complementary thereto. The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of an oligonucleotide probe or primer of the present invention, in that the probe or primer can include any portion of a carotene synthase gene of the invention that is suitable for the intended use, with probes typically being larger than primers. As such, an oligonucleotide of the invention can include any length fragment between about 12 and about 3800 nucleotides or even larger probes, in whole integers (e.g., 12, 13, 14, 15, 16 . . . 3799, 3800).

One embodiment of the present invention includes a recombinant nucleic acid molecule, which includes at least one isolated nucleic acid molecule of the present invention inserted into any nucleic acid vector (e.g., a recombinant vector) which is suitable for cloning, sequencing, and/or otherwise manipulating the nucleic acid molecule, such as expressing and/or delivering the nucleic acid molecule into a host cell to form a recombinant cell. Such a vector contains heterologous nucleic acid sequences, that is nucleic acid sequences that are not naturally found adjacent to nucleic acid molecules of the present invention, although the vector can also contain regulatory nucleic acid sequences (e.g., promoters, untranslated regions) which are naturally found adjacent to nucleic acid molecules of the present invention (discussed in detail below). The vector can be either RNA or DNA, either prokaryotic or eukaryotic, and typically is a virus or a plasmid. The vector can be maintained as an extrachromosomal element (e.g., a plasmid) or it can be integrated into the chromosome. The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. The vector can be designed for tissue-specific expression in the host cell, such as by using tissue-specific promoters. Several recombinant nucleic acid molecules useful in the present invention, including several recombinant vectors, are described in detail in the Examples.

Typically, a recombinant molecule includes a nucleic acid molecule of the present invention operatively linked to one or more transcription control sequences (e.g., promoters, operators, repressors, enhancers, terminators). As used herein, the phrase "recombinant molecule" or "recombinant nucleic acid molecule" primarily refers to a nucleic acid molecule or nucleic acid sequence operatively linked to a transcription control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to a transcription control sequence in a manner such that the molecule is able to be expressed when transformed (i.e., transformed, transduced, transfected, or conjugated) into a host cell. Transcription control sequences are sequences which control the initiation, elongation, or termination of transcription. Particularly important transcription control sequences are those which control transcription initiation, such as promoter, enhancer, operator and repressor sequences. Suitable transcription control sequences include any transcription control sequence that can function in at least one of the recombinant cells useful for expressing a carotene synthase of the present invention. A variety of such transcription control sequences are known to those skilled in the art. Preferred transcription control sequences include those which function in Thraustochytriales microorganisms, bacterial, fungal (e.g., yeast), or plant cells. Particularly preferred transcription control sequences for plants are those that promote gene expression in specific tissues (e.g., leaves, stems, roots, flowers, seeds) and can be referred to herein as tissue-specific transcription control sequences. Such sequences are well-known in the art.

In one embodiment of the invention, a suitable transcription control sequence includes the regulatory sequences that are naturally found in the carotene synthase gene of the present invention. For example, regulatory sequences of a *Schizochytrium* carotene synthase, which include a carotene synthase promoter, are found in nucleotides 1-1405 of SEQ ID NO:1 or in nucleotides 346-1405 of SEQ ID NO:1.

Recombinant molecules of the present invention, which can be either DNA or RNA, can also contain additional regulatory sequences, such as transcription regulatory sequences, translation regulatory sequences, origins of replication, and other regulatory sequences that are compatible with the recombinant cell. In one embodiment, a recombinant molecule of the present invention, including those which are integrated into the host cell chromosome, also contains signal (targeting) (i.e., signal segment nucleic acid sequences) to enable an expressed carotene synthase to be secreted from the cell that produces the protein or targeted to a particular organelle or membrane. For example, in one embodiment, suitable signal segments include a signal segment that is naturally associated with a carotene synthase of the present invention (e.g., amino acids 1-29 of SEQ ID NO:3) or any heterologous signal segment capable of directing the secretion of a carotene synthase according to the present invention. In another embodiment, a recombinant molecule of the present invention comprises a signal sequence to enable an expressed carotene synthase to be delivered to and inserted into the membrane of a host cell. Suitable signal sequences include a signal sequence that is naturally associated with a carotene synthase of the present invention, or any heterologous signal sequence capable of directing the delivery and insertion of a carotene synthase to the membrane of a cell. In another embodiment, a recombinant molecule of the present invention comprises a signal sequence which specifically targets the delivery of a carotene synthase to specific sub-cellular organelles or compartments, such as the endoplasmic reticulum, the chloroplast, the chromoplast, other plastids, or the cytoplasm.

One or more recombinant molecules of the present invention can be used to produce an encoded product (e.g., a carotene synthase) of the present invention. In one embodiment, an encoded product is produced by expressing a nucleic acid molecule as described herein under conditions effective to produce the protein. A preferred method to produce an encoded protein is by transforming a host cell with one or more recombinant molecules to form a recombinant cell. Suitable host cells to transform include, but are not limited to, any microalgal cell, including a Thraustochytriales microorganism, or any bacterial cell, fungal (e.g., yeast) cell, other microbial cell, or plant cell that can be transformed. Host cells can be either untransformed cells or cells that are already transformed with at least one nucleic acid molecule.

Preferred host cells for use in the present invention include any microorganism cell or plant cell which is suitable for expression of a carotene synthase of the present invention, including, but not limited to: (1) plants, including, but not limited to, crop plants (e.g., canola—*Brassica napus*, rice, corn, flax, safflower, soy, sunflower, rapeseed, linseed), tomatoes, and carrots; (2) fungi, including, but not limited to, *Phycomyces, Neurospora, Mucor, Blakeslea*, and yeast (e.g., *Saccaromyces cerevisiae, Phaffia rhodozyma, Xanthophyllomyces dendrohous, Candida utilus*); (3) algae, including but not limited to, green algae (e.g., *Haematococcus pluvialus, Chlorococcum, Spongiococcum, Neospongiococcum, Dunaliella*); (4) bacteria, including, but not limited to, blue-green (e.g., *Spirulina, Synechococcus, Synechocystis*), *Escherichia coli, Flavobacterium, Paracoccus, Erwinia, Agrobacterium, Rhodococcus*; and (5) members of the order, Thraustochytriales, including but not limited to: *Thraustochytrium* sp. (e.g., including former *Ulkenia* species such as *U. visurgensis, U. amoeboida, U. sarkariana, U. profunda, U. radiata, U. minuta* and *Ulkenia* sp. BP-5601, and including *Thraustochytrium striatum, Thraustochytrium aureum*, and *Thraustochytrium roseum*); *Labyrinthuloides, Japonochytrium* (e.g., *Japonochytrium* sp.), and *Schizochytrium* (e.g., *Schizochytrium* sp., *Schizochytrium aggregatum, Schizochytrium limacinum, Schizochytrium minutum*).

According to the present invention, the term "transformed" or "transformation" is used to refer to any method by which an exogenous nucleic acid molecule (i.e., a recombinant nucleic acid molecule) can be inserted into the cell. In microbial systems, the term "transformation" is used to describe an inherited change due to the acquisition of exogenous nucleic acids by the microorganism and can be essentially synonymous with the term "transfection", which is more commonly used in reference to the similar process in animal cells. The term "transformation" is preferably used herein to refer to the introduction of nucleic acid molecules into microbial cells, such as bacteria and yeast, or into plant cells. Therefore, transformation techniques include, but are not limited to, transfection, electroporation, microinjection, lipofection, biolistic methods (particle bombardment), adsorption, *Agrobacterium*-mediated transformation, infection and protoplast fusion. Methods of transforming prokaryotic and eukaryotic host cells are well known in the art. See, e.g., Maniatis et al., *Molecular Cloning: A Laboratory Manual*, Cold Spring Harbor, N.Y. (1982), Sambrook et al., *Molecular Cloning: A*

*Laboratory Manual*, Cold Spring Harbor, N.Y. (1989), incorporated herein by reference in its entirety. A preferred method for transforming members of the order Thraustochytriales is described in U.S. patent application Ser. No. 10/124,807, filed Apr. 16, 2002, incorporated by reference in its entirety.

Numerous methods for plant transformation have been developed, including biological and physical transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pp. 67-88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pp. 89-119.

The most widely utilized method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.* 10:1 (1991). Descriptions of *Agrobacterium* vector systems and methods for *Agrobacterium*-mediated gene transfer are provided by numerous references, including Gruber et al., supra, Miki et al., supra, Moloney et al., *Plant Cell Reports* 8:238 (1989), and U.S. Pat. Nos. 4,940,838 and 5,464,763, each of which is incorporated herein by reference in its entirety.

A generally applicable method of plant transformation is microprojectile-mediated transformation wherein DNA is carried on the surface of microprojectiles. The expression vector is introduced into plant tissues with a biolistic device that accelerates the microprojectiles to speeds sufficient to penetrate plant cell walls and membranes. Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992), each of which is incorporated herein by reference in its entirety.

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. USA* 84:3962 (1987), each of which is incorporated herein by reference in its entirety. Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982), each of which is incorporated herein by reference in its entirety. Electroporation of protoplasts and whole cells and tissues have also been described. Donn et al., In Abstracts of VIIth International Congress on Plant Cell and Tissue Culture IAPTC, A2-38, p. 53 (1990); D'Halluin et al., *Plant Cell* 4:1495-1505 (1992) and Spencer et al., *Plant Mol. Biol.* 24:51-61 (1994), each of which is incorporated herein by reference in its entirety.

In one embodiment, an isolated carotene synthase of the present invention is produced by culturing a cell that expresses the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a carotene synthase of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant host cell; be secreted into the culture medium; be secreted into a space between two cellular membranes, such as the periplasmic space in *E. coli*; or be retained on the outer surface of a cell membrane. The phrase "recovering the protein" refers to collecting the whole culture medium containing the protein and need not imply additional steps of separation or purification. Proteins of the present invention can be purified, if desired, using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. If proteins of the present invention are purified, they are preferably retrieved in "substantially pure" form. As used herein, "substantially pure" refers to a purity that allows for the effective use of the protein as a biocatalyst or other reagent.

To produce significantly high yields of carotenoids by the methods of the present invention, a microorganism or plant (or part of a plant, e.g., seeds, pollen, embryos, flowers, fruits, shoots, leaves, roots, stems, explants, etc.) can be genetically modified to increase the action of carotene synthase, and preferably, to enhance production of carotene synthase, and thereby, a carotenoid endproduct. In one embodiment of the invention, a microorganism that contains an endogenous carotene synthase of the invention (e.g., *Schizochytrium*) is genetically modified to increase or reduce the expression and activity of the carotene synthase.

As used herein, a genetically modified microorganism, such as a genetically modified bacterium, protist, microalga, fungus, or other microbe, and particularly, any member of the genera of the order Thraustochytriales (e.g., a Thraustochytrid) described herein (e.g., *Schizochytrium, Thraustochytrium, Japonochytrium, Labyrinthuloides*), has a genome which is modified (i.e., mutated or changed) from its normal (i.e., wild-type or naturally occurring) form such that the desired result is achieved (i.e., increased or modified carotene synthase expression and/or activity and/or production of a desired product using the carotene synthase). Genetic modification of a microorganism can be accomplished using classical strain development and/or molecular genetic techniques. Such techniques are generally disclosed for microorganisms, for example, in Sambrook et al., 1989, supra, incorporated by reference herein in its entirety. A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism.

Preferred microorganism host cells to modify according to the present invention include, but are not limited to, any bacteria, protist, microalga, fungus, or protozoa. In one aspect, preferred microorganisms to genetically modify include, but are not limited to, any microorganism of the order Thraustochytriales. Particularly preferred host cells for use in the present invention could include microorganisms from a genus including, but not limited to: *Thraustochytrium, Labyrinthuloides, Japonochytrium*, and *Schizochytrium*. Preferred species within these genera include, but are not limited to: any *Schizochytrium* species, including *Schizochytrium aggregatum, Schizochytrium limacinum, Schizochytrium minutum*; any *Thraustochytrium* species (including former *Ulkenia* species such as *U. visurgensis, U. amoeboida, U. sarkariana, U. profunda, U. radiata, U. minuta* and *Ulkenia* sp. BP-5601), and including *Thraustochytrium striatum, Thraustochytrium aureum, Thraustochytrium roseum*; and any *Japonochytrium* species. Particularly preferred strains of Thraustochytriales include, but are not limited to: *Schizochytrium* sp. (S31) (ATCC 20888); *Schizochytrium* sp. (S8)(ATCC 20889); *Schizochytrium* sp. (LC-RM)(ATCC 18915); *Schizochytrium* sp. (SR21); *Schizochytrium aggregatum* (Goldstein et Belsky) (ATCC 28209); *Schizochytrium limacinum* (Honda et Yokochi)(IFO 32693); *Thraustochytrium* sp. (23B)(ATCC 20891); *Thraustochytrium striatum* (Schneider) (ATCC 24473); *Thraustochytrium aureum* (Goldstein)(ATCC 34304); *Thraustochytrium roseum* (Goldstein)(ATCC 28210); and *Japonochytrium* sp. (L1) (ATCC 28207). Other examples of suitable host microorganisms for genetic modification include, but are not limited to, yeast including *Saccharomyces cerevisiae, Saccharomyces carlsbergensis*, or other yeast such as *Candida, Kluyveromyces*, or other fungi, for example, filamentous fungi such as *Aspergillus, Neurospora, Penicillium*, etc. Bacterial cells also may be used as hosts. This includes *Escherichia coli*, which can be useful in fermentation processes. Alternatively, a host such as a *Lactobacillus* species or *Bacillus* species can be used as a host.

As used herein, a genetically modified plant can include any genetically modified plant including higher plants and particularly, any consumable plants or plants useful for producing a desired product of the present invention (e.g., carotenoids or any other lipid product). Such a genetically modified plant has a genome which is modified (i.e., mutated or changed) from its normal (i.e., wild-type or naturally occurring) form such that the desired result is achieved (i.e., increased or modified carotene synthase expression and/or activity and/or production of a desired product using the carotene synthase). Genetic modification of a plant can be accomplished using classical strain development and/or molecular genetic techniques. Methods for producing a transgenic plant, wherein a recombinant nucleic acid molecule encoding a desired amino acid sequence is incorporated into the genome of the plant, are known in the art and have been described briefly above. A preferred plant to genetically modify according to the present invention is preferably a plant suitable for consumption by animals, including humans.

Preferred plants to genetically modify according to the present invention (i.e., plant host cells) include, but are not limited to any higher plants, and particularly consumable plants, including crop plants and especially plants used for their oils. Such plants can include, for example: canola, soybeans, rapeseed, linseed, corn, safflowers, flax, sunflowers, tobacco, rice, tomatoes and carrots. Other preferred plants include those plants that are known to produce compounds used as pharmaceutical agents, flavoring agents, neutraceutical agents, functional food ingredients or cosmetically active agents or plants that are genetically engineered to produce these compounds/agents.

According to the present invention, a genetically modified microorganism or plant includes a microorganism or plant that has been modified using recombinant technology. As used herein, genetic modifications which result in a decrease in gene expression, in the function of the gene, or in the function of the gene product (i.e., the protein encoded by the gene) can be referred to as inactivation (complete or partial), deletion, interruption, blockage or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). Genetic modifications which result in an increase in gene expression or function can be referred to as amplification, overproduction, overexpression, activation, enhancement, addition, or up-regulation of a gene.

In one embodiment of the present invention, a genetic modification of a microorganism or plant increases or decreases the expression and/or activity of a carotene synthase of the present invention. Such a genetic modification includes any type of modification and specifically includes modifications made by recombinant technology and/or by classical mutagenesis. It should be noted that reference to increasing the action (activity) of carotene synthase refers to any genetic modification in the microorganism or plant in question and/or in the recombinant nucleic acids containing the carotene synthase-encoding DNA with which the organism is transformed that results in increased functionality of the enzyme and can include higher activity of the enzyme (e.g., specific activity or in vivo enzymatic activity), reduced inhibition or degradation of the enzyme, and overexpression of the enzyme. For example, gene copy number can be increased, expression levels can be increased by use of a promoter that gives higher levels of expression than that of the native promoter, or a gene can be altered by genetic engineering or classical mutagenesis to increase the action of an enzyme. In one aspect, carotene synthase activity or expression can be modified by modifying a nucleic acid or protein that interacts with a carotene synthase gene or protein and normally modulates the expression or activity of the carotene synthase gene or protein. Such a modification can be achieved by recombinant or classical mutational techniques.

Similarly, reference to decreasing the action (activity) of a carotene synthase refers to any genetic modification in the microorganism or plant in question and/or in the recombinant nucleic acids containing the carotene synthase-encoding DNA with which the organism is transformed that results in decreased functionality of the enzymes and includes decreased activity of the enzymes (e.g., specific activity), increased inhibition or degradation of the enzymes and a reduction or elimination of expression of the enzyme. For example, the action of a carotene synthase of the present invention can be decreased by blocking or reducing the production of the enzyme, "knocking out" all or a portion of the gene encoding the enzyme, reducing enzyme activity, or inhibiting the activity of the enzyme (any one, two or three of the enzymatic activities of a carotene synthase of the invention). Blocking or reducing the production of an enzyme can include placing the gene encoding the enzyme under the control of a promoter that requires the presence of an inducing compound in the growth medium. By establishing conditions such that the inducer becomes depleted from the medium, the expression of the gene encoding the enzyme (and therefore, of enzyme synthesis) could be turned off. Blocking or reducing the activity of an enzyme could also include using an excision technology approach similar to that described in U.S. Pat. No. 4,743,546, incorporated herein by reference in its entirety. To use this approach, the gene encoding the enzyme of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal. Deletion of all or a portion of a carotene synthase gene of the invention using homologous recombination techniques are described in the Examples. In one embodiment, one or two of the enzymatic domains of the CS of the present invention (e.g., PD, PS, LC) can be knocked out in order to produce a desired product. For example, knocking out the LC domain of the CS enzyme should lead to the production of lycopene. Such a gene would effectively be a PD/PS bi-functional enzyme, a combination previously unknown to the inventors. Lycopene may itself be a desirable product. Additionally, lycopene could serve as substrate for other potentially desirable products such as α-carotene and lutein.

In one embodiment of the present invention, it is contemplated that a mutagenesis program could be combined with a selective screening process to obtain microorganisms of interest. The mutagenesis methods could include, but are not limited to: chemical mutagenesis, gene shuffling, switching regions of the genes encoding specific enzymatic domains, or mutagenesis restricted to specific regions of those genes, as well as other methods. For example, high throughput mutagenesis methods could be used to influence or optimize production of the desired carotenoids or other lipid products. Such methods could be combined with selective (i.e., targeted or directed) modification of the carotene synthase by molecular biology techniques. For example, one could use selective modification techniques to modify a microorganism, for example, by introduction of a recombinant nucleic acid molecule encoding the carotene synthase of the invention into any suitable host cell, including host cells comprising an endogenous carotene synthase, and then use mutagenesis technologies to optimize carotenoid production and to create strains having improved carotenoid synthesis activity or to select for microorganisms with other improved or desired qualities. Screening methods are also useful for identifying other organisms having homologous carotene synthase genes to the carotene synthase of Schizochytrium. Homologous CS genes identified in such organisms can be used in methods similar to those described herein.

In one embodiment of the present invention, a genetically modified microorganism or plant includes a microorganism or plant which has an enhanced ability to synthesize carotenoids in general or an enhanced ability to synthesize specific carotenoids (i.e. to change the profile of specific carotenoids produced by the organism). According to the present invention, "an enhanced ability to synthesize" a product refers to any enhancement, or up-regulation, in a pathway related to the synthesis of the product such that the microorganism or plant produces an increased amount of the product compared to the wild-type microorganism or plant, cultured or grown, under the same conditions. In one embodiment of the present invention, enhancement of the ability of a microorganism or plant to synthesize carotenoids is accomplished by amplification of the expression of the carotene synthase gene. Amplification of the expression of carotene synthase can be accomplished in any suitable host cell (e.g., a Thraustochytriales cell, a bacterial cell, a yeast cell, a plant cell), for example, by introduction of a recombinant nucleic acid molecule encoding the carotene synthase gene, or by modifying regulatory control over a native carotene synthase gene, in the case of Thraustochytriales.

According to the present invention, "selective modification" of an organism or nucleic acid molecule refers to a targeted, or directed, modification, where the modification to be made is predetermined and designed, for example, by knowledge of the gene structure of the carotene synthase of the present invention. For example, selective modification of an organism can be achieved by introduction (e.g., overexpression) of a recombinant nucleic acid molecule encoding a carotene synthase, or by targeted modification of an endogenous gene, such as by homologous recombination. Selective modification is distinguished from random mutagenesis techniques, where in the latter process, the mutation is randomly generated by a non-target-specific method and the desired phenotype is subsequently selected through screening of mutants for the phenotype. Selective modification techniques and classical random mutagenesis and screening techniques can be combined in the present invention to produce a variety of genetically modified organisms.

Therefore, it is an embodiment of the present invention to provide a microorganism or plant which is transformed with a recombinant nucleic acid molecule comprising a nucleic acid sequence encoding a carotene synthase. Preferred recombinant nucleic acid molecules comprising such a nucleic acid sequence include recombinant nucleic acid molecules comprising any of the carotene synthase nucleic acid sequences previously described herein. It is one embodiment of the present invention to provide a microorganism or plant which is transformed with a genetically modified recombinant nucleic acid molecule comprising a nucleic acid sequence encoding a mutant, or homologue, carotene synthase. Such carotene synthases can be referred to herein as carotene synthase homologues, and can include any one, two or three of the enzymatic activities of the native carotene synthase described herein. Protein homologues have been described in detail herein.

It is another embodiment of the present invention to provide a genetically modified microorganism for producing a carotenoid by a biosynthetic process, wherein the microorganism comprises a nucleic acid molecule encoding a carotene synthase and wherein the nucleic acid molecule encoding the carotene synthase has been modified to increase the expression or biological activity of the carotene synthase. The carotene synthase can be any carotene synthase described herein, including homologues and biologically active fragments as described herein. In one aspect of the invention, the microorganism has an endogenous carotene synthase (e.g., a member of Thraustochytriales), and the endogenous gene is modified to increase the expression or activity of the carotene synthase (e.g., by introducing a promoter that gives higher levels of expression than that of the native promoter, by genetically mutating the endogenous gene to increase the activity of the enzyme, etc.). In another embodiment, the microorganism is genetically modified by transformation with a recombinant nucleic acid molecule encoding a carotene synthase of the invention. Such a microorganism can be any suitable host microorganism and in one embodiment, is a Thraustochytriales microorganism (e.g., a Schizochytrium), such that the microorganism comprises both an endogenous carotene synthase and a recombinant carotene synthase. The carotene synthases in this scenario need not be identical, since one or both of the endogenous and recombinant carotene synthases can be modified as compared to a wild-type

*Schizochytrium* carotene synthase disclosed herein to produce a carotene synthase homologue. For example, one or both of the endogenous or recombinant carotene synthases can be modified to increase the expression or activity of the carotene synthase.

Accordingly, one embodiment of the invention is a biomass comprising any of the microorganisms described herein comprising a nucleic acid molecule encoding a carotene synthase that has been modified to increase the expression or biological activity of the carotene synthase as described above. As used herein, a biomass refers to a population of microbial cells that have been harvested from a fermentation or culture process. Various fermentation parameters for inoculating, growing and recovering microfloral biomasses are discussed in detail in U.S. Pat. No. 5,130,242, incorporated herein by reference in its entirety. The biomass harvested from a fermentation run can be dried (e.g., spray drying, tunnel drying, vacuum drying, or a similar process) and used in any food, pharmaceutical or other desired product. Alternatively, the harvested and washed biomass can be used directly (without drying) in various products. To extend its shelf life, the wet biomass can be acidified (approximate pH=3.5-4.5) and/or pasteurized or flash heated to inactivate enzymes and then canned, bottled or packaged under a vacuum or non-oxidizing atmosphere (e.g., $N_2$ or $CO_2$).

One embodiment of the present invention is a method to produce a carotenoid by a biosynthetic process, comprising culturing in a fermentation medium a genetically modified microorganism that has increased expression or biological activity of a carotene synthase as described above. For example, the microorganism can have increased expression or biological activity of any carotene synthase proteins described herein, including homologues and enzymatically active portions thereof. The carotene synthase can be an endogenous carotene synthase and/or a recombinant carotene synthase according to the invention. The microorganism is cultured or grown in a suitable medium, under conditions effective to produce the desired carotenoid or other lipid product. An appropriate, or effective, medium refers to any medium in which a genetically modified microorganism of the present invention, when cultured, is capable of producing the desired product. Such a medium is typically an aqueous medium comprising assimilable carbon, nitrogen and phosphate sources. Such a medium can also include appropriate salts, minerals, metals and other nutrients. Microorganisms of the present invention can be cultured in conventional fermentation bioreactors. The microorganisms can be cultured by any fermentation process which includes, but is not limited to, batch, fed-batch, cell recycle, and continuous fermentation. Preferred growth conditions for potential host microorganisms according to the present invention are well known in the art. The desired products produced by the genetically modified microorganism can be recovered from the fermentation medium using conventional separation and purification techniques. For example, the fermentation medium can be filtered or centrifuged to remove microorganisms, cell debris and other particulate matter, and the product can be recovered from the cell-free supernatant by conventional methods, such as, for example, ion exchange, chromatography, extraction, solvent extraction, membrane separation, electrodialysis, reverse osmosis, distillation, chemical derivatization and crystallization. Alternatively, microorganisms producing the desired product, or extracts and various fractions thereof, can be used without removal of the microorganism components from the product, such as in a biomass of the invention.

One embodiment of the present invention is a method to produce carotenoids by growing or culturing a genetically modified plant of the present invention as previously described herein. Such a method includes the step of culturing in a fermentation medium or growing in a suitable environment, such as soil, a plant having a genetic modification to increase the action of carotene synthase. Preferably, the genetic modification includes transformation or transfection of the plant with a recombinant nucleic acid molecule that expresses a protein having carotene synthase biological activity. Such a protein can include any of the carotene synthases described herein, including any homologue of a naturally occurring carotene synthase having biological activity.

In the method for production of carotenoids of the present invention, a plant that has a genetic modification to increase the action of carotene synthase is cultured in a fermentation medium or grown in a suitable medium such as soil for production of carotene synthase. An appropriate, or effective, fermentation medium has been discussed in detail above. A suitable growth medium for higher plants includes any growth medium for plants, including, but not limited to, soil, sand, any other particulate media that support root growth (e.g. vermiculite, perlite, etc.) or Hydroponic culture, as well as suitable light, water and nutritional supplements which optimize the growth of the higher plant. The genetically modified plants of the present invention are engineered to produce significant quantities of carotenoids through increased action of carotene synthase. The carotenoids can be recovered through purification processes which extract the carotenoids from the plant. In a preferred embodiment, the carotenoid is recovered by harvesting the plant or plant fraction (e.g., seeds). In this embodiment, the plant or plant fraction can be consumed in its natural state or further processed into consumable products.

Another embodiment of the invention relates to a genetically modified microorganism lacking pigmentation, wherein the microorganism has been genetically modified to selectively delete or inactivate a carotene synthase gene or portion thereof encoding a functional domain (e.g., any one, two or three of the functional enzymatic domains of a carotene synthase of the invention—PD, PS and/or LC). The carotene synthase gene includes the carotene synthase-encoding nucleic acid molecules as described previously herein. In a preferred embodiment, the microorganism is a microalga, and in a more preferred embodiment, is a Thraustochytriales microorganism (e.g., a *Schizochytrium*). The carotene synthase gene can be modified by modification to the coding region of the carotene synthase gene or to a regulatory region of the carotene synthase gene, such that expression and/or biological activity of the carotene synthase gene is reduced, and preferably inhibited so that the microorganism lacks pigmentation. In one embodiment the carotene synthase gene is partially or completely deleted or inactivated, including by replacing the gene with a non-CS nucleic acid sequence, such as by gene disruption through homologous recombination. In this aspect, the carotene synthase gene is mutated or inactivated (or deleted) by targeted homologous recombination with a nucleic acid sequence that hybridizes to the carotene synthase gene which includes a heterologous nucleic acid sequence that disrupts the coding region of the carotene synthase gene (see Examples).

Production of a colorless (non-pigmented) microorganism has commercial benefits. First, microorganisms that contain a carotene synthase include members of Thraustochytriales, which are known to be valuable organisms for the production of lipids containing high levels of polyunsaturated fatty acids (PUFAs), including highly unsaturated fatty acids such as omega-3 fatty acids. PUFAs include any omega-3 or omega-6 polyunsaturated fatty acids with three or more double bonds.

Omega-3 PUFAs are polyethylenic fatty acids in which the ultimate ethylenic bond is three carbons from and including the terminal methyl group of the fatty acid and include, for example, docosahexaenoic acid C22:6(n-3) (DHA), eicosapentaenoic acid C20:5(n-3) (EPA), omega-3 docosapentaenoic acid C22:5(n-3) (DPAn-3), stearidonic acid C18:4(n-3) (SDA), and linolenic acid C18:3(n-3) (LNA). Omega-6 PUFAs are polyethylenic fatty acids in which the ultimate ethylenic bond is six carbons from and including the terminal methyl group of the fatty acid and include, for example, arachidonic acid C20:4(n-6) (ARA), C22:4(n-6), omega-6 docosapentaenoic acid C22:5(n-6) (DPAn-6), gammalinolenic acid C18:3(n-6) (GLA) and dihomogammalinolenic acid C20:3(n-6) (dihomo GLA). The PUFAs can be in any of the common forms found in natural lipids including free fatty acids and compounds comprising PUFA residues, including phospholipids; esters of fatty acids; triacylglycerols; diacylglycerides; monoacylglycerides; lysophospholipids; phosphatides; etc. Polyunsaturated fatty acids (PUFAs) are considered to be useful for nutritional, pharmaceutical, industrial, and other purposes. An expansive supply of PUFAs from natural sources and from chemical synthesis are not sufficient for commercial needs. Members of Thraustochytriales, such as *Schizochytrium*, accumulate large quantities of triacylglycerols rich in PUFAs. For example, *Schizochytrium* can be cultured to produce significant quantities of docosahexaenoic acid (DHA; 22:6ω3) and docosapentaenoic acid (DPA; 22:5 ω-6); e.g., 30% DHA+DPA by dry weight (Barclay et al., *J. Appl. Phycol.* 6, 123 (1994)). Other PUFAs, including valuable omega-3 fatty acids, can be produced using organisms such as Thraustochytriales members, by genetically modifying the PUFA production profile of the microorganism, which is the subject of U.S. patent application Ser. No. 10/124,800, filed Apr. 16, 2002, entitled "PUFA Polyketide Synthase Systems and Uses Thereof", incorporated herein by reference in its entirety.

The lipid products of microorganisms such as members of Thraustochytriales are typically colored due to the presence of the carotenoid synthesis pathway. Since the lipid products are useful in a variety of food and other commercial products, it would be useful to produce a colorless, or non-pigmented microorganism and lipid product, which would be aesthetically desirable in some applications. In addition, and without being bound by theory, there are published reports that indicate that carotenoids such as β-carotene can act as pro-oxidants under some conditions (e.g., Beutner et al., *J. Sci. Food Agric.* 81, 559 (2001)). Therefore, reduction in the production of β-carotene and other carotenoids by a microorganism used for production of a commercial product may increase the stability of the lipid product derived therefrom.

Accordingly, another embodiment of the invention relates to a biomass comprising genetically modified microorganism (e.g., a microorganism of the order Thraustochytriales (e.g., *Schizochytrium, Thraustochytrium*)) that have reduced pigmentation as compared to a wild-type microorganism of the same species, as described above. Also included in the invention are lipids lacking pigmentation that are recovered from a culture of genetically modified microorganisms (e.g., of the order Thraustochytriales), wherein the microorganisms have been genetically modified to selectively delete or inactivate a carotene synthase gene as described above. It is to be understood that organisms other than Thraustochytriales may be discovered which contain a carotene synthase having homology to the carotene synthase described herein. Such microorganisms can also be modified to reduce the expression or activity of the carotene synthase, particularly if such microorganisms or products produced by such microorganisms are useful, such as in a commercial product. Also included in the invention are products comprising the biomass or lipids lacking pigmentation, such as food products or pharmaceutical products and other products that make use of lipids produced by the invention.

As used herein, the term "lipid" includes phospholipids; free fatty acids; esters of fatty acids; mono-, di- and triacylglycerols; sterols and sterol esters; carotenoids; xanthophylls (e.g., oxycarotenoids); hydrocarbons (e.g., waxes); isoprenoid-derived compounds and other lipids known to one of skill in the art. A food product, as used herein, includes any food ingredient (e.g., a food product that is part of another food product, such as an oil), and also includes, but is not limited to: fine bakery wares, bread and rolls, breakfast cereals, processed and unprocessed cheese, condiments (ketchup, mayonnaise, etc.), dairy products (milk, yoghurt), puddings and gelatine desserts, carbonated drinks, teas, powdered beverage mixes, processed fish products, fruit-based drinks, chewing gum, hard confectionery, frozen dairy products, processed meat products, nut and nut-based spreads, pasta, processed poultry products, gravies and sauces, potato chips and other chips or crisps, chocolate and other confectionery, soups and soup mixes, soya based products (milks, drinks, creams, whiteners), vegetable oil-based spreads, and vegetable-based drinks. Other products include dietary supplements, a pharmaceutical formulations, humanized animal milk, and infant formulas. Suitable pharmaceutical formulations include, but are not limited to, an anti-inflammatory formulation, a chemotherapeutic agent, an active excipient, an osteoporosis drug, an anti-depressant, an anti-convulsant, an anti-*Heliobactor pylori* drug, a drug for treatment of neurodegenerative disease, a drug for treatment of degenerative liver disease, an antibiotic, a cholesterol lowering formulation, and products used to treat a condition selected from the group consisting of: chronic inflammation, acute inflammation, gastrointestinal disorder, cancer, cachexia, cardiac restenosis, neurodegenerative disorder, degenerative disorder of the liver, blood lipid disorder, osteoporosis, osteoarthritis, autoimmune disease, preeclampsia, preterm birth, age related maculopathy, pulmonary disorder, and peroxisomal disorder.

Therefore, another embodiment of the present invention relates to a method for producing lipids lacking pigmentation from a biosynthetic process, comprising culturing under conditions effective to produce the lipids genetically modified microorganisms (e.g., of the order Thraustochytriales) as previously described herein, wherein the microorganisms have been genetically modified to selectively delete or inactivate a carotene synthase gene as described above. The lipids can be recovered using any one of a variety of recovery techniques known in the art or the entire microorganism or extracts thereof can be recovered. One aspect of the invention relates to a method for recovering lipids lacking pigmentation from a biosynthetic process, comprising recovering lipids from a culture of genetically modified microorganisms (e.g., of the order Thraustochytriales), wherein the microorganisms have been genetically modified to selectively delete or inactivate a carotene synthase gene as described above. Techniques for recovery of lipids from the culture are known in the art and include, but are not limited to, ion exchange, chromatography, extraction, solvent extraction, phase separation, membrane separation, electrodialysis, reverse osmosis, distillation, chemical derivatization and crystallization.

Another embodiment of the present invention is a method for producing carotenoids or derivatives thereof using an isolated carotene synthase, including a homologue of a carotene synthase as described herein. The method can be operated in batch or continuous mode using a stirred tank, a plug-flow column reactor or other apparatus known to those skilled in the art.

In one embodiment, the carotene synthase is bound to a solid support, i.e., an immobilized enzyme. As used herein, a carotene synthase bound to a solid support (i.e., an immobilized carotene synthase) includes immobilized isolated carotene synthase, immobilized cells which contain a carotene synthase enzyme (including immobilized Thraustochytriales, bacterial, fungal (e.g., yeast), microalgal, or plant cells), stabilized intact cells and stabilized cell/membrane homogenates. Stabilized intact cells and stabilized cell/membrane homogenates include cells and homogenates from naturally occurring microorganisms expressing carotene synthase or from genetically modified microorganisms or plants as disclosed elsewhere herein. Thus, although methods for immobilizing carotene synthase are discussed below, it will be appreciated that such methods are equally applicable to immobilizing cells and in such an embodiment, the cells can be lysed.

A variety of methods for immobilizing an enzyme are disclosed in Industrial Enzymology 2nd Ed., Godfrey, T. and West, S. Eds., Stockton Press, New York, N.Y., 1996, pp. 267-272; Immobilized Enzymes, Chibata, I. Ed., Halsted Press, New York, N.Y., 1978; Enzymes and Immobilized Cells in Biotechnology, Laskin, A. Ed., Benjamin/Cummings Publishing Co., Inc., Menlo Park, Calif., 1985; and Applied Biochemistry and Bioengineering, Vol. 4, Chibata, I. and Wingard, Jr., L. Eds, Academic Press, New York, N.Y., 1983, which are incorporated herein in their entirety.

Briefly, a solid support refers to any solid organic supports, artificial membranes, biopolymer supports, or inorganic supports that can form a bond with carotene synthase (or cell) without significantly effecting the activity of isolated carotene synthase. Exemplary organic solid supports include polymers such as polystyrene, nylon, phenol-formaldehyde resins, acrylic copolymers (e.g., polyacrylamide), stabilized intact whole cells, and stabilized crude whole cell/membrane homogenates. Exemplary biopolymer supports include cellulose, polydextrans (e.g., Sephadex®), agarose, collagen and chitin. Exemplary inorganic supports include glass beads (porous and nonporous), stainless steel, metal oxides (e.g., porous ceramics such as $ZrO_2$, $TiO_2$, $Al_2O_3$, and NiO) and sand. Preferably, the solid support is selected from the group consisting of stabilized intact cells and/or crude cell homogenates. Preparation of such supports requires a minimum of handling and cost. Additionally, such supports provide excellent stability of the enzyme.

Stabilized intact cells and/or cell/membrane homogenates can be produced, for example, by using bifunctional crosslinkers (e.g., glutaraldehyde) to stabilize cells and cell homogenates. In both the intact cells and the cell membranes, the cell wall and membranes act as immobilizing supports. In such a system, integral membrane proteins are in the "best" lipid membrane environment. Whether starting with intact cells or homogenates, in this system the cells are either no longer "alive" or "metabolizing", or alternatively, are "resting" (i.e., the cells maintain metabolic potential and active carotene synthase, but under the culture conditions are not growing); in either case, the immobilized cells or membranes serve as biocatalysts.

Carotene synthase can be bound to a solid support by a variety of methods including adsorption, cross-linking (including covalent bonding), and entrapment. Adsorption can be through van del Waal's forces, hydrogen bonding, ionic bonding, or hydrophobic binding. Exemplary solid supports for adsorption immobilization include polymeric adsorbents and ion-exchange resins. Solid supports in a bead form are particularly well-suited. The particle size of an adsorption solid support can be selected such that the immobilized enzyme is retained in the reactor by a mesh filter while the substrate (e.g., the precursor or substrate used as a starting material to produce the desired carotenoid) is allowed to flow through the reactor at a desired rate. With porous particulate supports it is possible to control the adsorption process to allow carotene synthase or microorganism cells to be embedded within the cavity of the particle, thus providing protection without an unacceptable loss of activity.

Cross-linking of a carotene synthase to a solid support involves forming a chemical bond between a solid support and a carotene synthase. It will be appreciated that although cross-linking generally involves linking a carotene synthase to a solid support using an intermediary compound, it is also possible to achieve a covalent bonding between the enzyme and the solid support directly without the use of an intermediary compound. Cross-linking commonly uses a bifunctional or multifunctional reagent to activate and attach a carboxyl group, amino group, sulfur group, hydroxy group or other functional group of the enzyme to the solid support. The term "activate" refers to a chemical transformation of a functional group which allows a formation of a bond at the functional group. Exemplary amino group activating reagents include water-soluble carbodiimides, glutaraldehyde, cyanogen bromide, N-hydroxysuccinimide esters, triazines, cyanuric chloride, and carbonyl diimidazole. Exemplary carboxyl group activating reagents include water-soluble carbodiimides, and N-ethyl-5-phenylisoxazolium-3-sulfonate. Exemplary tyrosyl group activating reagents include diazonium compounds. And exemplary sulfhydryl group activating reagents include dithiobis-5,5'-(2-nitrobenzoic acid), and glutathione-2-pyridyl disulfide. Systems for covalently linking an enzyme directly to a solid support include Eupergit®, a polymethacrylate bead support available from Rohm Pharma (Darmstadt, Germany), kieselguhl (Macrosorbs), available from Sterling Organics, kaolinite available from English China Clay as "Biofix" supports, silica gels which can be activated by silanization, available from W.R. Grace, and high-density alumina, available from UOP (Des Plaines, Ill.).

Entrapment can also be used to immobilize carotene synthase. Entrapment of carotene synthase involves formation of, inter alia, gels (using organic or biological polymers), vesicles (including microencapsulation), semipermeable membranes or other matrices. Exemplary materials used for entrapment of an enzyme include collagen, gelatin, agar, cellulose triacetate, alginate, polyacrylamide, polystyrene, polyurethane, epoxy resins, carrageenan, and egg albumin. Some of the polymers, in particular cellulose triacetate, can be used to entrap the enzyme as they are spun into a fiber. Other materials such as polyacrylamide gels can be polymerized in solution to entrap the enzyme. Still other materials such as polyglycol oligomers that are functionalized with polymerizable vinyl end groups can entrap enzymes by forming a cross-linked polymer with UV light illumination in the presence of a photosensitizer.

Carotenoids produced by any method of the present invention described herein can be recovered by conventional methods. Preferred carotenoids to produce using any of the methods of the present invention include, but are not limited to: β-carotene, astaxanthin, canthaxanthin, hydroxy-canthaxanthin, zeaxanthin, β-cryptoxanthin, echinenone, violaxanthin, α-carotene, lutein, lycopene, and esters and glucosides of any of the above-mentioned carotenoids.

The present invention also includes isolated (i.e., removed from their natural milieu) antibodies, or antigen binding fragments thereof, that are capable of selectively binding to a carotene synthase of the present invention (e.g., carotene synthase antibodies). The phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.). Antibodies of the present invention can be polyclonal or monoclonal, functional equivalents such as antibody fragments and genetically-engineered antibodies, including single chain antibodies or chimeric antibodies, including bi-specific antibodies that can bind to more than one epitope.

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies may be produced according to the methodology of Kohler and Milstein (*Nature* 256:495-497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

Genetically engineered antibodies of the invention include those produced by standard recombinant DNA techniques involving the manipulation and re-expression of DNA encoding antibody variable and/or constant regions. Particular examples include, chimeric antibodies, where the $V_H$ and/or $V_L$ domains of the antibody come from a different source to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source. Construction of chimeric and CDR-grafted antibodies is described, for example, in European Patent Applications: EP-A 0194276, EP-A 0239400, EP-A 0451216 and EP-A 0460617.

The following examples are provided for the purpose of illustration and are not intended to limit the scope of the present invention.

EXAMPLES

Example 1

The following example describes the identification, cloning and sequencing of the carotene synthase gene of the present invention.

Using an internal source of 8500 clones which had been previously sequenced from a *Schizochytrium* cDNA library, but which were not publicly available, BLAST searches were performed with the clone sequences. The translated sequence of one of these cDNA clones, designated LIB3033-014-Q1-E1-C9, showed strong homology to known phytoene synthase (PS) genes.

Starting with this DNA sequence of approximately 400 base pairs, the present inventors undertook an effort to isolate the *Schizochytrium* gene having homology to known PS genes. A series of DNA primers were designed and used in "Genome Walker" PCR protocols with *Schizochytrium* chromosomal DNA as a template to sequentially identify adjacent DNA regions. The libraries were constructed using a commercial kit (Clonetech, Inc.; Palo Alto, Calif.) and *Schizochytrium* genomic DNA. Successful PCR products were cloned into *E. coli* and the plasmid DNA was purified for sequencing. Additionally, one application of "Inverted PCR" was used (iPCR; Sambrook et al., Molecular Cloning, 1989, supra). These efforts resulted in a "contig" of approximately 5085 bp that contained distinct regions homologous to known phytoene dehydrogenase (PD) and lycopene cyclase (LC) genes as well as to PS genes. Despite sequence ambiguities inherent in PCR-generated fragments, it appeared highly likely that the three regions of homology formed a single open reading frame (ORF) with the order 5'-PD-PS-LC-3'. This prospective gene was named carotene synthase (CS). These activities represent three consecutive steps in carotenoid biosynthesis that, if functional, would be sufficient to convert geranylgeranyl pyrophosphate (GGPP) to β-carotene.

A more detailed examination of the EST libraries subsequently identified two other members with homology to the CS contig. A first clone, designated LIB81-022-Q1-E1-G1, is homologous to the CS ORF just upstream of LIB3033-014-Q1-E1-C9 without overlapping it. A second clone, designated LIB81-021-Q1-E1-H1, starts upstream of (outside of) the CS contig and extends about 208 bp into the contig. This EST likely represented an upstream neighboring gene, but no homology to known genes was detected by BLAST. The presence of this EST member strongly suggests that the CS contig contains the entire 5' region of the CS gene including control (promoter) sequences.

The 5085 bp contig described above extended from about 1400 bp upstream of the likely gene start codon and extended through most of the LC domain. That is, no stop codon consistent with the proposed gene structure was detected. Also, there were obvious sequence errors in the contig typical of PCR-generated fragments and "one pass" sequencing reactions. Therefore, it was necessary to obtain and carefully sequence a clone of the CS gene obtained from *Schizochytrium* genomic DNA. Several genomic libraries in a lambda phage vector (Lambda Fix II; Stratagene, La Jolla, Calif.) had been constructed within the present inventors' laboratories. The present inventors devised a strategy in which a phage would only be considered a "prospective CS clone" if its DNA clearly hybridized with two probes. A number of PCR primer pairs from the PS, LC, and "upstream" (the region 5', or upstream, of the likely ORF start) regions were evaluated for strong, single-product PCR fragments using *Schizochytrium* genomic DNA as template. The best PS-derived fragment was selected and used to probe a recombinant genomic library consisting of DNA fragments from *Schizochytrium* sp. ATCC20888 genomic DNA inserted into vector Lambda FIX II. The PS probe was a digoxigenin labeled probe corresponding to part of PS domain of the prospective carotene synthase open reading frame. Clones giving positive signals were subsequently probed with a digoxigenin labeled fragment generated from the sequence upstream ("5-prime") of the expected start of the carotene synthase gene.

One lambda clone giving hybridization signals to both probes was further characterized by sub-cloning and sequencing. Restriction analysis showed that the DNA from this phage contained a cloned insert of about 18-20 kb. This insert was further shown to contain two internal NotI restriction sites in addition to the two NotI sites in the phage vector that flank the inserted DNA. Thus, the inserted DNA could be identified as three NotI fragments of approximate sizes of 1.2, 6, and 12 kb. Given that the contig sequence and restriction patterns of PCR fragments predicted a diagnostic NotI site ca. 140 bp downstream of the likely ATG start codon (i.e., bp1542-1549 in SEQ ID NO:1), these three NotI fragments were sub-cloned into a plasmid vector (pBluescript II SK+) for sequencing. Six constructs were obtained representing the three fragments in each of the two orientations. Likewise, two sub-clones were obtained encompassing the entire 20 kb insert using the XbaI enzyme (i.e., two XbaI sites in the phage vector flank the insertion and there are no internal XbaI sites).

| | |
|---|---|
| pCX010, pCX011 | 1.2 kb NotI fragment inserts |
| pCX012, pCX013 | 6 kb NotI fragment inserts |
| pCX014, pCX015 | 12 kb NotI fragment inserts |
| pCX016, pCX017 | 20 kb XbaI fragment inserts |

Sequencing of the three NotI fragments from vector primers (across the NotI cloning sites and into the *Schizochytrium* DNA) clearly revealed that the CS gene had been obtained in its entirety (presuming no or only small introns—it is believed that *Schizochytrium* genomic DNA does not contain introns). Specifically, the 1.2 kb NotI fragment represented the upstream and first 140 bp of the predicted CS ORF (very likely containing the promoter elements), and the 12 kb NotI fragment represented the remainder of the gene. Apparently, the 6 kb NotI fragment represented sequences significantly downstream of the CS gene.

The 1.2 kb and 12 kb NotI clones have been used for multiple sequence reactions. The XbaI fragment clones have been used to confirm the sequence across the NotI site in the CS gene. Every base in the expanded contig (except for those at the extreme upstream 5' and downstream 3' ends; see below) has been sequenced from both strands at least once.

These efforts have produced a sequence determined for the CS contig consisting of 6525 bp. The CS ORF contains 1268 amino acids that are clearly separated by BLAST analysis into PD (ca. 469aa), PS (ca. 275aa), and LC (ca. 222aa) domains with obvious homologies as described above. These three domains are separated by regions of 50-60 amino acids that contain no detectable homology to known sequences. These interdomain regions could be simple linker regions or enzymatic "hinges". The three activity domains are internally contiguous by BLAST. Thus, it would seem unlikely that there are introns in the CS gene.

The first 5898 bp of the 6525 bp contig, which contains the CS ORF and regulatory regions, is represented herein by SEQ ID NO:1. The CS ORF, spanning from positions 1406 to 5212 (including the stop codon) of SEQ ID NO:2, is represented herein by SEQ ID NO:2. SEQ ID NO:2 encodes a 1268 amino acid carotene synthase of the present invention, represented herein by SEQ ID NO:3. Referring now to SEQ ID NO:3, the first domain in the CS protein, the phytoene dehydrogenase (PD) domain, spans from amino acid 53 to 521 of SEQ ID NO:3 and is represented herein by SEQ ID NO:5. SEQ ID NO:5 is encoded by the nucleic acid sequence represented herein by SEQ ID NO:4 (positions 157 to 1563 of SEQ ID NO:2). The second domain in the CS protein, the phytoene synthase (PS) domain, spans from amino acid 586 to 860 of SEQ ID NO:3 and is represented herein by SEQ ID NO:7. SEQ ID NO:7 is encoded by the nucleic acid sequence represented herein by SEQ ID NO:6 (positions 1756 to 2580 of SEQ ID NO:2). The third domain in the CS protein, the lycopene cyclase (LC) domain, spans from amino acid 911 to 1132 of SEQ ID NO:3 and is represented herein by SEQ ID NO:9. SEQ ID NO:5 is encoded by the nucleic acid sequence represented herein by SEQ ID NO:8 (positions 2731 to 3396 of SEQ ID NO:2).

The initial (N-terminal) 50-52 amino acids of the CS protein (SEQ ID NO:3) do not show homology to PD genes. Instead, the first 29 amino acids are predicted with high probability to represent a signal sequence (Center for Biological Sequence Analysis, Technical University of Denmark). It is likely that this sequence targets the enzyme to an intracellular organelle, possibly the endoplasmic reticulum. There is a ca.135 C-terminal amino acid stretch with no significant homology to known genes.

The upstream region of the contig consists of 1405 bp in front of the start ATG (positions 1-1405 of SEQ ID NO:1). Positions 1-345 of SEQ ID NO:1 represent sequence data from the original PCR-derived fragments and should be regarded with some caution since some sequence errors can be inherently introduced through PCR. Sequencing of the 1.2 kb NotI fragment clearly identifies an "end" at a Sau3AI site at bp346-349 of the contig (positions 346-349 of SEQ ID NO:1) that must have been the location of the partial cleavage reaction during the construction of the lambda library. BLAST of the upstream sequence reveals no significant homology to known genes, though an EST has been located to this region (see above). For the purposes of the invention, positions 1-1405, or at least positions 346-1405 represent regulatory regions of the CS gene of the invention which are likely to contain the CS gene promoter.

Analysis of the downstream region reveals an ORF (ORF2) originating outside of the contig and reading toward the end of the CS gene. The likely stop codon for ORF2 results in an intergenic region of ca. 690 bp. In the middle of this region is an interesting feature of unknown function: a stretch of 42 bp (bp5698-5739 in SEQ ID NO:1) with perfectly alternating TATAT, etc. BLAST of the 625 bp of ORF2 reveals strong homology to protein kinase enzymes from a wide variety of eukaryotic sources (data not shown). Sequencing of both strands has confirmed the nucleotides up to bp6479 of the contig. Thus, a high degree of confidence exists for the nucleotide sequence from bp346 to bp6479 of the "6525 bp CS contig", positions 346-5898 of which are shown in SEQ ID NO:1. The portion of the 6525 bp contig which was omitted from SEQ ID NO:1 is the beginning of the coding region for the ORF 2 gene discussed directly above.

A comparison of each of SEQ ID NO:3 (CS), SEQ ID NO:5 (PD domain), SEQ ID NO:7 (PS domain) and SEQ ID NO:9 (LC domain) with the public sequence databases revealed the following information regarding similar sequences. SEQ ID NO:5, representing the phytoene dehydrogenase domain, was 34% identical over 488 amino acids (50% homologous) to phytoene dehydrogenase from *Halobacterium* sp. (NC_002607); 32% identical over 476 amino acids (51% homologous) to phytoene dehydrogenase from *Methanothermobacter thermautotrophicus* (NC_000916); and 33% identical over 491 amino acids (47% homologous) to phytoene dehydrogenase from *Corynebacterium glutamicum* (NC_003450).

SEQ ID NO:7, representing the phytoene synthase domain, was 29% identical over 292 amino acids (39% homologous) to phytoene synthase from *Mycobacterium aureum* (AJ133724); 30% identical over 269 amino acids (39% homologous) to probable phytoene synthase from *Streptomyces coelicolor* (AL109962); 37% identical over 138 amino acids (47% homologous) to phytoene synthase from *Streptomyces griseus* (AF272737).

SEQ ID NO:9, representing the lycopene cyclase domain, was 31% identical over 230 amino acids (45% homologous) to lycopene cyclase/phytoene synthase from *Phycomyces blakesleeanus* (AJ278287); 31% identical over 230 amino acids (45% homologous) to phytoene synthase/lycopene cyclase from *Phycomyces blakesleeanus* (AJ276965); 29% identical over 245 amino acids (45% homologous) to phytoene synthase from *Neurospora crassa* (L27652); and 30% identical over 193 amino acids to carotene cyclase from *Gibberella fujikuroi* (AJ426-417).

SEQ ID NO:3, representing the entire carotene synthase protein of the invention, was 34% identical over 488 amino acids (51% homologous) to phytoene dehydrogenase from *Halobacterium* sp. (NP_280452.1); 33% identical over 480 amino acids (52% homologous) to phytoene dehydrogenase from *Methanogthermobacter thermoautotrophicus* (NP_276913.1); and 33% identical over 480 amino acids (47% homologous) to phytoene dehydrogenase from *Corynebacterium glutamicum* (NP_599858.1).

Example 2

The following example demonstrates the expression and function of the carotene synthase gene of the invention.

Subsequent efforts have centered on demonstrating function of the CS gene. Successful expression and function of the CS gene in homologous and heterologous hosts would be of great benefit for using the CS gene and its product in a variety of applications. Toward these ends, three parallel expression plasmid designs were prepared. Additionally, plasmids designed to "knock out" chromosomal CS gene expression either by single cross-over homologous recombination or double cross-over recombination have been constructed and tested by transformation (see Example 3). Details of plasmid construction are as follows.

pCSZEO1 and pCSZEO2: (for Expression of CS and LC-Defective CS from its Native Promoter)

The ca. 5.1 kb EcoRI fragment from pCX017 (containing the entire CS ORF (positions 1406-5212 of SEQ ID NO:1)), all of the upstream cloned DNA (positions 1-1405 of SEQ ID NO:1), and ca. 270 bp of downstream DNA (position 5213 to position 5485 of SEQ ID NO:1) was cloned into the EcoRI site of pBluescript SK(+) (Stratagene). A construct with the desired insert orientation is pBSKCS6.

A HindIII fragment (ca. 950 bp) was removed from pBSKCS6 by digestion, dilution, and re-ligation to create pBSKCS6ΔH. This deletion utilizes the HindIII site in the LC domain (bp4552-4557 in SEQ ID NO:1) and removes the distal half of the LC domain and all downstream *Schizochytrium* sequences.

Next, a small (ca. 60 bp) XbaI fragment from vector sequences was removed from pBSKCS6 and pBSKCS6ΔH by digestion, dilution, and re-ligation to create pBSKCS6ΔX and pBSKCS6ΔHΔX, respectively. The removal of the small XbaI fragment facilitates the subsequent step.

A ca. 1060 bp XbaI fragment from pTUBZEO11-2 (a *Schizochytrium* transformation vector, described in detail in copending U.S. patent application Ser. No. 10/124,807, supra) containing the containing a *Schizochytrium* tubulin gene promoter (tub promoter), ble Zeocin resistance gene, and viral SV40 terminator (the "TZS" cassette), was then cloned into the XbaI sites of pBSKCS6ΔX and pBSKCS6ΔHΔX to generate pCSZEO1 and pCSZEO2, respectively.

pTUBCS11, pTUBCS12, pTUBCS13, and pTUBCS14 (for Expression of CS, LC-Defective CS, and Signal Sequence-Defective CS from the Tubulin Promoter)

A 213 bp PstI/EcoRI fragment from pTUBZEO11-2 comprising the proximal half of the tub promoter was directionally cloned into the compatible site of vector pUC9 to yield pUC-TUB.

Plasmid pTZS5 was created by inserting the ca. 880 bp EcoRI fragment from pTUBZEO11-2 (described above, containing the distal half of the tub promoter, Zeocin resistance gene, and SV40 terminator) into the unique EcoRI site of pUC-TUB. Proper orientation was determined by diagnostic restriction digests. This procedure effectively transfers the "TZS" cassette into pUC9 in order to take advantage of certain restriction sites in subsequent steps.

Next, PCR fragments were generated from the beginning of the CS gene in order to allow cloning into a desired *E. coli* expression vector that contains a NcoI site at the start codon. Two reactions were planned: one to produce a protein with the native N-terminus and a second to produce a protein deficient in the putative signal sequence (see Example 1). These NcoI site-containing constructs were then transferred to pTZS5 for tubulin promoter-driven expression for *Schizochytrium*. Also, these constructs were further developed for expression in *E. coli* (see below). PCR primer CAX049 was designed to convert the CS start ATG codon (bp 1406-1408 in SEQ ID NO:1 to a NcoI restriction site (CCATGG). Likewise, primer CAX050 was designed to simultaneously convert the codon for aa29 (bp 1490-1492 in SEQ ID NO:1) to a start ATG and a NcoI site. Neither primer produces a change in the downstream codons for aa2 or aa30, respectively. A reverse primer (CAX048) was chosen downstream of the KpnI site (bp1859-1864 of SEQ ID NO:1) to generate a 510 bp product with CAX049 and a 426 bp product with CAX050 using pCX016 as template.

The DNA from the PCR reactions described directly above was digested with NcoI and KpnI, and fragments were gel-purified and separately cloned into the compatible site of the commercially-available expression vector pTrcHis2B (Invitrogen; Carlsbad, Calif.) resulting in plasmids pCSNK2 (native N terminus) and pCSNK18 (shortened N terminus). This vector drives expression in *E. coli* from a highly active trc promoter. It also contains a $lacI_q$ gene for inducible expression control (with IPTG) and efficient transcription terminators downstream of the multiple cloning site. The vector is further designed to add a $(His)_6$ tag to the C terminus of expressed proteins, but this feature was made irrelevant by the cloning steps described here. The DNA sequences of the inserts of pCSNK2 and pCSNK18 were determined and shown to contain the desired NcoI sites and to otherwise match the known CS gene sequence.

The ble (Zeocin resistance) gene in pTZS5 (and in pTUBZEO11-2) exists as a NcoI/PmlI fragment in which the ATG of the NcoI site is the start codon. Digestion with PmlI yields blunt ends. To transfer the N-terminal CS coding regions from pCSNK2 and pCSNK18 to pTZS5, a DraI site (blunt end) in the pTrcHis2B vector just downstream of the (His)$_6$ tag coding region was exploited. The NcoI/DraI fragments from pCSNK2 and pCSNK18 were obtained by gel-purification following restriction enzyme digestion. The large vector fragment from pTZS5 digested with NcoI and PmlI (lacking the ble gene) was similarly obtained. Cloning of the NcoI/DraI fragments into the pTZS5 vector fragment produced pTUBCS2 (full length N-terminus) and pTUBCS3 (shortened N terminus) with the CS gene fragment now "behind" the tubulin promoter.

Finally, C-terminal portions of the CS gene were added to pTUBCS2 and pTUBCS3. Each plasmid was linearized by digestion with KpnI and treated with shrimp alkaline phosphatase (SAP) to minimize subsequent re-ligation of vector ends. KpnI fragments from pBSKCS6 and pBSKCS6ΔH (see above) were prepared by digestion and gel purification. These fragments extend from the KpnI site early in the CS gene (preserved by the design of the PCR fragments described above) to a vector KpnI site downstream of the CS gene. As such, they contain full length or truncated (LC-deficient) portions, respectively, of the CS C-terminus. Each insert fragment was ligated with each vector preparation resulting in the four possible variants of +/− signal sequence (SS) and +/− LC domain. Appropriate orientation of the inserts was confirmed by restriction digests. The nomenclature is as follows (see table below): pTUBCS11: SS+, LC+; pTUBCS12: SS+, LC−; pTUBCS13: SS−, LC+; pTUBCS14: SS−, LC−. These plasmids effectively result in the substitution of the ble gene in the tub/ble/SV40 construct with various forms of the CS gene while maintaining the same position of the translational start site. They contain no selectable marker for transformation of Schizochytrium and must be introduced by co-transformation.

pTHCS1, pTHCS2, pTHCS3, pTHCS4, pATCS1, pATCS2, pATCS3, and pATCS4: (for Expression of CS, LC-Defective CS, and Signal Sequence-Defective CS in E. coli)

Plasmids pCSNK2 and pCSNK18 (see above) were each treated with KpnI+EcoRI or KpnI+HindIII to prepare vector fragments (SS+/−) for subsequent addition of C-terminal DNA fragments. Plasmid pBSKCS6 (see above) was likewise treated with KpnI+EcoRI or KpnI+HindIII to release C-terminal fragments with or without, respectively, the CS domain. (The relevance of the HindIII and KpnI sites have been described; the EcoRI site lies in vector sequences downstream of the CS gene.) Ligations of vector fragment with insert fragments were as follows:

| vector fragment | insert fragment from pBSKCS6 | resulting plasmid |
| --- | --- | --- |
| pCSNK2 | KpnI + EcoRI | pTHCS1 (SS+/LC+) |
| KpnI + EcoRI (SS+) | (LC+) | pTHCS2 (SS+/LC−) |
| pCSNK2 | KpnI + HindIIII | |
| KpnI + HindIIII (SS+) | (LC−) | pTHCS3 (SS−/LC+) |
| pCSNK18 | KpnI + EcoRI | |

| vector fragment | insert fragment from pBSKCS6 | resulting plasmid |
| --- | --- | --- |
| KpnI + EcoRI (SS−) | (LC+) | pTHCS4 (SS−/LC−) |
| pCSNK18 | KpnI + HindIIII | |
| KpnI + HindIII (SS−) | (LC−) | |

Plasmids pTHCS1 through 4 are designed for expression of the CS gene and variants thereof in E. coli. Expression from these plasmids could be detected by Western blot using antisera/antibodies generated against the CS gene (see below). However, functional expression of CS from these plasmids in E. coli will not result in carotenoid production because this bacterium does not normally synthesis the predicted substrate for the CS enzyme, geranylgeranyl pyrophosphate (GGPP). Various E. coli strains have been described in the literature that synthesize GGPP due to the presence of certain cloned genes. These cloned genes are typically carried on cloning vectors incompatible with pTHCS1 through 4. Therefore, a new set of plasmids designed for expression of the CS gene (and variants) in a compatible vector were constructed. Plasmid pACYC184 was chosen as the compatible vehicle for potential co-expression of the CS variants with the GGPP-conferring plasmid described in the literature. Restriction sites in pACYC184 and the pTHCS1-4 constructs were chosen to allow transfer or the trc/CS/terminator and lacI$_q$ regions to pACYC184 without the ori (origin of plasmid replication in pTrcHis2B) or the β-lactamase gene (the GGPP-conferring plasmid carries the β-lactamase gene and requires ampicillin for maintenance). Specifically, pACYC184 was digested with AseI and NruI to yield a vector fragment containing the ori from pACYC184 and the chloramphenicol-resistance gene but not the tetracycline-resistance gene. The pTHCS1-4 plasmids were digested with NdeI and ScaI to provide fragments with the aforementioned attributes. Cloning of the resulting trc/CS/terminator/lacI$_q$ fragments into the partial pACYC184 vector was facilitated by the facts that NruI and ScaI digestion yields blunt ends, and AseI and NdeI digestion yield compatible 2 bp 5' overhangs. Thus, directional cloning produced the four CS constructs from pTHCS1, 2, 3, and 4 in pACYC184 named pATCS1, 2, 3, and 4, respectively. It is expected that functional expression of the CS gene (and variants) from pATCS1 through 4 in GGPP-synthesizing E. coli strains would yield carotenoid pigments detectable both visually and spectrophotometrically. Such production would validate functional expression of the CS gene in heterologous organisms.

Biolistic Transformation Protocol

The transformation procedure closely follows that originally described in U.S. patent application Ser. No. 10/124, 807, supra. The Biolistic PDS-1000/He Particle Delivery System (Bio-Rad) is used. For each bombardment, about 5 µg of plasmid DNA is coated onto 3 mg M-10 tungsten microcarriers. Bombardment of Schizochytrium is carried out using 1100 or 1350 psi rupture discs. After 4-6 hr of "grow-out", bombarded cells are applied to agar plates containing 150-300 µg/ml Zeocin (Invitrogen). Transformants are typically recovered in 4-8 days.

Experimental Design and Results

1. Expression of the CS Gene Driven by its Native Promoter and Followed by its Native Terminator.

Plasmids were generated containing the CS gene and include the Zeocin-resistance cassette ("TZS"; *Schizochytrium* tubulin gene promoter, Zeocin [bleomycin] resistance gene [ble], and viral SV40 terminator) as described above.

Transformation of *Schizochytrium* with pCSZEO1 (full length CS gene) and pCSZEO2 (LC domain deletion—see above) resulted in about 800 Zeocin-resistant colonies per μg DNA for either plasmid, whereas transformants of control plasmid pTUBZEO11-2 was about 300/μg. Control transformants were generally uniform in color, but transformants from the pTUBCS appeared to have a gradation of pigmentation from normal pale yellow to yellow/orange. Strains that produce the most pigmented colonies have been saved for further study. One pTUBZEO1 transformant, B4-2, and one pTUBZEO2 transformant, B4-15, contained 92 and 40 ppm β-carotene, respectively, in an experiment in which a control transformant contained 16 ppm β-carotene. These results suggest that the CS gene is functional, can be over-expressed, and exhibits a "gene copy number" effect. Interestingly, the pTUBZEO2 transformant did not produce detectable lycopene as might be expected. Perhaps lycopene produced by the truncated CS gene is this construct is efficiently converted to β-carotene by the original full-length copy of the CS gene.

2. The CS Gene Driven by the Tubulin Gene Promoter and Followed by the SV40 Terminator In concept, the "TUB/ZEO/SV40" promoter described above was used with the CS gene replacing the Zeocin resistance gene. Without positive selection, this plasmid construct was introduced into *Schizochytrium* by co-transformation. As described in U.S. patent application Ser. No. 10/124,807, supra, co-transformation using this system can occur at efficiencies of 50% or more.

In initial experiments with pTUBCS11 or pTUBCS13 co-transformed with pTUBZEO11-2, very few Zeocin resistant colonies were obtained (ca. 1/μg DNA). Approximately 10 Zeocin-resistant transformants from each plasmid have been obtained to date. One transformant from pTUBCS11, B5-1, is visually the most pigmented strain and has been shown in one experiment to contain 115 ppm β-carotene (control: 16 ppm; see below). Pigment production is notably greater than the control, but only modestly greater that a presumed "gene copy number" effect described in the first experiment above.

To summarize, the expression designs above have up to four ORF variations. First is the full-length CS gene. Second is an ORF lacking the first 29 amino acids of SEQ ID NO:3; i.e., the putative signal sequence. In this case, the ORF is engineered with an ATG start codon and useful restriction site at amino acid 29. It is possible that overexpression of the full-length CS gene in *Schizochytrium* could poison the intracellular target for the protein. Similarly, there is a possibility that a signal sequence could poison the bacterial system. The third variation is a CS ORF truncated in the middle of the LC domain. If functional, the resulting PD/PS enzyme should convert GGPP to lycopene. This PD/PS enzyme would itself be a unique activity pairing among carotenoid biosynthetic enzymes. The fourth variation is a combination of the signal sequence and LC deletions. The plasmid designations are as follows:

| plasmid | promoter | signal seq. | LC domain | selection |
|---|---|---|---|---|
| 1 pCSZEO1 | native | + | + | zeocin |
| pCSZEO2 | native | + | − | zeocin |
| 2 pTUBCS11 | tubulin | + | + | (none) |
| pTUBCS12 | tubulin | + | − | (none) |
| pTUBCS13 | tubulin | − | + | (none) |
| pTUBCS14 | tubulin | − | − | (none) |
| 3 pATCS1 | trc | + | + | Cm |
| pATCS2 | trc | + | − | Cm |
| pATCS3 | trc | − | + | Cm |
| pATCS4 | trc | − | − | Cm |

Example 3

This example describes the inactivation of a carotene synthase gene in *Schizochytrium*.

Plasmid Construction pCSKO1, pCSKO2, and pCSKO3

An internal CS ORF fragment (KpnI to HindIII; 2689 bp) was cloned into the compatible site in the commercial vector pTrcHis2B to give plasmid pL35-4.

Plasmid pL35-4 was further amended to include the "TZS" cassette from pTUBZEO1-2 as an 1122 bp XbaI fragment by linearization of pL35-4 with XbaI, treatment with shrimp alkaline phosphatase, and ligation with the gel-purified 1122 bp XbaI fragment from pTUBZEO11-2. The resulting plasmid, pCSKO1, is designed to inactivate ("knock out") the chromosomal CS gene by single cross-over homologous recombination following transformation into *Schizochytrium* with selection for Zeocin resistance.

For plasmids designed to knock out the CS gene by double cross-over homologous recombination, the entire CS gene (including all of the known up-steam region and about 270 bp of down stream region (to the EcoRI site at bp5480-5485 of SEQ ID NO:1)) on a ca. 50.1 kb EcoRI fragment from pCX017 (see above) was cloned into the EcoRI site of vector pUC9 (following restriction enzyme digestion and phosphatase treatment) resulting in pL36-3.

pL36-3 was treated with DraIII (single site; bp275-2773 of SEQ ID NO:1), Klenow fragment, and shrimp alkaline phosphatase to "open" the plasmid in the middle of the CS gene and create blunt ends. The TUB/ZEO/SV40 cassette XbaI fragment (see above) was similarly treated with Klenow fragment to create blunt ends and ligated into the linearized vector. Both insert orientations were obtained, and the resulting plasmids named pCSKO2 and pCSKO3. Sequencing of the DraIII/XbaI junctions has shown that three of the four junctions have the expected sequence; one junction in pCSKO3 has a single extra base pair.

Experimental Design

Upon transformation of *Schizochytrium* 20888 with pCSKO1 (designed for knock-out by a single crossover event), Zeocin resistant colonies were obtained at frequencies of ca. 325/μg plasmid DNA. (Notes: Frequencies for the control plasmid pTUBZEO11-2 were 60-140/μg plasmid DNA, and mock transformations in the absence of DNA yield no Zeocin resistant colonies.) Among the Zeocin resistant transformants from pCSKO1, ca. 1/220 formed white, pigmentless "albino" colonies. These data represented the first indication that the CS gene functions as predicted. Two "albino" transformants and a normally-pigmented transformant from the control plasmid pTUBZEO11-2 were grown for carotenoid analysis. Dried biomass samples were analyzed for carotenoid content. The "albino" strains had no detectable carotenoids whereas the control strain had modest amounts (16 ppm) of β-carotene.

Plasmid pCSKO2 is designed such that the majority of "albino" colonies arising from transformation are expected to be the result of gene disruption by double cross-over homologous recombination. Transformation of *Schizochytrium* with this plasmid resulted in ca. 400 Zeocin-resistant colonies per μg DNA, and ca. 5% of these were "albino". Carotenoid analysis revealed no detectable pigments in two selected strains (see below). Furthermore, PCR analysis of chromosomal DNA prepared from these strains showed that the CS gene was indeed disrupted by the "TZS" cassette and that no plasmid vector sequences were present. To test for CS gene structure, PCR primers CAX037 (bp2575-2594 of SEQ ID NO:1) and CAX046 (bp3006-3025 of SEQ ID NO:1) homologous to CS gene sequences that flank the site of the TZS cassette insertion were used. A disrupted gene is expected to produce a product of ca. 1570 bp with this primer pair. To test for the presence of vector sequences, two primer pairs at either end of the β-lactamase gene region were designed. Specifically, the bla3/bla4 primer pair is expected to produce a 627 bp product from the proximal portion of the β-lactamase gene, whereas the bla2/bla5 pair should give a 354 bp product from the distal portion of the β-lactamase gene. Analysis with both primer pairs is necessary in the event that recombination of the pCSKO2 plasmid occurred within the β-lactamase gene or otherwise between the locations of any two PCR primers. Results of PCR analysis of DNA from pCSKO2 transformants are as follows.

| strain | pigmentation | CAX037⊗CAX046 | bla3⊗bla4 | bla2⊗bla5 |
|---|---|---|---|---|
| B6-1 | none | ~1600 bp | none | none |
| B6-2 | none | ~1600 bp | none | none |
| B6-4(*) | yellow/orange | ~450 bp (major) ~1600 bp (minor) | ~630 bp | ~350 bp |

(*)pigmented transformant from pCSKO2

The "albino" transformants have only the interrupted CS gene and do not contain vector sequences (at least not the β-lactamase gene region). The pigmented transformant has the β-lactamase gene region and the un-interrupted CS gene. This latter strain also appears to have the interrupted CS gene as might be expected if the pCSKO2 plasmid integrated ectopically into the host chromosome. Presumably, the difference in intensity between the two PCR products reflects the differences in size and efficiencies of amplification. These results, then, are entirely consistent with CS gene disruption by double cross-over homologous recombination in the "albino" transformants from pCSKO2.

Following is a summary of the carotenoid analysis of selected transformants from Examples 2 and 3.

The table below shows the results of carotenoid analysis by HPLC of selected transformants grown in shake flasks. For these experiments, transformants were chosen based on a visual assessment of highest pigmentation. The transformants have been described above in Examples 2 and 3.

| | | Carotenoids in Selected Transformants | | |
|---|---|---|---|---|
| | strain | CS plasmid | β-carotene* | astaxanthin* | total carotenoids* |
| Exp. I (medium M50-20) | B3-1 | pCSKO1 | n.d. | n.d. | n.d. |
| | B3-2 | pCSKO1 | n.d. | n.d. | n.d. |
| | B3-15 | pTUBZEO11-2 | 16 | n.d. | 16 |
| | B4-2 | pCSZEO1 | 92 | n.d. | 92 |
| | B4-15 | pCSZEO2 | 40 | n.d. | 40 |
| | B5-1 | pTUBCS11 | 115 | n.d. | 115 |
| | B6-2 | pCSKO2 | n.d. | n.d. | n.d. |
| | B6-3 | pCSKO2 | n.d. | n.d. | n.d. |
| | B6-4 | pCSKO2 | 49 | n.d. | 49 |
| Exp. II (medium M2B) | B3-15 | pTUBZEO11-2 | 25 | 62 | 87 |
| | B4-2 | pCSZEO1 | 120 | 58 | 178 |
| | B5-1 | pTUBCS11 | 133 | 127 | 260 | n.d.; not detected
*ppm (μg/g dcw); no other carotenoids were detected in measurable quantities.

As shown in Experiment I, "albino" transformants from pCSKO1 (single cross-over; B3-1, B3-2) and pCSKO2 (double cross-over; B6-2, B6-3) contained no detectable carotenoids. A pigmented transformant of pCSKO2, B6-4, produced 49 ppm β-carotene. Given that pCSKO2 contains only an internal fragment of the CS gene (and no promoter), pigment produced by a non-"albino" transformant is expected to represent a basal or normal level. Consistent with a "gene copy number" explanation, B4-2, a transformant of pCSZEO1, contained about twice the basal level of β-carotene. Interestingly, B4-15, a representative transformant of the LC-defective pCSZEO2, contained near-basal levels of β-carotene and no lycopene. This result might suggest that the modified CS gene in this plasmid is completely non-functional. The highest β-carotene level was seen in strain B5-1, a co-transformant of the tubulin promoter-driven CS gene in pTUBCS11 with pTUBZEO11-2. However, β-carotene levels in B5-1 were only modestly greater than those in B4-2, suggesting either minimal benefit from the strong tubulin promoter or limiting amounts of upstream substrates.

In Experiment II, growth conditions resulted in the production of the xanthophyll astaxanthin in addition to β-carotene (but no significant amounts of intermediate carotenoids). Among the strains tested, the carotenoid production levels show the same relationship as those described for Experiment I. The "copy number" construct, pCSZEO1, yielded about twice the total carotenoid level as that from the control (pTUBZEO11-2), and the "over-expression" construct, pTUBCS11, yielded modestly greater amounts.

Example 4

The following example describes the production of a carotene synthase antibody.

The amino acid sequence of a preliminary version of the translated (partial) CS open reading frame was submitted to Strategic Biosolutions (Ramona, Calif.) for analysis by their proprietary software to predict the most antigenic regions/peptides. The following dodecapeptide from the PD domain was suggested to be highly antigenic: RLVDRLMDEAKA (aa176-187 of SEQ ID NO:3). This peptide was synthesized by ResGen (Huntsville, Ala.) and used to generate polyclonal antiserum in rabbits. Specifically, two New Zealand white rabbits were immunized by subcutaneous injection of 0.5 mg of peptide on day 1, week 2, week 6, and week 8. Blood was collected and sera prepared on day 0 (pre-bleed) and weeks 4, 8, and 10. Sera are stored frozen.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

---

What is claimed is:

1. A method for producing lipids lacking pigmentation from a biosynthetic process, comprising culturing under conditions effective to produce said lipids from microorganisms of the order Thraustochytriales, wherein said microorganisms have been genetically modified to selectively delete or inactivate a carotene synthase gene, wherein said carotene synthase gene comprises a nucleic acid sequence selected from the group consisting of:
   a. a nucleic acid sequence encoding SEQ ID NO:3; and
   b. a nucleic acid sequence encoding an amino acid sequence having at least 85% identity to SEQ ID NO:3, wherein a protein having said amino acid sequence has a biological activity selected from the group consisting of phytoene dehydrogenase (PD) activity, phytoene synthase (PS) activity, and lycopene cyclase (LC) activity.

2. A method for recovering lipids lacking pigmentation from a biosynthetic process, comprising recovering lipids from a culture of microorganisms of the order Thraustochytriales, wherein said microorganisms have been genetically modified to selectively delete or inactivate a carotene synthase gene, wherein said carotene synthase gene comprises a nucleic acid sequence selected from the group consisting of:
   a nucleic acid sequence encoding SEQ ID NO:3; and
   a nucleic acid sequence encoding an amino acid sequence having at least 85% identity to SEQ ID NO:3, wherein a protein having said amino acid sequence has a biological activity selected from the group consisting of phytoene dehydrogenase (PD) activity, phytoene synthase (PS) activity, and lycopene cyclase (LC) activity.

* * * * *